United States Patent
Bava et al.

(10) Patent No.: US 12,391,976 B2
(45) Date of Patent: *Aug. 19, 2025

(54) METHODS, KITS, AND COMPOSITIONS FOR PROCESSING EXTRACELLULAR MOLECULES

(71) Applicant: 10x Genomics, Inc., Pleasanton, CA (US)

(72) Inventors: Felice Alessio Bava, Pleasanton, CA (US); Geoffrey McDermott, Livermore, CA (US)

(73) Assignee: 10X GENOMICS, INC., Pleasanton, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/388,753

(22) Filed: Nov. 10, 2023

(65) Prior Publication Data

US 2024/0150812 A1    May 9, 2024

Related U.S. Application Data

(63) Continuation of application No. 17/318,364, filed on May 12, 2021, now Pat. No. 11,851,700.

(60) Provisional application No. 63/042,106, filed on Jun. 22, 2020, provisional application No. 63/024,042, filed on May 13, 2020.

(51) Int. Cl.
  *C12Q 1/6806*    (2018.01)
  *C12N 15/10*    (2006.01)

(52) U.S. Cl.
  CPC ....... *C12Q 1/6806* (2013.01); *C12N 15/1013* (2013.01)

(58) Field of Classification Search
  None
  See application file for complete search history.

(56) References Cited

U.S. PATENT DOCUMENTS

| | | |
|---|---|---|
| 4,124,638 A | 11/1978 | Hansen |
| 5,185,099 A | 2/1993 | Delpuech et al. |
| 5,270,183 A | 12/1993 | Corbett et al. |
| 5,478,893 A | 12/1995 | Ghosh et al. |
| 5,736,330 A | 4/1998 | Fulton |
| 5,756,334 A | 5/1998 | Perler et al. |
| 5,846,719 A | 12/1998 | Brenner et al. |
| 5,900,481 A | 5/1999 | Lough et al. |
| 5,942,609 A | 8/1999 | Hunkapiller et al. |
| 5,994,056 A | 11/1999 | Higuchi |
| 6,033,880 A | 3/2000 | Haff et al. |
| 6,057,149 A | 5/2000 | Burns et al. |
| 6,123,798 A | 9/2000 | Gandhi et al. |
| 6,171,850 B1 | 1/2001 | Nagle et al. |
| 6,172,218 B1 | 1/2001 | Brenner |
| 6,176,962 B1 | 1/2001 | Soane et al. |
| 6,306,590 B1 | 10/2001 | Mehta et al. |
| 6,327,410 B1 | 12/2001 | Walt et al. |
| 6,379,929 B1 | 4/2002 | Burns et al. |
| 6,406,848 B1 | 6/2002 | Bridgham et al. |
| 6,409,832 B2 | 6/2002 | Weigl et al. |
| 6,492,118 B1 | 12/2002 | Abrams et al. |
| 6,524,456 B1 | 2/2003 | Ramsey et al. |
| 6,586,176 B1 | 7/2003 | Trnovsky et al. |
| 6,632,655 B1 | 10/2003 | Mehta et al. |
| 6,915,679 B2 | 7/2005 | Chien et al. |
| 7,041,481 B2 | 5/2006 | Anderson et al. |
| 7,115,400 B1 | 10/2006 | Adessi et al. |
| 7,129,091 B2 | 10/2006 | Ismagilov et al. |
| 7,268,167 B2 | 9/2007 | Higuchi et al. |
| 7,282,370 B2 | 10/2007 | Bridgham et al. |
| 7,294,503 B2 | 11/2007 | Quake et al. |
| 7,323,305 B2 | 1/2008 | Leamon et al. |
| 7,544,473 B2 | 6/2009 | Brenner |
| 7,622,076 B2 | 11/2009 | Davies et al. |
| 7,622,280 B2 | 11/2009 | Holliger et al. |
| 7,645,596 B2 | 1/2010 | Williams et al. |
| 7,708,949 B2 | 5/2010 | Stone et al. |
| 7,772,287 B2 | 8/2010 | Higuchi et al. |
| 7,776,927 B2 | 8/2010 | Chu et al. |
| 7,842,457 B2 | 11/2010 | Berka et al. |
| 7,910,354 B2 | 3/2011 | Drmanac et al. |
| 7,927,797 B2 | 4/2011 | Nobile et al. |
| 7,960,104 B2 | 6/2011 | Drmanac et al. |
| 7,968,287 B2 | 6/2011 | Griffiths et al. |
| 8,053,192 B2 | 11/2011 | Bignell et al. |
| 8,133,719 B2 | 3/2012 | Drmanac et al. |

(Continued)

FOREIGN PATENT DOCUMENTS

| | | |
|---|---|---|
| EP | 1019496 B1 | 9/2004 |
| EP | 1841879 A2 | 10/2007 |

(Continued)

OTHER PUBLICATIONS

Oliver-Calixte, Nyoté J., et al. "Immobilization of lambda exonuclease onto polymer micropillar arrays for the solid-phase digestion of dsDNAs." Analytical chemistry 86.9 (2014): 4447-4454.*

(Continued)

*Primary Examiner* — Patrick T Lewis
(74) *Attorney, Agent, or Firm* — WILSON SONSINI GOODRICH & ROSATI

(57) ABSTRACT

Disclosed are methods, compositions and kits for contacting a sample containing a biological particle with a catalyst associated with or attached to a support. The biological particle may be cells and/or nuclei. The catalyst may be an enzyme configured to digest an extracellular molecule, such as an extracellular biological molecule, including extracellular nucleic acid molecules. In some examples, the biological particle is an aggregate of cells that is processed to single cells with a nuclease that is attached to a bead support. The bead and nuclease may subsequently be removed from the system. The single cells that result from the method can be used in single cell-based droplet systems for obtaining genome or transcriptome profiles of single cells.

19 Claims, 20 Drawing Sheets

(56) References Cited

U.S. PATENT DOCUMENTS

| | | |
|---|---|---|
| 8,168,385 B2 | 5/2012 | Brenner |
| 8,268,564 B2 | 9/2012 | Roth et al. |
| 8,273,573 B2 | 9/2012 | Ismagilov et al. |
| 8,298,767 B2 | 10/2012 | Brenner et al. |
| 8,304,193 B2 | 11/2012 | Ismagilov et al. |
| 8,318,433 B2 | 11/2012 | Brenner |
| 8,329,407 B2 | 12/2012 | Ismagilov et al. |
| 8,592,150 B2 | 11/2013 | Drmanac et al. |
| 8,658,430 B2 | 2/2014 | Miller et al. |
| 8,822,148 B2 | 9/2014 | Ismagliov et al. |
| 8,835,358 B2 | 9/2014 | Fodor et al. |
| 8,871,444 B2 | 10/2014 | Griffiths et al. |
| 8,889,083 B2 | 11/2014 | Ismagilov et al. |
| 8,975,302 B2 | 3/2015 | Light et al. |
| 9,012,390 B2 | 4/2015 | Holtze et al. |
| 9,029,083 B2 | 5/2015 | Griffiths et al. |
| 9,029,085 B2 | 5/2015 | Agresti et al. |
| 9,085,798 B2 | 7/2015 | Chee |
| 9,089,844 B2 | 7/2015 | Hiddessen et al. |
| 9,126,160 B2 | 9/2015 | Ness et al. |
| 9,156,010 B2 | 10/2015 | Colston et al. |
| 9,194,861 B2 | 11/2015 | Hindson et al. |
| 9,216,392 B2 | 12/2015 | Hindson et al. |
| 9,238,206 B2 | 1/2016 | Rotem et al. |
| 9,266,104 B2 | 2/2016 | Link |
| 9,290,808 B2 | 3/2016 | Fodor et al. |
| 9,328,382 B2 | 5/2016 | Drmanac et al. |
| 9,347,059 B2 | 5/2016 | Saxonov |
| 9,371,598 B2 | 6/2016 | Chee |
| 9,388,465 B2 | 7/2016 | Hindson et al. |
| 9,417,190 B2 | 8/2016 | Hindson et al. |
| 9,486,757 B2 | 11/2016 | Romanowsky et al. |
| 9,498,761 B2 | 11/2016 | Holtze et al. |
| 9,500,664 B2 | 11/2016 | Ness et al. |
| 9,567,631 B2 | 2/2017 | Hindson et al. |
| 9,593,365 B2 | 3/2017 | Frisen et al. |
| 9,623,384 B2 | 4/2017 | Hindson et al. |
| 9,637,799 B2 | 5/2017 | Fan et al. |
| 9,644,204 B2 | 5/2017 | Hindson et al. |
| 9,689,024 B2 | 6/2017 | Hindson et al. |
| 9,694,361 B2 | 7/2017 | Bharadwaj et al. |
| 9,701,998 B2 | 7/2017 | Hindson et al. |
| 9,764,322 B2 | 9/2017 | Hiddessen et al. |
| 9,824,068 B2 | 11/2017 | Wong |
| 9,868,979 B2 | 1/2018 | Chee et al. |
| 9,879,313 B2 | 1/2018 | Chee et al. |
| 9,946,577 B1 | 4/2018 | Stafford et al. |
| 9,951,386 B2 | 4/2018 | Hindson et al. |
| 9,957,558 B2 | 5/2018 | Leamon et al. |
| 9,975,122 B2 | 5/2018 | Masquelier et al. |
| 10,011,872 B1 | 7/2018 | Belgrader et al. |
| 10,017,759 B2 | 7/2018 | Kaper et al. |
| 10,030,261 B2 | 7/2018 | Frisen et al. |
| 10,053,723 B2 | 8/2018 | Hindson et al. |
| 10,059,989 B2 | 8/2018 | Giresi et al. |
| 10,071,377 B2 | 9/2018 | Bharadwaj et al. |
| 10,221,436 B2 | 3/2019 | Hardenbol et al. |
| 10,221,442 B2 | 3/2019 | Hindson et al. |
| 10,253,364 B2 | 4/2019 | Hindson et al. |
| 10,273,541 B2 | 4/2019 | Hindson et al. |
| 10,323,279 B2 | 6/2019 | Hindson et al. |
| 10,347,365 B2 | 7/2019 | Wong et al. |
| 10,357,771 B2 | 7/2019 | Bharadwaj et al. |
| 10,395,758 B2 | 8/2019 | Schnall-Levin |
| 10,400,280 B2 | 9/2019 | Hindson et al. |
| 10,428,326 B2 | 10/2019 | Belhocine et al. |
| 10,533,221 B2 | 1/2020 | Hindson et al. |
| 10,544,413 B2 | 1/2020 | Bharadwaj et al. |
| 10,549,279 B2 | 2/2020 | Bharadwaj et al. |
| 10,557,158 B2 | 2/2020 | Hardenbol et al. |
| 10,590,244 B2 | 3/2020 | Delaney et al. |
| 10,745,742 B2 | 8/2020 | Bent et al. |
| 10,752,949 B2 | 8/2020 | Hindson et al. |
| 10,774,374 B2 | 9/2020 | Frisen et al. |
| 10,815,525 B2 | 10/2020 | Lucero et al. |
| 10,829,815 B2 | 11/2020 | Bharadwaj et al. |
| 10,837,047 B2 | 11/2020 | Delaney et al. |
| 10,874,997 B2 | 12/2020 | Weitz et al. |
| 10,995,333 B2 | 5/2021 | Pfeiffer |
| 11,371,094 B2 | 6/2022 | Ryvkin et al. |
| 11,459,607 B1 | 10/2022 | Terry et al. |
| 11,467,153 B2 | 10/2022 | Belhocine et al. |
| 11,655,499 B1 | 5/2023 | Pfeiffer |
| 11,845,983 B1 | 12/2023 | Belhocine et al. |
| 11,851,683 B1 | 12/2023 | Maheshwari et al. |
| 11,851,700 B1 | 12/2023 | Bava et al. |
| 11,920,183 B2 | 3/2024 | Bharadwaj et al. |
| 11,952,626 B2 | 4/2024 | Pfeiffer et al. |
| 12,065,688 B2 | 8/2024 | Bell |
| 12,084,715 B1 | 9/2024 | Lund |
| 12,163,179 B2 | 12/2024 | Bell et al. |
| 12,169,198 B2 | 12/2024 | Price et al. |
| 12,188,014 B1 | 1/2025 | Price et al. |
| 12,235,262 B1 | 2/2025 | Giresi |
| 2002/0005354 A1 | 1/2002 | Spence et al. |
| 2002/0051971 A1 | 5/2002 | Stuelpnagel et al. |
| 2002/0092767 A1 | 7/2002 | Bjornson et al. |
| 2002/0119455 A1 | 8/2002 | Chan |
| 2002/0127736 A1 | 9/2002 | Chou et al. |
| 2003/0036206 A1 | 2/2003 | Chien et al. |
| 2003/0075446 A1 | 4/2003 | Culbertson et al. |
| 2003/0124509 A1 | 7/2003 | Kenis et al. |
| 2003/0215862 A1 | 11/2003 | Parce et al. |
| 2005/0130188 A1 | 6/2005 | Walt et al. |
| 2005/0250147 A1 | 11/2005 | Macevicz |
| 2005/0266582 A1 | 12/2005 | Modlin et al. |
| 2005/0287572 A1 | 12/2005 | Mathies et al. |
| 2006/0177832 A1 | 8/2006 | Brenner |
| 2006/0275782 A1 | 12/2006 | Gunderson et al. |
| 2007/0020640 A1 | 1/2007 | McCloskey et al. |
| 2007/0042419 A1 | 2/2007 | Barany et al. |
| 2007/0172873 A1 | 7/2007 | Brenner et al. |
| 2007/0190543 A1 | 8/2007 | Livak |
| 2007/0196397 A1 | 8/2007 | Torii et al. |
| 2007/0264320 A1 | 11/2007 | Lee et al. |
| 2008/0056948 A1 | 3/2008 | Dale et al. |
| 2008/0166720 A1 | 7/2008 | Hsieh et al. |
| 2008/0242560 A1 | 10/2008 | Gunderson et al. |
| 2009/0011943 A1 | 1/2009 | Drmanac et al. |
| 2009/0047713 A1 | 2/2009 | Handique |
| 2009/0099041 A1 | 4/2009 | Church et al. |
| 2009/0131543 A1 | 5/2009 | Weitz et al. |
| 2009/0148961 A1 | 6/2009 | Luchini et al. |
| 2009/0155563 A1 | 6/2009 | Petsev et al. |
| 2009/0202984 A1 | 8/2009 | Cantor |
| 2009/0235990 A1 | 9/2009 | Beer |
| 2009/0269248 A1 | 10/2009 | Falb et al. |
| 2009/0286687 A1 | 11/2009 | Dressman et al. |
| 2010/0035254 A1 | 2/2010 | Williams |
| 2010/0069263 A1 | 3/2010 | Shendure et al. |
| 2010/0086914 A1 | 4/2010 | Bentley et al. |
| 2010/0105866 A1 | 4/2010 | Fraden et al. |
| 2010/0184928 A1 | 7/2010 | Kumacheva |
| 2010/0216153 A1 | 8/2010 | Lapidus et al. |
| 2010/0248991 A1 | 9/2010 | Roesler et al. |
| 2010/0304982 A1 | 12/2010 | Hinz et al. |
| 2011/0217736 A1 | 9/2011 | Hindson |
| 2011/0305761 A1 | 12/2011 | Shum et al. |
| 2012/0071331 A1 | 3/2012 | Casbon et al. |
| 2012/0172259 A1 | 7/2012 | Rigatti et al. |
| 2012/0196288 A1 | 8/2012 | Beer |
| 2012/0219947 A1 | 8/2012 | Yurkovetsky et al. |
| 2013/0028812 A1 | 1/2013 | Prieto et al. |
| 2013/0109575 A1 | 5/2013 | Kleinschmidt et al. |
| 2014/0065234 A1 | 3/2014 | Shum et al. |
| 2014/0155295 A1 | 6/2014 | Hindson et al. |
| 2014/0221239 A1 | 8/2014 | Carman et al. |
| 2014/0272996 A1 | 9/2014 | Bemis |
| 2014/0274740 A1 | 9/2014 | Srinivasan et al. |
| 2014/0302503 A1 | 10/2014 | Lowe et al. |
| 2014/0338753 A1 | 11/2014 | Sperling et al. |
| 2014/0378345 A1 | 12/2014 | Hindson et al. |
| 2015/0267191 A1 | 9/2015 | Steelman et al. |
| 2015/0361418 A1 | 12/2015 | Reed |

(56) References Cited

U.S. PATENT DOCUMENTS

| | | |
|---|---|---|
| 2015/0376605 A1 | 12/2015 | Jarosz et al. |
| 2015/0376609 A1 | 12/2015 | Hindson et al. |
| 2015/0376700 A1 | 12/2015 | Schnall-Levin et al. |
| 2015/0379196 A1 | 12/2015 | Schnall-Levin et al. |
| 2016/0008778 A1 | 1/2016 | Weitz et al. |
| 2016/0024558 A1 | 1/2016 | Hardenbol et al. |
| 2016/0024572 A1 | 1/2016 | Shishkin et al. |
| 2016/0053253 A1 | 2/2016 | Salathia et al. |
| 2016/0059204 A1 | 3/2016 | Hindson et al. |
| 2016/0060621 A1 | 3/2016 | Agresti et al. |
| 2016/0122753 A1 | 5/2016 | Mikkelsen et al. |
| 2016/0122817 A1 | 5/2016 | Jarosz et al. |
| 2016/0203196 A1 | 7/2016 | Schnall-Levin et al. |
| 2016/0232291 A1 | 8/2016 | Kyriazopoulou-Panagiotopoulou et al. |
| 2016/0244809 A1 | 8/2016 | Belgrader et al. |
| 2016/0281160 A1 | 9/2016 | Jarosz et al. |
| 2016/0289769 A1 | 10/2016 | Schwartz et al. |
| 2016/0314242 A1 | 10/2016 | Schnall-Levin et al. |
| 2016/0348093 A1 | 12/2016 | Price et al. |
| 2017/0016041 A1 | 1/2017 | Greenfield et al. |
| 2017/0128937 A1 | 5/2017 | Hung et al. |
| 2017/0144161 A1 | 5/2017 | Hindson et al. |
| 2017/0145476 A1 | 5/2017 | Ryvkin et al. |
| 2017/0159109 A1 | 6/2017 | Zheng et al. |
| 2017/0235876 A1 | 8/2017 | Jaffe et al. |
| 2017/0260584 A1 | 9/2017 | Zheng et al. |
| 2018/0030515 A1 | 2/2018 | Regev et al. |
| 2018/0080075 A1 | 3/2018 | Brenner et al. |
| 2018/0105808 A1 | 4/2018 | Mikkelsen et al. |
| 2018/0312822 A1 | 11/2018 | Lee et al. |
| 2018/0312873 A1 | 11/2018 | Zheng |
| 2018/0340169 A1 | 11/2018 | Belhocine et al. |
| 2018/0371545 A1 | 12/2018 | Wong et al. |
| 2019/0060890 A1 | 2/2019 | Bharadwaj et al. |
| 2019/0060905 A1 | 2/2019 | Bharadwaj et al. |
| 2019/0064173 A1 | 2/2019 | Bharadwaj et al. |
| 2019/0071656 A1 | 3/2019 | Chang et al. |
| 2019/0127731 A1 | 5/2019 | McDermott |
| 2019/0134633 A1 | 5/2019 | Bharadwaj et al. |
| 2019/0176152 A1 | 6/2019 | Bharadwaj et al. |
| 2019/0177800 A1 | 6/2019 | Boutet et al. |
| 2019/0323088 A1 | 10/2019 | Boutet et al. |
| 2019/0345636 A1 | 11/2019 | McDermott et al. |
| 2019/0352717 A1 | 11/2019 | Schnall-Levin |
| 2019/0367997 A1 | 12/2019 | Bent et al. |
| 2019/0376118 A1 | 12/2019 | Belhocine et al. |
| 2020/0005902 A1 | 1/2020 | Mellen et al. |
| 2020/0032335 A1 | 1/2020 | Martinez |
| 2020/0033237 A1 | 1/2020 | Hindson et al. |
| 2020/0033366 A1 | 1/2020 | Alvarado Martinez |
| 2020/0056223 A1 | 2/2020 | Bell |
| 2020/0105373 A1 | 4/2020 | Zheng |
| 2020/0263232 A1 | 8/2020 | Bell et al. |
| 2020/0291454 A1 | 9/2020 | Belhocine et al. |
| 2020/0407775 A1 | 12/2020 | Bharadwaj et al. |
| 2021/0190770 A1 | 6/2021 | Delaney et al. |
| 2021/0270703 A1 | 9/2021 | Abousoud |
| 2022/0162671 A1 | 5/2022 | Pfeiffer et al. |
| 2022/0403375 A1 | 12/2022 | Martinez |
| 2023/0167496 A1 | 6/2023 | Bava |
| 2024/0002914 A1 | 1/2024 | Pfeiffer |
| 2024/0044877 A1 | 2/2024 | Price et al. |
| 2024/0272044 A1 | 8/2024 | Bava |

FOREIGN PATENT DOCUMENTS

| | | |
|---|---|---|
| EP | 1967592 B1 | 4/2010 |
| EP | 2540389 A1 | 1/2013 |
| EP | 2635679 B1 | 4/2017 |
| GB | 2097692 A | 11/1982 |
| GB | 2097692 B | 5/1985 |
| WO | WO-84/02000 | 5/1984 |
| WO | WO-95/30782 | 11/1995 |
| WO | WO-99/52708 | 10/1999 |
| WO | WO-2000008212 A1 | 2/2000 |
| WO | WO-2001002850 A1 | 1/2001 |
| WO | WO-0114589 A2 | 3/2001 |
| WO | WO-0190418 A1 | 11/2001 |
| WO | WO-2001089787 A2 | 11/2001 |
| WO | WO-2004002627 A2 | 1/2004 |
| WO | WO-2004065617 A2 | 8/2004 |
| WO | WO-2004069849 A2 | 8/2004 |
| WO | WO-2004091763 A2 | 10/2004 |
| WO | WO-2005021151 A1 | 3/2005 |
| WO | WO-2005049787 A9 | 6/2005 |
| WO | WO-2005082098 A2 | 9/2005 |
| WO | WO-2006040551 A2 | 4/2006 |
| WO | WO-2006078841 A1 | 7/2006 |
| WO | WO-2006096571 A2 | 9/2006 |
| WO | WO-2007081385 A2 | 7/2007 |
| WO | WO-2007081387 A1 | 7/2007 |
| WO | WO-2007089541 A2 | 8/2007 |
| WO | WO-2007133710 A2 | 11/2007 |
| WO | WO-2007140015 A2 | 12/2007 |
| WO | WO-2007147079 A2 | 12/2007 |
| WO | WO-2008021123 A1 | 2/2008 |
| WO | WO-2008109176 A2 | 9/2008 |
| WO | WO-2008121342 A2 | 10/2008 |
| WO | WO-2008134153 A1 | 11/2008 |
| WO | WO-2008150432 A1 | 12/2008 |
| WO | WO-2009011808 A1 | 1/2009 |
| WO | WO-2009015296 A1 | 1/2009 |
| WO | WO-2009085215 A1 | 7/2009 |
| WO | WO-2009152928 A2 | 12/2009 |
| WO | WO-2010033200 A2 | 3/2010 |
| WO | WO-2010104604 A1 | 9/2010 |
| WO | WO-2010117620 A2 | 10/2010 |
| WO | WO-2010148039 A2 | 12/2010 |
| WO | WO-2011028539 A1 | 3/2011 |
| WO | WO-2011047870 A1 | 4/2011 |
| WO | WO-2011056546 A1 | 5/2011 |
| WO | WO-2011066476 A1 | 6/2011 |
| WO | WO-2012048341 A1 | 4/2012 |
| WO | WO-2012061832 A1 | 5/2012 |
| WO | WO-2012083225 A2 | 6/2012 |
| WO | WO-2012106546 A2 | 8/2012 |
| WO | WO-2012112804 A1 | 8/2012 |
| WO | WO-2012112970 A2 | 8/2012 |
| WO | WO-2012116331 A2 | 8/2012 |
| WO | WO-2012142531 A2 | 10/2012 |
| WO | WO-2012142611 A2 | 10/2012 |
| WO | WO-2012149042 A2 | 11/2012 |
| WO | WO-2012166425 A2 | 12/2012 |
| WO | WO-2012167142 A2 | 12/2012 |
| WO | WO-2013019751 A1 | 2/2013 |
| WO | WO-2013036929 A1 | 3/2013 |
| WO | WO-2013055955 A1 | 4/2013 |
| WO | WO-2013096643 A1 | 6/2013 |
| WO | WO-2013126741 A1 | 8/2013 |
| WO | WO-2013134261 A1 | 9/2013 |
| WO | WO-2014028378 A2 | 2/2014 |
| WO | WO-2014108810 A2 | 7/2014 |
| WO | WO-2014165559 A2 | 10/2014 |
| WO | WO-2015015199 A2 | 2/2015 |
| WO | WO-2015044428 A1 | 4/2015 |
| WO | WO-2015164212 A1 | 10/2015 |
| WO | WO-2016040476 A1 | 3/2016 |
| WO | WO-2016061517 A2 | 4/2016 |
| WO | WO-2016126871 A2 | 8/2016 |
| WO | WO-2016168584 A1 | 10/2016 |
| WO | WO-2017015075 A1 | 1/2017 |
| WO | WO-2017066231 A1 | 4/2017 |
| WO | WO-2017180949 A1 | 10/2017 |
| WO | WO-2017184707 A1 | 10/2017 |
| WO | WO-2017197343 A1 | 11/2017 |
| WO | WO-2018039338 A1 | 3/2018 |
| WO | WO-2018091676 A1 | 5/2018 |
| WO | WO-2018119301 A1 | 6/2018 |
| WO | WO-2018119447 A2 | 6/2018 |
| WO | WO-2018172726 A1 | 9/2018 |
| WO | WO-2018191701 A1 | 10/2018 |
| WO | WO-2018213643 A1 | 11/2018 |

(56) References Cited

FOREIGN PATENT DOCUMENTS

| WO | WO-2018226546 A1 | 12/2018 |
|---|---|---|
| WO | WO-2018236615 A1 | 12/2018 |
| WO | WO-2019028166 A1 | 2/2019 |
| WO | WO-2019040637 A1 | 2/2019 |
| WO | WO-2019083852 A1 | 5/2019 |
| WO | WO-2019084043 A1 | 5/2019 |
| WO | WO-2019084165 A1 | 5/2019 |
| WO | WO-2019108851 A1 | 6/2019 |
| WO | WO-2019113235 A1 | 6/2019 |
| WO | WO-2019118355 A1 | 6/2019 |
| WO | WO-2019126789 A1 | 6/2019 |
| WO | WO-2019148042 A1 | 8/2019 |
| WO | WO-2019152108 A1 | 8/2019 |
| WO | WO-2019157529 A1 | 8/2019 |
| WO | WO-2019165318 A1 | 8/2019 |
| WO | WO-2019169028 A1 | 9/2019 |
| WO | WO-2019169347 A1 | 9/2019 |
| WO | WO-2019191321 A1 | 10/2019 |
| WO | WO-2019217758 A1 | 11/2019 |
| WO | WO-2020028882 A1 | 2/2020 |
| WO | WO-2020041148 A1 | 2/2020 |
| WO | WO-2020047004 A2 | 3/2020 |
| WO | WO-2020047007 A2 | 3/2020 |
| WO | WO-2020047010 A2 | 3/2020 |
| WO | WO-2020047007 A3 | 4/2020 |
| WO | WO-2020047005 A4 | 5/2020 |
| WO | WO-2020142779 A1 | 7/2020 |
| WO | WO-2020167862 A1 | 8/2020 |
| WO | WO-2020167866 A1 | 8/2020 |
| WO | WO-2020168013 A1 | 8/2020 |
| WO | WO-2020198532 A1 | 10/2020 |
| WO | WO-2021046475 A1 | 3/2021 |
| WO | WO-2021133845 A1 | 7/2021 |
| WO | WO-2021207610 A1 | 10/2021 |
| WO | WO-2021212042 A1 | 10/2021 |
| WO | WO-2021/222302 A1 | 11/2021 |
| WO | WO-2021222301 A1 | 11/2021 |
| WO | WO-2022103712 A1 | 5/2022 |
| WO | WO-2022182682 A1 | 9/2022 |
| WO | WO-2022182785 A1 | 9/2022 |
| WO | WO-2022271908 A1 | 12/2022 |
| WO | WO-2023076528 A2 | 5/2023 |

OTHER PUBLICATIONS

10X Genomics, Inc. CG000153 Rev A. Chromium Single Cell DNA Reagent Kits User Guide. 2018. 62 pages.
10X Genomics, Inc. CG000184 Rev A. Chromium Single Cell 3' Reagent Kits v3 User Guide with Feature Barcoding Technology for CRISPR Screening. 2018. 70 pages.
10X Genomics, Inc. CG000185 Rev B. Chromium Single Cell 3' Reagent Kits User Guide with Feature Barcoding Technology for Cell Surface Protein. 2018. 66 pages.
10X Genomics, Inc. CG000208 Rev E. Chromium Next GEM Single Cell V(D)J reagent Kits v1.1 User Guide with Feature Barcode Technology for Cell Surface Protein. 2020. 88 pages.
10X Genomics, Inc. CG000209 Rev D. Chromium Next GEM Single Cell ATAC Reagent Kits v1.1 User Guide. 2020.
10X Genomics, Inc. CG000239 Rev B. Visium Spatial Gene Expression Reagent Kits User Guide. 2020.
10X Genomics, Inc. CG00026. Chromium Single Cell 3' Reagent Kit User Guide. 2016.
10X Genomics, Inc. LIT00003 Rev B Chromium Genome Solution Application Note. 2017.
Abate, A.R. et al. "Beating Poisson encapsulation statistics using close-packed ordering" Lab on a Chip (Sep. 21, 2009) 9(18):2628-2631.
Adamson et al., "Production of arrays of chemically distinct nanolitre plugs via repeated splitting in microfluidic devices", Lab Chip 6(9): 1178-1186 (Sep. 2006).
Agasti, S.S. et al. "Photocleavable DNA barcode-antibody conjugates allow sensitive and multiplexed protein analysis in single cell" J Am Chem Soc (2012) 134(45):18499-18502.

Amini, S. et al. "Haplotype-resolved whole-genome sequencing by contiguity-preserving transposition and combinatorial indexing" Nature Genetics (2014) 46:1343-1349 doi:10.1038/ng.3119.
Anna et al.: Formation of dispersions using "flow focusing" in microchannels: Applied Physics Letters, vol. 82, No. 3, pp. 364-366 (2003).
Baret, "Surfactants in droplet-based microfluidics" Lab Chip (12(3):422-433 (2012).
Beer et al. On-Chip, Real-Time, Single-Copy Polymerase Chain Reaction in Picoliter Droplets. Anal Chem 79:8471-8475 (2007).
Braeckmans et al., Scanning the Code. Modern Drug Discovery. 2003:28-32.
Brenner et al.: In vitro cloning of complex mixtures of DNA on microbeads: physical separation of differentially expressed cDNAs. Proc Natl Acad Sci U S A. Feb. 15, 2000;97(4):1665-1670.
Buchman GW, et al. Selective RNA amplification: a novel method using dUMP-containing primers and uracil DNA glycosylase. PCR Methods Appl. Aug. 1993; 3(1):28-31.
Burns, et al. An Integrated Nanoliter DNA Analysis Device. Science. Oct. 16, 1998;282(5388):484-7.
Burns, et al. Microfabricated structures for integrated DNA analysis. Proc Natl Acad Sci U S A. May 28, 1996; 93(11): 5556-5561.
Burns, et al. The intensification of rapid reactions in multiphase systems using slug flow in capillaries. Lab Chip. Sep. 2001;1(1):10-15. Epub Aug. 9, 2001.
Chen, et al. Chemical transfection of cells in picoliter aqueous droplets in fluorocarbon oil. Anal Chem. Nov. 15, 2011;83(22):8816-20. doi: 10.1021/ac2022794. Epub Oct. 17, 2011.
Chien et al. "Multiport flow-control system for lab-on-a-chip microfluidic devices", Fresenius J. Anal Chem, 371:106-111 (Jul. 27, 2001).
Chu, et al. Controllable monodisperse multiple emulsions. Angew Chem Int Ed Engl. 2007;46(47):8970-4.
Clausell-Tormos et al., "Droplet-based microfluidic platforms for the encapsulation and screening of mammalian cells and multicellular organisms", Chem. Biol. 15:427-437 (2008).
Co-pending U.S. Appl. No. 16/434,076, inventor Giresi; Paul, filed Jun. 6, 2019.
Co-pending U.S. Appl. No. 16/434,084, inventor Giresi; Paul, filed Jun. 6, 2019.
Co-pending U.S. Appl. No. 16/434,102, inventors Price; Andrew D et al., filed Jun. 6, 2019.
Co-pending U.S. Appl. No. 16/737,762, inventors Price; Andrew D. et al., filed Jan. 8, 2020.
Co-pending U.S. Appl. No. 16/737,770, inventors Belhocine; Zahara Kamila et al., filed Jan. 8, 2020.
Co-pending U.S. Appl. No. 16/789,273, inventors Maheshwari; Arundhati Shamoni et al., filed Feb. 12, 2020.
Co-pending U.S. Appl. No. 17/014,909, inventor Giresi; Paul, filed Sep. 8, 2020.
Co-pending U.S. Appl. No. 17/148,942, inventors McDermott; Geoffrey et al., filed Jan. 14, 2021.
Co-pending U.S. Appl. No. 17/166,982, inventors McDermott; Geoffrey et al., filed Feb. 3, 2021.
Co-pending U.S. Appl. No. 17/175,542, inventors Maheshwari; Arundhati Shamoni et al., filed Feb. 12, 2021.
Co-pending U.S. Appl. No. 17/220,303, inventor Walter; Dagmar, filed Apr. 1, 2021.
Co-pending U.S. Appl. No. 17/381,612, inventor Martinez; Luigi Jhon Alvarado, filed Jul. 21, 2021.
Co-pending U.S. Appl. No. 17/512,241, inventors Hill; Andrew John et al., filed Oct. 27, 2021.
Co-pending U.S. Appl. No. 17/517,408, inventors Salmanzadeh; Alireza et al., filed Nov. 2, 2021.
Co-pending U.S. Appl. No. 17/518,213, inventor Lund; Paul Eugene, filed Nov. 3, 2021.
Co-pending U.S. Appl. No. 17/522,741, inventors Zheng; Xinying et al., filed Nov. 9, 2021.
Co-pending U.S. Appl. No. 17/545,862, inventor Katherine; Pfeiffer, filed Dec. 8, 2021.
Co-pending U.S. Appl. No. 17/573,350, inventor Nemec; Corey M., filed Jan. 11, 2022.

(56) References Cited

OTHER PUBLICATIONS

Co-pending U.S. Appl. No. 17/580,947, inventor Gibbons; Michael, filed Jan. 21, 2022.

Co-pending U.S. Appl. No. 18/046,843, inventor Toh; Mckenzi, filed Oct. 14, 2022.

Damean, et al. Simultaneous measurement of reactions in microdroplets filled by concentration gradients. Lab Chip. Jun. 21, 2009;9(12):1707-13. doi: 10.1039/b821021g. Epub Mar. 19, 2009.

Deshpande, R. A., et al., "Immobilization of RNase Rs via its carbohydrate moiety to aminoethyl-Bio-Gel P-2 and its application for the hydrolysis of RNA to 2', 3' cyclic nucleotides", Process Biochemistry 33.8 (1998): 819-824.

Drmanac et al., Sequencing by hybridization (SBH): advantages, achievements, and opportunities. Adv Biochem Eng Biotechnol. 2002;77 :75-101.

Duffy et al., Rapid Protyping of Microfluidic Systems and Polydimethylsiloxane, Anal Chem 70:4974-4984 (1998).

Eastburn, et al. Ultrahigh-throughput mammalian single-cell reverse-transcriptase polymerase chain reaction in microfluidic droplets. Anal Chem. Aug. 20, 2013;85(16):8016-21. doi: 10.1021/ac402057q. Epub Aug. 8, 2013.

Esser-Kahn, et al. Triggered release from polymer capsules. Macromolecules. 2011; 44:5539-5553.

Fernandez-Arrojo, L., et al., "Micro-scale procedure for enzyme immobilization screening and operational stability assays", Biotechnology letters 37.8 (2015): 1593-1600.

Gericke, et al. Functional cellulose beads: preparation, characterization, and applications. Chemical reviews 113.7 (2013): 4812-4836.

Goldstein, L., et al., "The chemistry of enzyme immobilization", Applied Biochemistry and Bioengineering, vol. 1, Elsevier, 1976, 23-126.

Guo, et al. Droplet microfluidics for high-throughput biological assays. Lab Chip. Jun. 21, 2012;12(12):2146-55. doi: 10.1039/c2lc21147e. Epub Feb. 9, 2012.

Gyarmati, et al. Reversible disulphide formation in polymer networks: a versatile functional group from synthesis to applications. European Polymer Journal. 2013; 49:1268-1286.

Hashimshony, et al. CEL-Seq: Single-Cell RNA-Seq by Multiplexed Linear Amplification. Cell Rep. Sep. 27, 2012;2(3):666-73. doi: 10.1016/j.celrep.2012.08.003. Epub Aug. 30, 2012.

Holtze, et al. Biocompatible surfactants for water-in-fluorocarbon emulsions. Lab Chip. Oct. 2008;8(10):1632-9. doi: 10.1039/b806706f. Epub Sep. 2, 2008.

Hug, et al. Measurement of the number of molecules of a single mRNA species in a complex mRNA preparation. J Theor Biol. Apr. 21, 2003;221(4):615-24.

Islam, et al. Highly multiplexed and strand-specific single-cell RNA 5' end sequencing. Nat Protoc. Apr. 5, 2012;7(5):813-28. doi: 10.1038/nprot.2012.022.

Jaitin, et al. Massively parallel single-cell RNA-seq for marker-free decomposition of tissues into cell types. Science. Feb. 14, 2014;343(6172):776-9. doi: 10.1126/science.1247651.

Jarosz, M. et al. "Using 1ng of DNA to detect haplotype phasing and gene fusions from whole exome sequencing of cancer cell lines" Cancer Res (2015) 75(suppl5):4742.

Kaper, et al. Supporting Information for "Whole-genome haplotyping by dilution, amplification, and sequencing." Proc Natl Acad Sci U S A. Apr. 2, 2013;110(14):5552-7. doi: 10.1073/pnas.1218696110. Epub Mar. 18, 2013.

Kaper, et al. Whole-genome haplotyping by dilution, amplification, and sequencing. Proc Natl Acad Sci U S A. Apr. 2, 2013;110(14):5552-7. doi: 10.1073/pnas.1218696110. Epub Mar. 18, 2013.

Kenis, et al. Microfabrication Inside Capillaries Using Multiphase Laminar Flow Patterning. Science. 1999; 285:83-85.

Kivioja et al.: Counting absolute numbers of molecules using unique molecular identifiers. Nat Methods. 9(1):72-4 (2011).

Klein, et al. Droplet barcoding for single-cell transcriptomics applied to embryonic stem cells. Cell. May 21, 2015; 161:1187-1201.

Korlach et al., Methods in Enzymology, Real-Time DNA Sequencing from Single Polymerase Molecules, (2010) 472:431-455.

Koster et al., "Drop-based microfluidic devices for encapsulation of single cells", Lab on a Chip The Royal Soc. of Chem. 8: 1110-1115 (2008).

Lafzi, Atefeh et al. Tutorial: guidelines for the experimental design of single-cell RNA sequencing studies. Nature Protocols 13. 12 (2018): 2742-2757.

Lagally, et al. Single-Molecular DNA Amplification and Analysis in an Integrated Microfluidic Device. Anal Chem. Feb. 1, 2001;73(3):565-70.

Laguardia, James J. et al. Prevalence of varicella-zoster virus DNA in dissociated human trigeminal ganglion neurons and nonneuronal cells. Journal of Virology 73.10 (1999): 8571-8577.

Lennon et al. A scalable, fully automated process for construction of sequence-ready barcoded libraries for 454. Genome Biology 11:R15 (2010).

Macosko, et al. Highly Parallel Genome-wide Expression Profiling of Individual Cells Using Nanoliter Droplets. Cell. May 21, 2015;161(5):1202-14. doi: 10.1016/j.cell.2015.05.002.

Madl, et al. "Bioorthogonal Strategies for Engineering Extracellular matrices", Madal, Chritopher, Adv. Funct. Master. Jan. 19, 2018, vol. 28, 1706046, pp. 1-21.

Mair, et al. Injection molded microfluidic chips featuring integrated interconnects. Lab Chip. Oct. 2006;6(10):1346-54. Epub Jul. 31, 2006.

McCoy, R. et al. "Illumina TruSeq Synthetic Long-Reads Empower De Novo Assembly and Resolve Complex, Highly-Repetitive Transposable Elements" PLOS (2014) 9(9):e1016689.

Microfluidic ChipShop. Microfluidic product catalogue. Oct. 2009. 48 pages.

NAVIN. The first five years of single-cell cancer genomics and beyond. Genome Res. Oct. 2015;25(10):1499-507. doi: 10.1101/gr.191098.115.

Nisisako, et al. Droplet formation in a microchannel network. Lab Chip. Feb. 2002;2(1):24-6. Epub Jan. 18, 2002.

Nisisako, T. et al. Droplet Formation in a Microchannel on PMMA Plate. Micro Total Analysis Systems. 2001. Kluwer Academic Publishers. pp. 137-138.

Nisisako, T. et al., Microfluidics large-scale integration on a chip for mass production of monodisperse droplets and particles, The Royal Society of Chemistry: Lab Chip, (Nov. 23, 2007) 8:287-293.

Novak, R. et al., "Single cell multiplex gene detection and sequencing using microfluidically-generated agarose emulsions" Angew. Chem. Int. Ed. Engl. (2011) 50(2):390-395.

Oliver-Calixte, N., et al., "Immobilization of lambda exonuclease onto polymer micropillar arrays for the solid-phase digestion of dsDNAs", Analytical Chemistry 86.9 (2014): 4447-4454.

Orakdogen, N. "Novel responsive poly(N,N-dimethylaminoethyl methacrylate) gel beads: preparation, mechanical properties and pH-dependent swelling behavior" J Polym Res (2012) 19:9914.

Perrott, Jimmy. Optimization and Improvement of Emulsion PCR for the Ion Torrent Next-Generation Sequencing Platform. (2011) Thesis.

Peters, B.A. et al. Accurate whole-genome sequencing and haplotyping from 10 to 20 human cells. Nature, 487(7406): 190-195 (Jul. 2012).

Plunkett, et al. Chymotrypsin responsive hydrogel: application of a disulfide exchange protocol for the preparation of methacrylamide containing peptides. Biomacromolecules. Mar.-Apr. 2005;6(2):632-7.

Priest, et al. Generation of Monodisperse Gel Emulsions in a Microfluidic Device, Applied Physics Letters, 88:024106 (2006).

Pushkarev et al. "Single-molecule sequencing of an individual human genome," Nature Biotech (2009) 27:847-850.

Ramsey, J.M. "The burgeoning power of the shrinking laboratory" Nature Biotech (1999) 17:1061-1062.

Ramskold et al. (2012) "Full-length mRNA-Seq from single-cell levels of RNA and individual circulating tumor cells" Nature Biotechnology 30(8):777-782.

Roche. Using Multiplex Identifier (MID) Adaptors for the GS FLX Titanium Chemistry Basic MID Set Genome Sequencer FLX System, Technical Bulletin 004-2009, (Apr. 1, 2009) pp. 1-11.

(56) References Cited

OTHER PUBLICATIONS

Rotem, A. et al., "High-throughput single-cell labeling (Hi-SCL) for RNA-Seq using drop-based microfluidics" PLOS One (May 22, 2015) 0116328 (14 pages).
Saikia, et al. Simultaneous multiplexed amplicon sequencing and transcriptome profiling in single cells. Nat Methods. Jan. 2019;16(1):59-62. doi: 10.1038/s41592-018-0259-9. Epub Dec. 17, 2018.
Schubert, et al. Microemulsifying fluorinated oils with mixtures of fluorinated and hydrogenated surfactants. Colloids and Surfaces A; Physicochemical and Engineering Aspects, 84(1994) 97-106.
Seiffert, et al. Microfluidic fabrication of smart microgels from macromolecular precursors. Polymer. vol. 51, Issue 25, Nov. 26, 2010, pp. 5883-5889.
Seiffert, S. et al., "Smart microgel capsules from macromolecular precursors" J. Am. Chem. Soc. (2010) 132:6606-6609.
Shah, et al. "Fabrication of mono disperse thermosensitive microgels and gel capsules in micro fluidic devices", Soft Matter, 4:2303-2309 (2008).
Shendure, et al., Accurate Multiplex Polony Sequencing of an Evolved Bacterial Genome. Science 309.5741 (Sep. 2005): 1728-1732. XP002427180, ISSN: 0036-8075, DOI: 10.1126/SCIENCE. 1117839.
Smith, et al. Highly-multiplexed barcode sequencing: an efficient method for parallel analysis of pooled samples. Nucleic Acids Research, 38(13): e142 (2010).
Song, et al. Reactions in droplets in microfluidic channels. Angew Chem Int Ed Engl. Nov. 13, 2006;45(44):7336-56.
Thaxton, C.S. et al. "A Bio-Bar-Code Assay Based Upon Dithiothreitol Oligonucleotide Release" Anal Chem (2005) 77:8174-8178.
Theberge, et al. Microdroplets in microfluidics: an evolving platform for discoveries in chemistry and biology. Angew Chem Int Ed Engl. Aug. 9, 2010;49(34):5846-68. doi: 10.1002/anie.200906653.
Thorsen, et al. Dynamic pattern formation in a vesicle-generating microfluidic device. Physical Review Letters. American Physical Society. 2001; 86(18):4163-4166.
Tonelli, et al. Perfluoropolyether functional oligomers: unusual reactivity in organic chemistry. Journal of fluorine chemistry. 2002; 118(1) 107-121.
Turchinovich, et al. "Capture and Amplification by Tailing and Switching (CATS): An Ultrasensitive Ligation-Independent Method for Generation of DNA Libraries for Deep Sequencing from Picogram Amounts of DNA and RNA." RNA Biology 11.7 (2014): 817-828. PMC. Web. Nov. 13, 2017.
U.S. Appl. No. 16/800,450app, inventor Katherine; Pfeiffer, filed Feb. 25, 2020.
Uttamapinant, et al. Fast, cell-compatible click chemistry with copper-chelating azides for biomolecular labeling. Angew. Chem. Int. End. Engl., Jun. 11, 2012: 51(24) pp. 5852-5856.
Volokitina, M. V., et al., "Polymer monoliths as efficient solid phases for enzymatic polynucleotide degradation followed by fast HPLC analysis", Journal of Separation Science 36.17 (2013): 2793-2805.
Wagner, et al. Biocompatible fluorinated polyglycerols for droplet microfluidics as an alternative to PEG-based copolymer surfactants. Lab Chip. Jan. 7, 2016;16(1):65-9. doi: 10.1039/c5lc00823a. Epub Dec. 2, 2015.
Weigl, et al. Microfluidic Diffusion-Based Separation and Detection. Science. 1999; pp. 346-347.
Williams, et al. Amplification of complex gene libraries by emulsion PCR. Nature Methods. 2006;3(7):545-50.
Zhang, et al. One-step fabrication of supramolecular microcapsules from microfluidic droplets. Science. Feb. 10, 2012;335(6069):690-4. doi: 10.1126/science.1215416.
Zheng, et al. Massively parallel digital transcriptional profiling of single cells. Nat Commun. Jan. 16, 2017;8:14049. doi: 10.1038/ncomms14049.
Zheng, X.Y. et al. "Haplotyping germline and cancer genomes with high-throughput linked-read sequencing" Nature Biotech (Feb. 1, 2016) 34(3):303-311.
Zhu et al., Reverse transcriptase template switching: a SMART approach for full-length cDNA library construction. Biotechniques 30(4):892-7 (2001).
Co-pending U.S. Appl. No. 18/152,650, inventor Shastry; Shankar, filed Jan. 10, 2023.
Co-pending U.S. Appl. No. 18/392,684, inventor Fernandes, Sunjay Jude et al., filed Dec. 21, 2023.
Co-pending U.S. Appl. No. 18/643,684, inventor Bava; Felice Alessio, filed Apr. 23, 2024.
Co-pending U.S. Appl. No. 18/743,583, inventor Nagendran; Monica, filed Jun. 14, 2024.
Co-pending U.S. Appl. No. 18/795,976, inventors Meer; Elliott et al., filed Aug. 6, 2024.
Co-pending U.S. Appl. No. 18/824,258, inventor Stott; Ryan Timothy, filed Sep. 4, 2024.
Co-pending U.S. Appl. No. 18/959,351, inventor Schnalll-Levin; Michael, filed Nov. 25, 2024.
Co-pending U.S. Appl. No. 19/044,383, inventors Smibert; Peter et al., filed Feb. 3, 2025.
Co-pending U.S. Appl. No. 19/093,986, inventors Smibert; Bloju; Octavian Marian et al., filed Mar. 28, 2025.

* cited by examiner

METHODS, KITS, AND COMPOSITIONS FOR PROCESSING EXTRACELLULAR MOLECULES

CROSS-REFERENCE

This application is a continuation of U.S. application Ser. No. 17/318,364, filed May 12, 2021, which claims the benefit of U.S. Provisional Patent Application No. 63/042,106, filed Jun. 22, 2020, and U.S. Provisional Patent Application No. 63/024,042, filed May 13, 2020, each of which is incorporated herein by reference in its entirety for all purposes.

BACKGROUND

A sample may be processed for various purposes, such as identification of a type of moiety within the sample. The sample may be a biological sample. Biological samples may contain biological particles (e.g., cells and/or nuclei), and may be processed to detect analytes from or in the cells and/or nuclei. Such detection may provide, for example, for diagnosis of diseases (e.g., cancer).

Methods and systems have been developed to process single biological particles. In some examples, partitions may be used to in these methods and systems. Partitions may be wells or droplets. Droplets or wells may be employed to process biological samples in a manner that enables the biological samples to be partitioned and processed separately. For example, such droplets may be fluidically isolated from other droplets, enabling accurate control of respective environments in the droplets. Partition-based systems for processing of samples of single cells and/or nuclei can result in identification of hundreds to thousands of analytes from each of hundreds to tens of thousands of cells in a population. The particles (e.g., cells and/or nuclei) contained in biological samples.

Single-cell analysis methods and systems may provide optimum results if the biological particles input into the methods and systems meet certain specifications. The ability to improve the results produced by single-cell systems, in some examples by improving the cells/nuclei input into the systems, is an active area of research and development in the field.

SUMMARY

In some aspects, disclosed are methods, kits, and compositions for processing a sample such as a biological sample. In some cases, disclosed herein is processing and analyzing the genetic material of biological particles (e.g., cells or cell nuclei) in the sample, for example analyzing nucleic acid molecules in a plurality of cells or cell nuclei in a sample. In some cases, extracellular molecules, such as extracellular biological molecules, e.g., extracellular nucleic acid molecules, may exist in a sample comprising biological particles, such as cells and/or cell nuclei. For example, the extracellular biological molecules, e.g., extracellular nucleic acid molecules, in the sample may be released from cell nuclei during cell growth and/or sample processing, such as, during the early stages of sample preparation as a result of cell lysis or for other reasons. Extracellular molecules (e.g., extracellular biological molecules, such as extracellular nucleic molecules) in a sample comprising a cell or a cell nucleus may also be referred to as ambient molecules, free-floating molecules, or background molecules (e.g., ambient or background nucleic acid molecules). The presence of extracellular molecules (e.g., ambient or free-floating nucleic acid molecules) may cause problems, complications, or inaccuracies during sample processing and/or analysis. For example, when the goal is to analyze the nucleic acid molecules in the cells or cell nuclei in a biological sample, the presence of extracellular nucleic acid molecules may create noise in the data and complicate data analysis. Moreover, the presence of extracellular nucleic acid molecule may hinder a proper clustering of the cells or cell nuclei of the sample in terms of a parameter which is under investigation, such as the presence of a marker or other information in or related to the genetic material of the cells, such as the presence of a marker. In some examples, extracellular molecules, e.g., extracellular biological molecules like extracellular nucleic acid molecules, may cause cells and/or nuclei to form multiple-cell clusters, clumps or aggregates. In some instances, like in the case of methods for analyzing single individual cells, these clusters, clumps or aggregates may not be desirable.

Recognized herein is a need for methods for decreasing or substantially eliminating the presence of extracellular or ambient molecules (e.g., extracellular biological molecules, such as extracellular nucleic acid molecules) in a sample comprising a cell or cell nucleus, and compositions comprising a cell and/or cell nucleus that contain small amounts of extracellular nucleic acid molecules or are substantially free of them.

In some examples, the disclosed methods may reduce the size of cell aggregates in a sample by treating the aggregates with a reagent that acts to de-aggregate cells and reduce the size of cell aggregates. In the exemplary methods, the de-aggregating reagent may be attached to a support and, after processing of the cells by the reagent, the support and the attached reagent are removed from the cells, leaving the de-aggregated cells. In some examples, the de-aggregated cells may subsequently be used in single cell-based systems, where presence of the de-aggregating reagent would be harmful to subsequent system steps. An example single cell-based system in which the de-aggregated cells may be used is a system that generates single, de-aggregated cells in discrete partitions, e.g., a droplet in an emulsion or a well. The workflow of this system includes subsequent steps to identify and catalog multiple analytes from a large number of discrete partitions that contain single cells to develop single-cell analyte profiles of cell populations.

In an aspect, the present disclosure provides a method for processing a sample that comprises a cell or cell nucleus, the method comprising bringing the sample in contact with a support to yield a processed sample. The support may comprise a catalyst (e.g., an enzyme) attached thereto, and the catalyst may be configured to degrade an extracellular nucleic acid in the sample.

Herein, a biological particle and a catalyst that is attached to a support to yield a processed biological particle is disclosed. The biological particle may contain multiple components which, in some examples are multiple cells and/or nuclei in an aggregate or clump. In some examples, the aggregated cells and/or nuclei may be peripheral blood mononuclear cells (PBMCs). In some examples, the cell aggregates may contain substances that promote cell aggregation or clumping. In some examples, the substance promoting cell aggregation may be extracellular nucleic acids, like DNA and/or RNA. In some examples, the catalyst may be an enzyme. In some examples, the enzyme may be a nuclease attached to a support. The nuclease may be a DNase. The support may be a bead. Processing of the nucleic acid in the cell aggregates by the nuclease may result in de-aggregation of the aggregated cells. Removal of the support from the system, for example, using electromagnetic, electromotive, magnetic and/or mechanical forces, yields single cells in which the nuclease attached to the support is not present.

In some embodiments, the catalyst includes an enzyme. The enzyme may be a hydrolase, a nuclease, a ribonuclease, an exonuclease, a restriction enzyme, a protease, or any combination thereof. In some embodiments, the enzyme comprises at least one of ribonuclease and exonuclease. In some embodiments, the extracellular nucleic acid molecule comprises ribonucleic acid (RNA) or deoxyribonucleic acid (DNA). In some embodiments, the extracellular nucleic acid comprises at least one of messenger RNA (mRNA), chromosome, and genomic DNA (gDNA). In some embodiments, the enzyme is coupled to the support during or subsequent to degradation of the extracellular nucleic acid molecule.

In some embodiments, the catalyst is immobilized on a surface of the support. In some embodiments, the enzyme is immobilized on a surface of the support by an affinity-tag, entrapment, linkage, cross-linkage, covalent bond, or any combination thereof. In some embodiments, the support comprises a surface moiety or linker configured to bind the enzyme. In some embodiments, the support is configured to be impenetrable to the cell and said cell nucleus. In some embodiments, the support is configured to be inert to cellular metabolism and intracellular activities. In some embodiments, the support is configured to maintain the viability of the cell. In some embodiments, the support is separable from the cell and the cell nucleus.

In some embodiments, the support is separable from said cell and said cell nucleus. In some embodiments, the support is insoluble in the sample. In some embodiments, the support is a sphere with a diameter of at least about 1 micrometer (μm) in size. In some embodiments, the diameter is between about 1 micrometer (μm) to 20 micrometers (μm). In some embodiments, the diameter is between about 5 micrometers (μm) to 10 micrometers (μm). In some embodiments, the support is a magnetic support configured to be separated from the sample using a magnetic or electromagnetic force. In some embodiments, the support comprises a bead, resin, tube wall, pipette tip, column surface, micropillar, or any combination thereof. In some embodiments, the support is a bead. In some embodiments, the bead is a solid bead or a gel bead. In some embodiments, the bead is a magnetic bead. In some embodiments, the bead is a gel bead comprising magnetic particles. In some embodiments, the bead is a solid magnetic microsphere.

In some embodiments, the support may not comprise an enzyme. In some embodiments, the support may not degrade an extracellular molecule. In some embodiments, the support may comprise a coating. In some embodiments, the coated support may be configured to capture the extracellular molecule, e.g., binding or attaching to the extracellular molecule. In some embodiments, the coated support bound to the extracellular molecule may be separated from the sample, thereby separating the extracellular molecule from the sample. In some embodiments, the coating may comprise a chemical or a biological molecule or particle, which interacts with the extracellular molecule. In some embodiments, the coating or coated support may comprise a poly-t chain, a virus DNA, an ssDNA, an aptamer, or combinations thereof. In some embodiments, the support comprising a coating may bind the extracellular molecule and be separated from the sample, thereby separating the extracellular molecule from the sample. In some embodiments, the support is a bead, e.g., a magnetic bead.

In some embodiments, the support may be insoluble in the sample. In some embodiments, the support is a sphere with a diameter of at least about 1 micrometer (μm) in size. In some embodiments, the diameter is between about 1 micrometer (μm) to 20 micrometers (μm). In some embodiments, the diameter is from about 5 micrometers (μm) to 10 micrometers (μm).

In some embodiments, the support may be magnetic. In some embodiments, the method may further comprise separating the support from the sample using a magnetic or electromagnetic force. In some embodiments, the support may be a bead, polymeric matrix, tube wall, pipette tip, column surface, micropillar, an array, a well, or any combination thereof. In some embodiments, the support is a bead. In some embodiments, the bead is a solid bead or a gel bead. In some embodiments, the bead is a magnetic bead. In some embodiments, the bead is a gel bead comprising magnetic particles. In some embodiments, the bead is a solid magnetic microsphere.

In some embodiments, the enzyme comprises exonuclease I (ExoI). In some embodiments, the enzyme is a hydrolase, a nuclease, a ribonuclease, an exonuclease, a restriction enzyme, a protease, or any combination thereof. In some embodiments, the enzyme comprises at least one of ribonuclease and exonuclease.

In some embodiments, the extracellular nucleic acid comprises ribonucleic acid (RNA) or deoxyribonucleic acid (DNA). In some embodiments, the extracellular nucleic acid comprises at least one of messenger RNA (mRNA), chromosome, and genomic DNA (gDNA).

In some embodiments, the enzyme is coupled to the support during or subsequent to degradation of said extracellular nucleic acid.

In some embodiments, the method further comprises separating the support from the processed sample. In some embodiments, the method further comprises partitioning the processed sample in a partition. In some embodiments, the partition is a microwell. In some embodiments, the partition is a droplet. In some embodiments, the droplet is generated using a microfluidic device. In some embodiments, the droplet is generated at least in part by (i) providing a mixture comprising (1) a first phase comprising said processed sample and (2) a second phase immiscible with said first phase, and (ii) subjecting said mixture to agitation. In some embodiments, the first phase is an aqueous phase or said second phase is an oil phase. In some embodiments, the agitation comprises vortexing. In some embodiments, the sample is a suspension.

Also disclosed are compositions. A composition may include a biological particle, containing clumped cells in some examples, and a catalyst attached to a support. A composition may include a discrete droplet that partitions a processed biological particle (e.g., a de-aggregated single cell) from other processed biological particles.

In an aspect, the present disclosure provides a composition comprising a cell or cell nucleus and an extracellular nucleic acid molecule fragment. The nucleic acid molecule fragment may be smaller than: 50 base pairs (bp), 40 bp, 30 bp, 20 bp, or 10 bp in size, e.g., 10-20 bp/nt or less, and the composition may be substantially free of an extracellular nucleic acid molecule larger than about 60 base pairs (bp) in size. In some embodiments, the composition is provided in a partition. In some embodiments, the partition is a droplet or a microwell. In some embodiments, the composition further comprises (i) a first phase comprising the cell or cell nucleus and (ii) a second phase immiscible with the first phase. In some embodiments, the first phase is an aqueous phase and/or the second phase is an oil phase. In some embodiments, the composition is a suspension.

Also disclosed are kits. A kit may include a catalyst attached to a support and a device or component configured to remove the support and attached catalyst from a sample containing cells. The kit may include a support. The support may comprise an enzyme attached thereto. The enzyme may be configured to degrade an extracellular nucleic acid. The kit may further comprise printed instructions for bringing a sample comprising a cell or a cell nucleus in contact with the support, to degrade an extracellular nucleic acid in the sample to yield a processed sample. In some embodiments, the enzyme is immobilized on a surface of the support.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

The following U.S. patents and U.S. published patent applications are each incorporated by reference in their entirety into this application:
  U.S. Pat. No. 9,644,204 (Ser. No. 14/175,935), issued May 9, 2017 and titled, "Partitioning and Processing of Analytes and Other Species";
  U.S. Pat. No. 9,975,122 (Ser. No. 14/934,044), issued May 22, 2018 and titled, "Instrument Systems for Integrated Sample Processing";
  U.S. Pat. No. 10,053,723 (Ser. No. 15/719,459), issued Aug. 21, 2018 and titled, "Capsule Array Devices and Methods of Use"; and
  U.S. Pat. No. 10,071,377 (Ser. No. 15/687,856), issued Sep. 11, 2018 and titled, "Fluidic Devices, Systems, And Methods for Encapsulating and Partitioning Reagents, And Applications of Same."

Other references incorporated by reference may be listed throughout the application.

BRIEF DESCRIPTION OF THE DRAWINGS

In the accompanying drawings, which are incorporated in and constitute a part of the specification, embodiments of the disclosed inventions are illustrated. It will be appreciated that the embodiments illustrated in the drawings are shown for purposes of illustration and not for limitation. It will be appreciated that changes, modifications and deviations from the embodiments illustrated in the drawings may be made without departing from the spirit and scope of the invention, as disclosed below.

DETAILED DESCRIPTION

Figure 1:
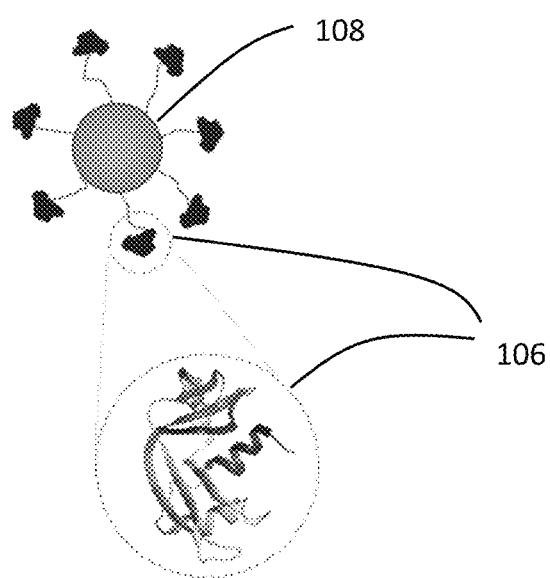
FIG. 1 shows an example of a support with catalysts (e.g., enzymes) attached thereto which may be used for performing the methods provided herein.

Provided herein are methods for processing a sample that may comprise particles, including biological particles. In some examples, the biological particles may be a cell and/or a cell nucleus. The methods are generally applicable to processing of particles with a catalyst on a support and removing the support and attached catalyst to leave processed particles. In some examples, the particles that are processed using the methods are made up of one or more components. In some examples, the processing is designed to break-up the components of the particle into individual components.

In some examples, provided herein are methods for processing samples that comprise a cell or cell nucleus. The methods may comprise providing a support that may be configured to bind an extracellular molecule (e.g., extracellular nucleic acid molecule) in the sample. The methods may comprise bringing the sample in contact with the support to yield a processed sample or a composition. For example, an extracellular molecule may attach to or bind the support. The support may be separated from the sample, thereby separating the extracellular molecule from the sample.

In some examples, provided herein are methods for processing samples that comprise a cell or cell nucleus. The methods may comprise providing a support that may comprise a catalyst that includes one or more enzymes. The enzymes may be configured to degrade or digest an extracellular molecule (e.g., extracellular nucleic acid molecule) in the sample. The method may comprise bringing the sample in contact with the support to yield a processed sample or a composition. In some examples, the support may not comprise an enzyme. The support may be configured to or capable of binding the extracellular molecule. Separating the support (e.g., a support that does not comprise an enzyme) may facilitate separating the extracellular molecule from the sample, for example, without digesting the extracellular molecule.

The methods may include analyzing the particles (e.g., cells and/or nuclei) that have been processed by the above methods. For example, analyzing genomic information from the cells and/or cell nuclei, such as analyzing the intracellular nucleic acid molecules inside the cells and/or cell nuclei. In some examples, the methods may comprise performing single cell analysis of the cells and/or cell nuclei of the sample and clustering the cells and/or cell nuclei in terms of a parameter or characteristic under investigation, for example a marker (e.g., a marker related to a biological condition of a sample or a subject). The methods may comprise partitioning the sample in a plurality of partitions such as droplets and/or wells.

Definitions

Unless defined otherwise, all technical and scientific terms used herein have the same meaning as commonly understood by one of ordinary skill in the art to which the present invention pertains. It is to be understood that the terminology used herein is for describing particular embodiments only and is not intended to be limiting. For purposes of interpreting this disclosure, the following description of terms will apply and, where appropriate, a term used in the singular form will also include the plural form and vice versa.

The terms "a," "an," and "the," as used herein, generally refers to singular and plural references unless the context clearly dictates otherwise.

Whenever the term "at least," "greater than," or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "no more than," "less than," or "less than or equal to" precedes the first numerical value in a series of two or more numerical values, the term "no more than," "less than," or "less than or equal to" applies to each of the numerical values in that series of numerical values. For example, less than or equal to 3, 2, or 1 is equivalent to less than or equal to 3, less than or equal to 2, or less than or equal to 1.

Herein, "activity," when referring to an enzyme, means the amount of, or extent to which, an enzyme catalyzes a reaction.

The terms "adaptor(s)", "adapter(s)" and "tag(s)" may be used synonymously. An adaptor or tag can be coupled to a polynucleotide sequence to be "tagged" by any approach, including ligation, hybridization, or other approaches.

Herein, "agitate" generally means to move or force violently. Herein, "agitate" may be used to describe a force applied to a continuously flowing liquid to result in droplet formation. "Agitation" is the process of moving or forcing violently.

Herein, "aggregate" when used as a noun, or "aggregation," refers to a compacted or associated mass of individual components. Herein, aggregate may be used to refer to a mass of individual cells and/or nuclei, for example. "Aggregating" refers to the act of forming an aggregate.

Herein, "anchorage-independent" generally refers to cells that can grow, divide or remain viable without a surface to attach to or anchor on.

Herein, "attach" generally refers to a relationship between separate objects based on forces that link the separate objects. In some examples, two objects may attach to one another because of a covalent bond between the two objects. In some examples, attachment between two objects may not be reversible.

Herein, "barcode," generally refers to a label, or identifier, that conveys or is capable of conveying information about an analyte. A barcode can be part of an analyte. A barcode can be independent of an analyte. A barcode can be a tag attached to an analyte (e.g., nucleic acid molecule) or a combination of the tag in addition to an endogenous characteristic of the analyte (e.g., size of the analyte or end sequence(s)). A barcode may be unique. Barcodes can have a variety of different formats. For example, barcodes can include polynucleotide barcodes; random nucleic acid and/or amino acid sequences; and synthetic nucleic acid and/or amino acid sequences. A barcode can be attached to an analyte in a reversible or irreversible manner. A barcode can be added to, for example, a fragment of a deoxyribonucleic acid (DNA) or ribonucleic acid (RNA) sample before, during, and/or after sequencing of the sample. Barcodes can allow for identification and/or quantification of individual sequencing-reads.

As used herein, the term "barcoded nucleic acid molecule" generally refers to a nucleic acid molecule that results from, for example, the processing of a nucleic acid barcode molecule with a nucleic acid sequence (e.g., nucleic acid sequence complementary to a nucleic acid primer sequence encompassed by the nucleic acid barcode molecule). The nucleic acid sequence may be a targeted sequence or a non-targeted sequence. For example, in the methods and systems described herein, hybridization and reverse transcription of a nucleic acid molecule (e.g., a messenger RNA (mRNA) molecule) of a cell with a nucleic acid barcode molecule (e.g., a nucleic acid barcode molecule containing a barcode sequence and a nucleic acid primer sequence complementary to a nucleic acid sequence of the mRNA molecule) results in a barcoded nucleic acid molecule that has a sequence corresponding to the nucleic acid sequence of the mRNA and the barcode sequence (or a reverse complement thereof). A barcoded nucleic acid molecule may serve as a template, such as a template polynucleotide, that can be further processed (e.g., amplified) and sequenced to obtain the target nucleic acid sequence. For example, in the methods and systems described herein, a barcoded nucleic acid molecule may be further processed (e.g., amplified) and sequenced to obtain the nucleic acid sequence of the mRNA.

Herein, "bead," generally refers to a particle. The bead may be a solid or semi-solid particle. The bead may be a gel bead. The gel bead may include a polymer matrix (e.g., matrix formed by polymerization or cross-linking). The polymer matrix may include one or more polymers (e.g., polymers having different functional groups or repeat units). Polymers in the polymer matrix may be randomly arranged, such as in random copolymers, and/or have ordered structures, such as in block copolymers. Cross-linking can be via covalent, ionic, or inductive, interactions, or physical entanglement. The bead may be a macromolecule. The bead may be formed of nucleic acid molecules bound together. The bead may be formed via covalent or non-covalent assembly of molecules (e.g., macromolecules), such as monomers or polymers. Such polymers or monomers may be natural or synthetic. Such polymers or monomers may be or include, for example, nucleic acid molecules (e.g., DNA or RNA). The bead may be formed of a polymeric material. The bead may be magnetic or non-magnetic. The bead may be rigid. The bead may be flexible and/or compressible. The bead may be disruptable or dissolvable. The bead may be a solid particle (e.g., a metal-based particle including but not limited to iron oxide, gold or silver) covered with a coating comprising one or more polymers. Such coating may be disruptable or dissolvable. A bead may be porous, non-porous, hollow (e.g., a microcapsule), solid, semi-solid, and/or a combination thereof. Alternatively, or in addition, a bead may be solid, semi-solid, semi-fluidic, fluidic, and/or a combination thereof. A bead is a type of support.

Herein, "bind" generally refers to a relationship between separate objects based on forces that the separate objects can exert on one another. In some examples, two objects may bind one another because of affinity binding or ionic binding. In some examples, binding is specific, as when a receptor. In some examples, binding between two objects may be reversible, or even in an equilibrium.

The term "biological particle," as used herein, generally refers to a discrete biological system derived from a biological sample. The biological particle may be a macromolecule, small molecule, virus, cell, cell derivative, cell nucleus, cell organelle, cell constituent and the like. The biological particle may contain multiple individual components, such as macromolecules, small molecules, viruses, cells, cell derivatives, cell nuclei, cell organelles and cell constituents, including combinations of different of these and other components. The biological particle may be or may include DNA, RNA, organelles, proteins, or any combination thereof. These components may be extracellular. In some examples, the biological particle may be referred to as a clump or aggregate of combinations of components. In some instances, the biological particle may include one or more constituents of a cell but may not include other constituents of the cell. An example of such constituents include nucleus or an organelle. A cell may be a live or viable cell. The live cell may be capable of being cultured, for example, being cultured when enclosed in a gel or polymer matrix or cultured when comprising a gel or polymer matrix. A biological particle may be a membrane-bound particle.

Herein, "capable" means having the ability or quality to do something.

Herein, "catalyst" refers to a substance that increases the rate of a reaction, generally without undergoing permanent chemical change. Biological catalyst refers to a catalyst that includes one or more biomolecules, like proteins or RNA. One type of biological catalyst is an enzyme.

Herein, "clump," when used as a noun, refers to a close group or cluster of individual components. Herein, "clump may be used to refer to a close group or cluster of individual cells and/or nuclei, for example. Herein, "clumping" refers to the act of forming a clump.

Herein, "component" refers to a part of element of a larger whole. Herein, a component may be used to refer to individual parts of an aggregate or clump. Herein, components of an aggregate or clump may include cells or cell organelles (e.g., nucleus).

Herein, "configured to" generally refers to, for example, a component of a system that can perform a certain function.

Herein, "contact" refers to physical touching of separate substances or objects. "Contacting" refers to causing separate substances to physically touch one another.

Herein, "cryopreserve" means preserving cells and/or tissues by cooling them below the freezing point of water (e.g., freezing).

Herein, "deoxyribonucleic acid" or "DNA" refers to a nucleic acid formed from polymerization of deoxyribonucleotides.

Herein, "discrete" means separate or individual.

Herein, "droplet" refers to a small portion of a liquid, generally round or pear-shaped.

Herein, "encapsulate" means to enclose in something.

Herein, "enzyme" refers to a protein or proteins that increase the rate of a reaction, converting substrate into product. Generally, an enzyme is a type of biological catalyst.

Herein, "extracellular" means outside of or partially outside of a cell (e.g., not completely encompassed by an uninterrupted cell membrane). In some examples, a sample that contains cells may also contain extracellular nucleic acids. In some examples, the extracellular nucleic acids may have been released from cells in the sample. In some examples, some cells in the sample may have lost viability and may release nucleic acids. In some examples, extracellular nucleic acids may be attached to cell membranes or debris from the cells that released the nucleic acids.

Herein, "force" refers to an interaction that, when unopposed, will cause or change the position or movement of an object.

The term "genome," as used herein, generally refers to genomic information from a subject, which may be, for example, at least a portion or an entirety of a subject's hereditary information. A genome can be encoded either in DNA or in RNA. A genome can comprise coding regions (e.g., that code for proteins) as well as non-coding regions. A genome can include the sequence of all chromosomes together in an organism. For example, the human genome ordinarily has a total of 46 chromosomes. The sequence of all of these together may constitute a human genome.

Herein, "immobile" means not moving or motionless. "Immobilize" refers to an act to make something immobile.

Herein, "inert" means inactive; chemically inactive.

Herein, "instructions" refers to information stating how something should be done.

Herein, "library" generally refers to a collection of nucleic acid (e.g., DNA) fragments, generally representative of the nucleic acid sequences of the molecule or molecules (e.g., genome) from which the library is made.

The term "macromolecular constituent," as used herein, generally refers to a macromolecule contained within or from a biological particle. The macromolecular constituent may comprise a nucleic acid. In some cases, the biological particle may be a macromolecule. The macromolecular constituent may comprise DNA. The macromolecular constituent may comprise RNA. The RNA may be coding or non-coding. The RNA may be messenger RNA (mRNA), ribosomal RNA (rRNA) or transfer RNA (tRNA), for example. The RNA may be a transcript. The RNA may be small RNA that are less than 200 nucleic acid bases in length, or large RNA that are greater than 200 nucleic acid bases in length. Small RNAs may include 5.8S ribosomal RNA (rRNA), 5S rRNA, transfer RNA (tRNA), microRNA (miRNA), small interfering RNA (siRNA), small nucleolar RNA (snoRNAs), Piwi-interacting RNA (piRNA), tRNA-derived small RNA (tsRNA) and small rDNA-derived RNA (srRNA). The RNA may be double-stranded RNA or single-stranded RNA. The RNA may be circular RNA. The macromolecular constituent may comprise a protein. The macromolecular constituent may comprise a peptide. The macromolecular constituent may comprise a polypeptide.

Herein, "mixture" refers to a combination of multiple chemical substances that have not reacted with one another.

The term "molecular tag," as used herein, generally refers to a molecule capable of binding to a macromolecular constituent. The molecular tag may bind to the macromolecular constituent with high affinity. The molecular tag may bind to the macromolecular constituent with high specificity. The molecular tag may comprise a nucleotide sequence. The molecular tag may comprise a nucleic acid sequence. The nucleic acid sequence may be at least a portion or an entirety of the molecular tag. The molecular tag may be a nucleic acid molecule or may be part of a nucleic acid molecule. The molecular tag may be an oligonucleotide or a polypeptide. The molecular tag may comprise a DNA aptamer. The molecular tag may be or comprise a primer. The molecular tag may be, or comprise, a protein. The molecular tag may comprise a polypeptide. The molecular tag may be a barcode.

Herein, "nuclease" refers to a substance, generally an enzyme, that cleaves bonds between nucleotides in nucleic acids to form smaller units. (e.g., individual nucleotides). Nucleases that cleave DNA are generally called deoxyribonucleases (DNases). Nucleases that cleave RNA are generally called ribonucleases (RNases). A nuclease that cleaves a nucleic acid at its ends is generally called an exonuclease. A nuclease that cleaves a nucleic acid between its ends is generally called an endonuclease.

Herein, "nucleic acid" refers to linear macromolecules formed from polymerization of units called nucleotides.

Herein, "nucleus" means an organelle in a eukaryotic cell that contains a genome.

Herein, "originate" refers to where something came from; the starting material.

Herein, "partition" generally, refers to a space or volume that may be suitable to contain one or more species or conduct one or more reactions or processes. A partition may be a physical compartment, such as a droplet or well (e.g., a microwell). The partition may isolate space or volume from another space or volume. The droplet may be a first phase (e.g., aqueous phase) in a second phase (e.g., oil) immiscible with the first phase. The droplet may be a first phase in a second phase that does not phase separate from the first phase, such as, for example, a capsule or liposome in an aqueous phase. A partition may comprise one or more other (inner) partitions. In some cases, a partition may be a virtual compartment that can be defined and identified by an index (e.g., indexed libraries) across multiple and/or remote physical compartments. For example, a physical compartment may comprise a plurality of virtual compartments.

Herein, "penetrate" means able to get into or through, or to force into or through something. A structure (e.g., a cell) that is impenetrable to something (e.g., a support) means that the thing being referred to cannot or is not able to get into the structure. Likewise, a support may be said to be impenetrable to a cell.

Herein, "peripheral blood mononuclear cells" or "PBMCs" are peripheral blood cells having a round nucleus. These cells include lymphocytes (T cells and B cells), monocytes, NK cells and stem cells.

Herein, "permeable" refers to the state of a cell such that analytes can flow out of the cell. "Permeabilize" refers to causing cells to be permeable. In some examples, permeabilization of cells involves affecting the structure of cell membranes such that analytes can diffuse out from the cells. In some examples, mild detergents may be used to permeabilize cells.

Herein, "physical characteristics" may include, but not be limited to, things like charge, density, size and the like.

Herein, "primer" means a single-stranded nucleic acid sequence that provides a starting point for DNA synthesis. Generally, a primer has a nucleotide sequence that is complementary to a template, and has an available 3'-hydroxyl group to which a transcriptase or polymerase can add additional nucleotides complementary to corresponding nucleotides in the template, to synthesize a nucleic acid strand in the 3' to 5' direction.

Herein, "process," when used herein as a verb, refers to performing one or more operations on a thing, for example, to change the thing.

Herein, "processed biological particle" generally refers to a biological particle that has been changed by contact with a catalyst.

Herein, "promote" means to favor, cause or further the progress of something.

Herein, "provide" means to make available. Providing is the act of making something available.

The term "real time," as used herein, can refer to a response time of less than about 1 second, a tenth of a second, a hundredth of a second, a millisecond, or less. The response time may be greater than 1 second. In some instances, real time can refer to simultaneous or substantially simultaneous processing, detection or identification.

Herein, "remove" means to eliminate or get rid of something.

Herein, "sample" generally refers to a collection of something. In some examples, "sample" may refer to a collection of biological particles, which may contain additional molecules or substances. In some examples, a "sample" may refer to a collection of processed biological particles, which may contain additional molecules or substances. In some examples, a biological sample may comprise any number of macromolecules, for example, cellular macromolecules. The sample may be a cell sample. The sample may be a cell line or cell culture sample. The sample can include one or more cells, or one or more cell aggregates or clusters. The sample may include nuclei from cells. The biological sample may be derived from another sample. The sample may be a tissue sample, such as a biopsy, core biopsy, needle aspirate, or fine needle aspirate. The sample may be a fluid sample, such as a blood sample, urine sample, or saliva sample. The sample may be a skin sample. The sample may be a cheek swab. The sample may be a plasma or serum sample. The sample may be a blood sample. The sample may contain PBMCs.

Herein, "separate," when used as a verb, generally refers to causing something to move away from or to be apart from something else. "Separating" refers to the act of making something separate. "Separated" refers to something that is separate from something else.

The term "sequencing," as used herein, generally refers to methods and technologies for determining the sequence of nucleotide bases in one or more polynucleotides. The polynucleotides can be, for example, nucleic acid molecules such as deoxyribonucleic acid (DNA) or ribonucleic acid (RNA), including variants or derivatives thereof (e.g., single stranded DNA). Sequencing can be performed by various systems currently available, such as, without limitation, a sequencing system by Illumina®, Pacific Biosciences (PacBio®), Oxford Nanopore®, or Life Technologies (Ion Torrent®). Alternatively, or in addition, sequencing may be performed using nucleic acid amplification, polymerase chain reaction (PCR) (e.g., digital PCR, quantitative PCR, or real time PCR), or isothermal amplification. Such systems may provide a plurality of raw genetic data corresponding to the genetic information of a subject (e.g., human), as generated by the systems from a sample provided by the subject. In some examples, such systems provide sequencing reads (also "reads" herein). A read may include a string of nucleic acid bases corresponding to a sequence of a nucleic acid molecule that has been sequenced. In some situations, systems and methods provided herein may be used with proteomic information.

Herein, "single cell" or "single nucleus" generally refers to a cell or a nucleus that is not present in an aggregate or clump. Single cells/nuclei generally are desired for use in partitioning cells to perform cell profiling, like that which is done using single-cell based systems.

The term "subject," as used herein, generally refers to an animal, such as a mammal (e.g., human) or avian (e.g., bird), or other organism, such as a plant. For example, the subject can be a vertebrate, a mammal, a rodent (e.g., a mouse), a primate, a simian or a human. Animals may include, but are not limited to, farm animals, sport animals, and pets. A subject can be a healthy or asymptomatic individual, an individual that has or is suspected of having a disease (e.g., cancer) or a pre-disposition to the disease, and/or an individual that is in need of therapy or suspected of needing therapy. A subject can be a patient. A subject can be a microorganism or microbe (e.g., bacteria, fungi, archaea, viruses).

Herein, "subsequent to" means after.

Herein, "substance" generally refers to a particular kind of matter that may have uniform properties. Herein, a substance may refer to something that promotes aggregation or clumping of components in a biological particle.

Herein, "substrate" refers to the molecule or molecules on which an enzyme acts.

Herein, "support," when used as a noun, refers to something that serves, for example, as a foundation, prop, brace or stay for another thing. In some examples, the support may be larger, more easily worked with, or more easily tracked or visualized than the thing being supported. In some examples herein, a bead may be a support for a catalyst or enzyme. A support may be a solid support. In some instances, a support (e.g., a bead) may be dissolvable, disruptable, and/or degradable. In some cases, a support (e.g., a bead) may not be degradable. In some cases, the support (e.g., a bead) may be a gel bead. A gel bead may be a hydrogel bead. A gel bead may be formed from molecular precursors, such as a polymeric or monomeric species. A semi-solid support (e.g., a bead) may be a liposomal bead. A support may comprise one or more metals, such as iron oxide, gold, and silver, or other metal. A support may be magnetic. For example, a support may comprise a magnetic material. In some cases, the support (e.g., a bead) may be a silica bead. In some cases, the support (e.g., a bead) can be rigid. In other cases, the support (e.g., a bead) may be flexible and/or compressible.

Herein, "surface" generally refers to the outside or outer layer of something.

Herein, "suspension" generally refers to particles in a liquid, where the particles will settle on standing. Generally, cells within a liquid (e.g., a liquid buffer) are considered a suspension.

Herein, "template" refers to one single-stranded nucleic acid acting as a "template" for synthesis of another complementary single-stranded nucleic acid. For example, RNA can act as a template for synthesis of a complementary DNA strand synthesized using reverse transcriptase. A single-stranded DNA can act as a template for synthesis of a complementary DNA strand, most often by a DNA polymerase.

Herein, "thaw" means to become liquid as a result of warming (e.g., melting).

Herein, "yield" means produce.

Herein, "viable" means alive. Generally, "viability" refers to the extent to which a population of cells is viable.

Biological Particles, Cells, Nuclei

The methods disclosed here are generally applicable to processing of particles with a catalyst on a support and removing the support and attached catalyst to leave processed particles. In some examples, the particles that are processed using the methods are made up of one or more components. In some examples, the processing is designed to break-up the components of the particle into individual components.

In some examples, the methods disclosed here are designed to process biological particles. In some examples, the biological particles may contain multiple components (e.g., cells, nuclei) which may be identical, similar or dissimilar. In some examples, the processing is designed to de-aggregate or de-clump the biological particles into their single components. In some examples, the processing is designed to break-up clumps of cells and/or nuclei into un-clumped, individual cells and/or nuclei.

In some examples, biological particles may be cells, parts of cells or cell organelles, like a cell nucleus. Cells may be of any kind or type. A cell may be a mammalian cell. A cell may be a eukaryotic cell or a prokaryotic cell. A cell may be an animal cell. A cell may be a human cell. A cell may be from a cell culture. A cell may be from an immortalized cell line. A cell may be from a primary sample, such as a patient sample. A cell may be from a frozen stock of cells (e.g., cryopreserved cells). The cells may be adherent cells or suspension cells. An adherent cell may be adhered to a surface. Alternatively, an adherent cell may be treated (e.g., with a chemical or biological reagent) to be separated from the surface, and thereby may be suspended in a sample.

Examples of cells may comprise a plant cell, animal cell, human cell, insect-derived cells, bacteria, algae, cardiomyocytes, stem cells, neurons, primary neurons, ESCs, iPSCs, hepatocytes, primary heart valve cells, primary hematopoietic cells, gastrointestinal cells, lymphocytes, T-cells, B-cells, natural killer cells, dendritic cells, hematopoietic cells, beta cells, somatic cells, germ cells, embryos (human and animal), zygotes, gametes, and other types of cells. In some examples, a cell may be a therapeutic cell. For example, the cell may be suspected of having a therapeutic effect. The cell may be a stem cell.

In some instances, a cell may be a cancer cell. A cell may be from an immortalized cancer cell line. A cell may be a HeLa cell. A cell may be a breast cancer cell, a multiple myeloma cell, a lymphoma cell, or any other kid of cell. In some examples, different kinds of cells may be co-cultured and/or otherwise combined.

Nonlimiting examples of cells may comprise 1205 Lu, 1321 N1, 143B, 22Rv1, 23132/87, 293, 293 (suspension), 293-F, 293T, 2A8, 2PK3, 300.19, 32D, 3A9, 3T3-L1 ad, 3T3-L1 pre-ad, 3T3-Swiss albino, 4T1, 5838 Ewing's, 661 W, 697, 7-17, 720, 721.174, 721.22, 721.221, 786-0, A-10, A-375, A-431, A-498, A-673, A172, A2.A2, A20, A2058, A2780, A3.01, A549, A7r5, Adipocyte (pre), Adipocyte (pre)-human diabetes Tp.2, Adipose stem cell-human diabetes Tp.1, Adipose stem cell-human diabetes Tp.2, Adipose stem cell, Adrenocortical, AGN2a, AGS, AML, AML-DC, ARH 77, ARPE-19, arteries mesenteric (MA), astrocyte glioblastoma line-mouse, Astrocyte-human (NHA), Astrocyte-mouse, Astrocyte-rat, Astrocyte, ASZ001, AT-1, ATDC5, B cell-human, B-cell-lymphoma cell line, B-cell-mouse-stimulated, B-CLL, b-END, B157, B16-F0, B16-F1, B16-F10, B35, B3Z, B65, BA/F3, Babesia Bovis, Balb/c 3T3, BC-1, BCBL1, BCL1 clone 5B1b, BCL1.3B3, BE2-M17, BEAS-2B, Beta islet cell, BeWo, BHK-21, BHP2-7, BJ, BJ1-hTERT, BJAB, BJMC3879, BL2, BL3, BLCL, BPH1, BRIN-BD11, BT-20, BT549, BV173, BV2, BW5147, BW5147.3, BxPC-3, or other types of cells.

Nonlimiting examples of cells may comprise C10/MJ2, C17.2, C28A2, C2C12, C2F3, C3H10T1/2, C57MG, C6, C8161, CA46, Caco-2, Caco-2/TC7, Cal-1, Cal-85-1, CAL51, Calu-3, Calu-6, CAMA 1, CAP (CEVEC's Amniocyte Production), Capan-1, Capan2, Cardiomyocyte, CCD18Co, CCRF-CEM, CCRF-CEM C7, CD34+ cell, CEM-C7A, CEM.C1, Cervical stroma, CFBE, CH1, CH12, CH12F3, CH27, CHM 2100, CHO (suspension), CHO-DG44, CHO-DG44 (DHFR−), CHO-K1, CHO-S cells sold under the trademark FREESTYLE by Thermo Fisher Scientific (Waltham, Mass.), CHO-S (suspension), Chondrocyte (human (NHAC-kn)), Chondrocytes (mouse), Chromaffin cells (cow), CML, Colo201, Colo205, Colo357, Cor.At Cardiomyocytes (from ESC-mouse), COS-1, COS-7, CRFK, CTLL-2, CV1, Cytokine induced killer, Cytotrophoblast, D1 ORL UVA, D1F4, D283, D425, D54, Dante-BL, Daudi, DCIS, Dendritic cell (human), Dendritic cell (mouse-immat.-BALB/c), Dendritic cell (mouse-immat.-C57BL/6), Dendritic cell (mouse-mature-BALB/c), Dendritic cell (mouse-mature-C57BL/6), Dendritic cell (plasmacytoid-human), Dendritic cell (rhesus macaque), DEV, DHL4, DHL6, DLD-1, DO11.10, DOHH-2, Dorsal root gang (DRG), Dorsal root gang (DRG) (rat), Dorsal root gang (DRG) (chicken), Dorsal root gang (DRG) (mouse), DOV13, DPK, DT40, DU 145, EAhy926, eCAS, ECC-1, EcR293, ECV304, or other types of cells.

Nonlimiting examples of cells may comprise Eimeria Tenella, EJM, EL4, Embryonic fibroblast, Embryonic fibroblast (chicken), Embryonic fibroblast (mouse (MEF) immort), Embryonic fibroblast (mouse (MEF) primary), Embryonic stem (ES) cell (human), Embryonic stem (ES) cell (mouse), EMC, Endothelial, Endothelial-aortic-cow (bAEC), Endothelial-aortic-human (HAEC), Endothelial-aortic-pig, Endothelial-coronary art-human (HCAEC), Endothelial-lung-sheep, Endothelial-Mammary-Human, Endothelial-MV dermal-human adult, Endothelial-MV dermal-human neo, Endothelial-MV lung-human (HMVEC-L), Endothelial-pulmonary artery-human, Endothelial-umbilical vn-human (HUVEC), EpH4, Epithilial, Epithelial model-cornea-human-immort., Epithelial-airway-human, Epithelial-airway-pig, Epithelial-alveolar-rat, Epithelial-bronchial (NHBE)-human, Epithelial-bronchial-monkey, Epithelial-cornea-human, epithelial-ES-derived-human, Epithelial-lung type II-human, Epithelial-mammary-human (HMEC), Epithelial-mammary-mouse, Epithelial-prostate (PrEC)-human, Epithelial-renal human (HRE), Epithelial-retinal pigment-human, Epithelial-Small Airway-human (SAEC), ESS-1, F36P, F9, FaO, FDC-P1, FDCP-Mix, Fibroblast, Fibroblast-aortic adventitial-human, Fibroblast-cardiac-rat, Fibroblast-cow, Fibroblast-dermal (NHDF-Neo)-human neo, Fibroblast-dermal (NHDF-Ad)-human adult, Fibroblast-dermal-human, Fibroblast-dermalmacaque, Fibroblast-ES-derived-human, Fibroblast-foreskin-human, Fibroblast-humanGM06940, Fibroblast-lung-human normal (NHLF), Fibroblast-lung-mouse, Fibroblast-lungrat, Fibroblast-pig, Fibroblast-tunica albuginea-human, or other types of cells.

Nonlimiting examples of cells may comprise FL5.12A, FM3A, FRT, G-361, GaMG, GD25, GH3, GIST882, GM00131, GM05849, GM09582, Granta519, Granule cell, Granule cell (CGC)-mouse, Granule cell (CGC)-rat, GT1-7, H2K mdx, H4, H4IIE, H69, H9, H9c2(2-1), HaCaT, HC11, HCA7, HCC1937, HCC1954, HCT 116, HCT15, HDLM-2, HDQ-P1, HEL 92.1.7, HeLa, HeLa S3, Hep G2, Hep1B, HEPA 1-6, Hepa-1c1c7, Hepatocyte, Hepatocyte immortalized-mouse, Hepatocyte-human, Hepatocyte-mouse, Hepatocyte-rat, HFF-immort., HFF-1, HFFF2, HIB1B, High Five, HK-2, HL-1, HL-60, HMC-1, HMEC-1, HMLE, HMy2.CIR (C1R), HN5, HPB-ALL, Hs 181.Tes, Hs 578T, HT-1080, HT-29, HT22, HT29-D4, HTC, HU609, HuH7, HuT 102, HuT 78, HUV-EC-C, IEC-6, IEC18, IGROV1, IHH, IM9, IMR-32, IMR-90, INS-1, INS-1E, INS1 832/13, IOSE29, IOSE80, PS-human, J-774, J-Lat 6.2, J558L, J774A.1, JB6-1, JB6-2, JeKo-1, or other types of cells.

Nonlimiting examples of cells may comprise Jurkat, Jurkat-modified, JVM, JVM-2, K-562, Karpas 299, KE-37, Kelly, Keratinocyte, Keratinocyte-(NHEK-Ad) human adult, Keratinocyte-(NHEK-neo) human neonatal, KG-1, KG-1a, KHYG1, KIT225, KM-H2, KS, KTA2, Ku812, L-428, L1.2, L1210, L1236, L3.6SL, L5178Y, L540, L6, L87/4, LA-N-2, LA-N-5, LAMA-84, Langerhans cells, Langerhans cells-human, LAZ 221, LbetaT2, LCL, Leishmania tarentolae, LLC-MK2, LLC-PK1, LLC-PK10, LN229, LNC, LNCaP, LoVo, LP1, LS180, LX-2, LY2, M-07e, M28, MA 104, Macrophage, Macrophage-human, Macrophage-mouse, Macrophage-mouse-BALB/c, Macrophage-mouse-C57BL/6, MC-38, MC/9, MC3, MC3T3, MC3T3-E1, MC57G, McA-RH7777, MCF10, MCF10A, MCF7, MCF7 tet, MCT, MDA-MB-231, MDA-MB-361, MDA-MB-415, MDA-MB-453, MDA-MB-468, MDBK, MDCK, MDCK II, MDCK-C7, ME-1, MedB1, MEG-01, MEL, or other types of cells.

Nonlimiting examples of cells may comprise melan-a, Melanocyte, Melanocyte-(NHEM-neo)-human neonatal, Mesangial cells-Human (NHMC), Mesench. stem (MSC)-pig, Mesenchymal stem cells, Mesenchymal stem cell (MSC)-human, Meso17, Met-1fvb2, MEWO, MFM223, MG-63, MGR3, MHP36, MiaPaCa-2, mlMCD3, MIN6, Mino, MKN-1, mlEND, MLO-Y4, MLP29, MM.1S, MN9D, MOLM-14, MOLT-4, Molt16, Monocyte, MonoMac1 (MM1), MonoMac6 (MM6), Mouse L cell, MPC-11, Mpf, mpkCCD(c14), MPRO, MRC-5, MT4, MTC, MTLn3, Mutu1, MUTZ-2, MUTZ3, MV-4-11, Myoblast, Myoblast-(HSMM) human, Myofibroblast, Myofibroblast-human hepatic, Myofibroblast-rat hepatic, MzCHA-1, N11, N114P2, N1E115, N9, NALM-6, Namalwa, Natural killer (NK)-human, NB-4, NBL-6, NCEB-1, NCI-H1299 (H1299), NCI-H1435, NCI-H2170, NCI-H226 (H226), NCI-H292, NCI-H295R (H295R), NCIH358 (H-358; H358), NCI-H460 (H460), NCI-H69 (H69), NCI-H929 (H929), NCM460, NCTC clone 929, Neural precursor-cow, Neural stem cell (NSC), Neural stem cell (NSC)-human, Neural stem cell (NSC)-mouse, Neural stem cell (NSC)-rat, Neuro-2a (N2a), Neuroblastoma, Neuron-cortical-mouse, Neuron-hippo/cortical-rat, Neuron-hippocampal-chicken, Neuronhippocampal-mouse, Neuron-mesencephalic-rat, Neuron-striatal-mouse, Neuron-striatal-rat, or other types of cells.

Nonlimiting examples of cells may comprise NG108-15, NIH/3T3, NK-92, NK3.3, NKL, NKL1, NRK, NRK-49F, NRK52E, NS0, NS1, NSC34, NTERA-2 cl.D1, OCI- AML1a, OCI-AML2, OCI-AML3, OCI-LY-10, OCI-LY-3, Olfactory neuron-rat, Oligodendrocyte-rat, OP-6, OVCAR3, *P. knowlesi*, P19, P3X63Ag8, P815, PAC2, Pam212, PANC-1, Panc89, PBMC-human, PC-12, PC-3, *Perkinsus marinus, Plasmodium berghei, Plasmodium falciparum, Plasmodium yoelii*, PLB-985, PMC42, Podocyte-mouse, PS1, PtK1, R28, R9ab, RAEL, RAG2−/−R2BM3-7, Raji, Ramos, Rat2, RAW 264.7, RBL, RBL-1, RBL-2H3, RCC26, RD, REH, Renal Cell Carcinoma, Renal proximal tubule cells-human, RF/6A, RFL-6, Rh4, Rin 1046, RIN m5f, RKO, RL-952, RMAS, RPM18226, RS4-11, RT4, RWPE-1, S1A.TB.4.8.2, S49, SA1N, SAM-19, Saos-2, SbC12, Schneider's *Drosophila* Line 2, Schwannoma cell line, SCI-ET27, SCID (adhesive), SET-2, Sf9 (ovarian), Sf9 (ovarian), SGHPL-4, SH-SYSY, SIRC, SK-BR-3, SK-MEL 100, SK-MEL 103, SK-MEL 147, SK-MEL 173, SK-MEL 187, SK-MEL 19, SK-MEL 192, SK-MEL 197, SK-MEL 23, SK-MEL 29, SKMEL 31, SK-MEL 85, SK-MEL 94, SK-MEL-28, SK-MEL-5, SK-N-AS, SK-N-DZ, SK-N-FI, SK-N-MC, SK-N-SH, SK-OV-3, Skeletal muscle-(SkMC) human, SKNAS, SKW6.4, SMCairway (HASM)-human, SMC-aortic (AoSMC)-human, SMC-aortic (AoSMC)-mouse, SMCaortic (AoSMC)-pig, SMC-aortic (AoSMC)-rat, SMC-bladder (BdSMC)-human, SMC bronchial-human normal (BSMC), SMC-cervix-human, SMC-coronary artery-human (CASMC), SMC-coronary-rat, SMC-pulmonary artery (PASMC)-human, SMC-rat, SMC-ureterus human, SMC-uterus-human (UtSMC), SMC-vascular-human, SMC-vascular-monkey, SMC vascular-rat, SP2/0, SP53, Stroco5, SUIT-2, SUM52PE, SUP-T1, SVEC 4-10, SW13, SW1353, SW48, SW480, SW620, SW837, SW872, or other types of cells.

Nonlimiting examples of cells may comprise Synoviocyte-human, SZ95, T cell line-chicken, T cell-human peripheral blood unstim., T cell-human stim., T cell-mouse-BALB/c, T cellmouse-C57BL/6, T cell-rabbit-stimulated, T-47D, T/C-28 a2, T/G HA-VSMC, TO, T1165, T2, T24, T84, TA3, TF-1, TG40, TGW, THP-1, TK6, TOM-1, Tot2, Trabecular meshwork-human, Trabecular meshwork-pig, Trophoblast-human, Trophoblast-mouse, *Trypanosoma brucei, Trypanosoma congolense, Trypanosoma cruzi*, TS/A, TT, Turbinate cell-cow, U-2 OS, U-2940, U-87 MG, U-937, U138MG, U251, U251 MG, U266B1, U373, U373MG, U87, UACC903, UMR 106-01, UMSCC-14A, UT7, UT7 GM-CSF dependent, UT7-Epo, UT7-EpoS1, UT7-TPO, V5, V79, VAL, Vero, WEHI-231, WEHI-279, WERI-Rb-1, WI-38, WIL2-S, WM-266-4, WM35, WRO, XG6, XG6, Z-138, Zebrafish cell line, ZF4, or combinations thereof. In some cases, the cells comprise T cells, hematopoietic stem cells (HSCs), induced pluripotent stem cells (iPSCs), Chinese hamster ovary (CHO) cells, nonphagocytic cells, or other types of cells. Examples of cells may comprise any combination of the cells listed anywhere herein.

In some examples, the cells may be peripheral blood mononuclear cells or PBMCs. PBMCs may be isolated from whole blood. In some examples, PBMCs are isolated by taking whole blood, diluting the whole blood with a buffer (e.g., PBS), and layering the diluted whole blood over Ficoll or Ficoll-Paque in a tube that can be centrifuged. Centrifuging the layered tube (e.g., for 30-40 min at 400-500 g) results in four layers in the tube. The top layer is plasma and can be removed by pipetting. The second layer contains PBMCs. The second layer is generally white and cloudy. This layer can be removed with a pipette and added to warm PBS or medium to wash away any remaining platelets. The cells can be gently centrifuged into a pellet and viability of the cells estimated using Trypan blue staining. The cells can be used immediately or frozen for storage (i.e. cryopreserved). Other methods for isolating PBMCs from whole blood are known in the art.

Cryopreservation is a method for long-term storage of cells. Generally, a cryoprotectant is added to cells in a buffer and the cells frozen. Cryoprotectants are substances that protects viability of cells during freezing. Cryoprotectants protect cells from damage caused by formation of ice crystals during freezing. In some examples, cryoprotectants used for long-term storage of cells may vitrify water on the inside and outside of cells. Generally, cryoprotectants may increase the solute concentration in cells. Cryoprotectants referred to herein generally easily penetrate cells. In cases where cells are viable and one desires viability to be maintained, cryoprotectants should not be toxic to cells. Multiple cryoprotectants are known in the art. Some of these include dimethyl sulfoxide (DMSO) and glycerol. Other cryoprotectants are known in the art. Long-term methods for storing cells that do not use cryoprotectants are known and are also encompassed by the methods disclosed here.

In some examples, PBMCs and other cells and/or nuclei may be cryopreserved by adding a cryoprotectant (e.g., DMSO at a final concentration of 10-20%) and fetal bovine serum at a final concentration of 40%, freezing gradually at −80° C., then placing in liquid nitrogen.

In some instances, a sample may comprise a cell. Alternatively, or in addition, a sample may comprise a cell nucleus. For example, a sample may comprise both a cell and a cell nucleus. In some examples, a cell may be processed and treated to extract and/or separate a cell nucleus. A sample may comprise a cell but not a separated cell nucleus (or a cell in the absence of a separated cell nucleus). A sample may comprise a cell nucleus but not a cell (or a cell nucleus in the absence of a cell). A sample comprising a cell and/or a cell nucleus may further comprise extracellular molecules, such as extracellular nucleic acid molecules (e.g., ambient or background nucleic acid molecules).

Extracellular Molecules

In some instances, samples may contain extracellular molecules, such as extracellular biological molecules. In some examples, a sample comprising a cell and/or cell nucleus may contain extracellular molecules (e.g., extracellular biological molecules, such as extracellular nucleic acid molecules). Extracellular molecules may include any type of molecule or biomolecule. Extracellular molecules may include extracellular nucleic acid molecules such as DNA and/or RNA or any other types of nucleic acid molecules and/or any combination thereof that are not inside a cell or cell nucleus.

In some instances, extracellular molecules may further comprise molecules other than nucleic acid molecules, such as proteins, peptides, substrates, chemicals, or other types of molecules. Extracellular molecules (e.g., extracellular nucleic acid molecules) may also be referred to as free-floating molecules (e.g., free-floating nucleic acid molecules), ambient molecules (e.g., ambient nucleic acid molecules), and/or background molecules (e.g., background nucleic acid molecules). Extracellular molecules may comprise molecules in a sample that are not inside a cell or cell nucleus which may act as impurities and may interfere with the quality of data obtained from analyzing the cells or cell nuclei of the sample. In some cases, extracellular molecules may be present without interfering with the quality of data obtained from analyzing the cells or cell nuclei of the sample.

The extracellular molecules may comprise any kind of molecules, such as nucleic acid molecules, peptides, proteins, substrates, a sequence of nucleic acids, a sequence of amino acids, or other kinds of molecules. In some cases, extracellular molecules may be impurities in the sample. Such extracellular molecules may be removed from the sample resulting in a processed sample which may be free of extracellular molecules (e.g., extracellular nucleic acid molecules).

In some instances, the extracellular molecules may comprise or be extracellular nucleic acid molecules. The extracellular nucleic acid molecules may comprise ribonucleic acid (RNA) or deoxyribonucleic acid (DNA). In some examples, extracellular nucleic acid may comprise at least one of messenger RNA (mRNA), chromosome, and genomic DNA (gDNA). In some examples, the extracellular nucleic acid molecules may comprise a size of at least about 5 base pairs (bp) or nucleotides (nt), for example, at least about 5 bp or nt, 10 bp or nt, 15 bp or nt, 20 bp or nt, 25 bp or nt, 30 bp or nt, 35 bp or nt, 40 bp or nt 50 bp or nt, 60 bp or nt, 70 bp or nt, 80 bp or nt, 90 bp or nt, 100 bp or nt, 200 bp or nt, 300 bp or nt, 400 bp or nt, 500 bp or nt, 600 bp or nt, 700 bp or nt, 800 bp or nt, 900 bp or nt, 1 kbp or knt, or larger in size. In some instances, extracellular nucleic acid molecules may be equal to or smaller than about: 500 bp or nt, 400 bp or nt, 300 bp or nt, 200 bp or nt, 100 bp or nt, 50 bp or nt, 40 bp or nt, 30 bp or nt, 20 bp or nt, 10 bp or nt, 5 bp or nt, or smaller, for example smaller than 50 bp or nt.

In some cases, an extracellular nucleic acid molecule (e.g., chromosome) may comprise a size of at least about 0.01 inch, 0.05 inch, 0.1 inch, 0.2 inch, 0.3 inch, 0.4 inch, 0.5 inch, 0.6 inch, 0.7 inch, 0.8 inch, 0.9 inch, 1 inch, 1.1 inch, 1.2 inch, 1.3 inch, 1.4 inch, 1.5 inch, 1.6 inch, 1.7 inch, 1.8 inch, 1.9 inch, 2 inch, 2.1 inch, 2.2 inch, 23 inch, 2.4 inch, 2.5 inch, or more. In some instances, an extracellular nucleic acid molecule (e.g., chromosome) may comprise a size of at least about 1 nanometer(s) nm, 2 nm, 3 nm, 4 nm, 5 nm, 6 nm, 7 nm, 8 nm, 9 nm, 10 nm, 20 nm, 30 nm, 40 nm, 50 nm, 60 nm, 70 nm, 80 nm, 90 nm, 100 nm, 200 nm, 300 nm, 400 nm, 500 nm, 600 nm, 700 nm, 800 nm, 900 nm, 1 micrometer(s) (µm), 2 µm, 3 µm, 4 µm, 5 µm, 6 µm, 7 µm, 8 µm, 9 µm, 10 µm, 20 µm, 30 µm, 40 µm, 50 µm, 60 µm, 70 µm, 80 µm, 90 µm, 100 µm, 200 µm, 300 µm, 400 µm, 500 µm, 600 µm, 700 µm, 800 µm, 900 µm, 1 millimeter(s) mm, 2 mm, 3 mm, 4 mm, 5 mm, 6 mm, 7 mm, 8 mm, 9 mm, 10 mm, 20 mm, 30 mm, 40 mm, 50 mm, 60 mm, 70 mm, 80 mm, 90 mm, 100 mm, 200 mm, 300 mm, 400 mm, 500 mm, 600 mm, 700 mm, 800 mm, 900 mm, 1 centimeter(s) m, 2 cm, 3 cm, 4 cm, 5 cm, 6 cm, 7 cm, 8 cm, 9 cm, 10 cm, or larger.

In some instances, the extracellular molecules may comprise molecules such as extracellular peptides, proteins, substrates, a sequence of amino acids, chemicals, impurities and/or any combination thereof. For example, a sample comprising a cell or cell nucleus may further comprise extracellular molecules such as proteins and/or peptides.

In some instances, extracellular molecules (e.g., extracellular nucleic acid molecules) may have been released in the sample from a cell or cell nucleus, for example, as a result of processing, treating, and/or manipulating a sample comprising a cell and/or a cell nucleus (e.g., during sample preparation). Extracellular molecules, organelles, and the like, may also be released from cells as cell grow and/or propagate. For example, during cell growth, some cells in a population may die and/or lyse to release such molecules and/or organelles.

Such processing and/or cell death may have caused or be associated with cell lysis or a loss of the integrity of the cell membrane and/or the nuclear membrane. This phenomenon may occur in any kind of cell, such as any cell type listed elsewhere herein or other types of cells. In some cases, a cell type that is more fragile may be more prone to getting lysed during sample preparation. Such cell type may be more likely to release extracellular molecules in the sample. Alternatively, the extracellular molecules (e.g., extracellular nucleic acid molecules) may have other origins and/or causes. Recognized is a need to address a contamination (or cross-contamination) of a sample with extracellular molecules (e.g., extracellular nucleic acid molecules) and their interference with data analysis (e.g., single cell analysis such as single cell sequencing or other sample processing and analysis techniques or procedures).

In some examples, the extracellular molecules may function to hold individual biological particles or components of biological particles together in an aggregate or clump.

Clumping and Aggregation of Particles

Particles, including biological particles, and cells and/or nuclei in samples received by and/or used in laboratory settings may exist in various configurations. In some configurations, individual cells are individual units that are not attached or bound to one another. Under the microscope, a diluted preparation of cells in this configuration will contain single cells (schematically illustrated in FIG. 2 as 210).

In some configurations, cells may not appear as unattached or unbound to one another. Under the microscope (and/or using image-analysis systems), diluted preparations of cells in this configuration may appear as aggregates or clumps of cells (schematically illustrated in FIG. 2 as 202 and 205).

Cells may exist in aggregates or clumps for a variety of reasons. In some examples, attached cultured cells that are over-digested with trypsin (i.e., trypsin may be removed to remove attached cells from a surface) may appear as aggregates. Mechanical force or stress may cause cells to clump. Disaggregation of cells from a tissue may be clumped. Cultured cells that have overgrown may appear clumped. Cells may die in a culture or may be lysed during certain types of processing and, as a result, release intracellular molecules that may cause lysed cells, cellular debris, non-lysed cells and/or nuclei to clump. For purposes of illustration, these releases molecules, referred to as extracellular or ambient molecules, may act as a "glue" to hold cells and/or nuclei together in clumps. There may be other reasons that cells aggregate or clump. Generally, aggregated or clumped cells can be used in the methods disclosed here regardless of the reason or mechanism by which the cells aggregate.

In some examples, cryopreserved cells that are revived or thawed may be present in aggregates or clumps (e.g., see Clinical and Experimental Immunology 163:33-49, 2010). Viability of some cryopreserved cells is lost when the cells are revived or thawed. Nonviable cells may release cellular components (e.g., the cellular components are not enclosed by a cell membrane). Cellular debris and/or nucleic acids may be released from the cells. These may be called extracellular debris and extracellular nucleic acids, respectively. While not wishing to be bound by a mechanism, it is believed that some of these extracellular components may act as a sort of "glue" that causes cells to aggregate or clump. One such component is believed to be nucleic acids. One such component is believed to be DNA and/or RNA. In some examples, the methods, compositions and kits disclosed here are designed to de-aggregate or de-clump biological particles of aggregated/clumped cells. In some examples, single cells result. In some examples, viability of the cells is not significantly affected by the methods (e.g., viable cells in an aggregate, which are processed to single cells by the disclosed methods, remain viable). The methods disclosed here are not limited to be used with viable cells. Nonviable (e.g., fixed) cells may be used. Cellular organelles (e.g., nuclei) may be used.

The cell may be subjected to analysis in terms of a phenotype, an intracellular activity, another characteristic or parameter, and/or any combination thereof. In some examples, analytes may be detected and quantified from single cells and/or nuclei. The extracellular molecule may create noise in the data (e.g., single cell data) obtained from the cell and/or cell nuclei in the sample. Eliminating such an extracellular molecule from the sample may enhance the quality of data and a clustering result thereof.

In some instances, the presence of extracellular molecules (e.g., extracellular nucleic acid molecules) in a sample comprising cells and/or cell nuclei may adversely affect and/or at least to some extent compromise the precision or quality of the results of analyses of the cells and/or cell nuclei (e.g., single cell analysis and/or data clustering results). For example, the goal may be to analyze the nucleic acid molecules in the cells and/or cell nuclei (e.g., intracellular nucleic acid molecules) of the sample. The method may further comprise clustering the data generated for the cells and/or the cell nuclei of the sample into more than one subpopulation (e.g., cluster the cell into multiple subpopulations). The method may further comprise identifying combinations of characteristics and/or parameters (e.g., markers) that may provide important information regarding each subpopulation and/or define the subpopulation in terms of a given state or condition of the sample or the subject, for example a disease marker or a diagnosis of the subject. The presence of extracellular molecules such as extracellular nucleic acid molecules may interfere with such clustering and/or identification in one or more ways. This phenomenon may also be referred to as cross-contamination. For example, the presence of extracellular molecules (e.g., ambient or background molecules such as nucleic acid molecules) may cause two or more subpopulations to blend together and the data (e.g., signal or sequencing reads) relating to a cell, cell nucleus, and/or the intracellular nucleic acid molecules thereof to be detected or categorized across two or more subpopulations. Extracellular molecules (e.g., extracellular nucleic acid molecules) may cause artifacts and/or noise in the data, alter the number of subpopulations resulted from the cluster analysis, interfere with the data in other ways, and/or any combinations thereof. This may cause imprecision in data and may adversely affect interpretation of results and/or decision making based on such data and/or data clustering. Therefore, depending on the application, there may be a need to separate extracellular molecules (e.g., extracellular nucleic acid molecules) from the sample (e.g., prior to partitioning).

In some instances, the extracellular molecules (e.g., extracellular nucleic acid molecules), such as nucleic acid molecules inside a sample that are external to a cell or cell nucleus may generate information, such as signals (e.g., sequence reads) during sample processing and/or analysis. For example, a sample comprising a cell or cell nucleus which also comprises extracellular nucleic acid molecules may be subjected to processing and analysis, for example, single cell sequencing (e.g., single cell RNA sequencing). In such case, the signals obtained from the extracellular nucleic acid molecules may be considered noise and may contaminate the data obtained from the intracellular nucleic acid molecules or data obtained from the nucleic acid molecules inside the cell nuclei. In this example, digesting or otherwise decreasing or removing the extracellular nucleic acid molecules from the sample (e.g., prior to sequencing) may enhance the quality of the single cell sequencing data and a clustering thereof.

Methods for Processing Samples and Particles

The methods disclosed here are generally applicable to processing particles with a catalyst on a support and removing the support and attached catalyst to leave processed particles. In some examples, the particles that are processed using the methods are made up of one or more components. In some examples, the processing is designed to break-up the components of the particle into individual components.

In some examples, the methods disclosed here are designed to process biological particles. In some examples, the biological particles may contain multiple components which may be identical, similar or dissimilar. In some examples, the processing is designed to de-aggregate or de-clump the biological particles into their single components.

In some examples, disclosed herein are methods, compositions and kits for processing biological particles that contain multiple cells and/or nuclei configured as aggregates or clumps. The methods may comprise providing a support that may comprise a catalyst. In some examples, the catalyst may be an enzyme. Catalysts and/or enzymes with a variety of functions may be used. In some examples, an enzyme may be configured to degrade or digest an extracellular molecule (e.g., extracellular nucleic acid molecule) in the sample. In some examples, an enzyme may be a nuclease, DNase, and/or RNase. The method may comprise bringing the sample in contact with the support to yield a processed sample or a composition.

In an example of the methods disclosed herein, the sample may be suspected of having an extracellular nucleic acid, and a support comprising a ribonuclease (e.g., attached thereto, such as shown in FIG. 1) may be provided to digest the RNA to smaller pieces, such as to RNA fragments, such that the extracellular nucleic acid molecules (e.g., RNA) be substantially reduced or eliminated in the sample, and thereby providing a more suitable sample (e.g., free of impurities) for performing analyses such as single cell sequencing or other experiments.

Referring to FIG. 1, a catalyst 106 may be a nuclease, such as an exonuclease. A support 108 may be referred to as a bead-bound nuclease, such as a bead-bound exonuclease. Exonucleases may comprise any exonuclease. As an example, an exonuclease may be Exonuclease I (ExoI). ExoI may degrade single-stranded deoxynucleotide DNA in a 3'→5' direction. It may release deoxyribonucleoside 5'-monophosphates (e.g., in a stepwise manner) and leave the 5-terminal dinucleotides intact. Support 108 may digest extracellular (e.g., ambient or background) nucleic acid molecules such as DNA (e.g., genomic DNA (gDNA)). The support 108 may not digest intracellular gDNA and chromatin structure. Therefore, intracellular gDNA and chromatin structure and/or other intracellular nucleic acid molecules may remain intact and/or untouched.

Figure 2:
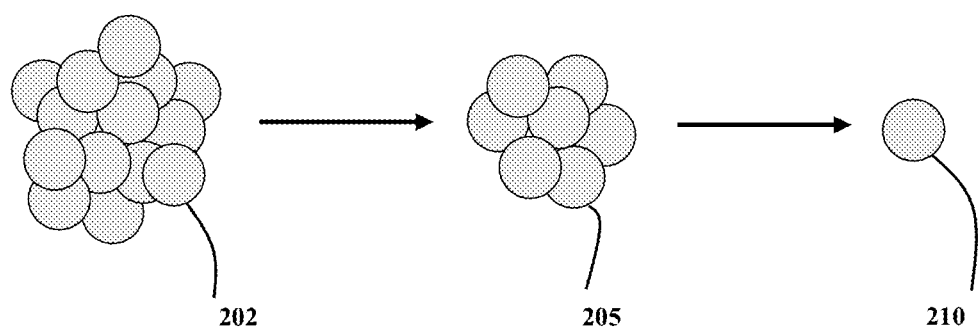
FIG. 2 shows an example of decreasing cell aggregation or clumping.

An example of what some methods disclosed here are designed to accomplish 200 is shown schematically in FIG. 2. In FIG. 2, a progression of a relatively large aggregate of biological particles (e.g., cells) is shown on the left 202. Reduction in size of the aggregate (i.e., de-aggregating or de-clumping) results in a smaller aggregate of biological particles, as shown in the middle 205. Further reduction in size of the aggregate results in single particles, as shown on the right 210.

Figure 3:
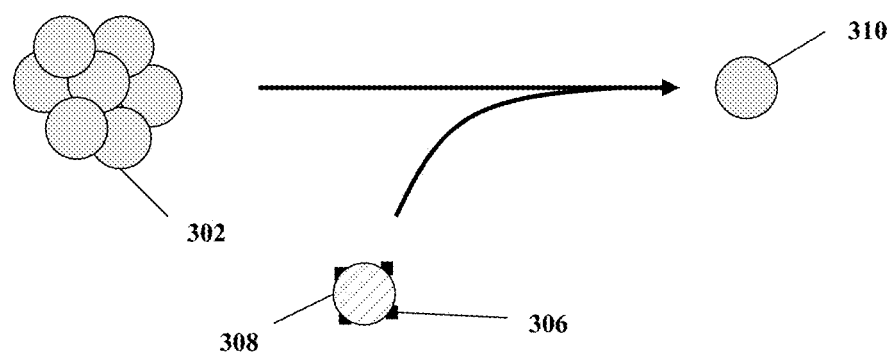
FIG. 3 shows an example method disclosed herein.

In some examples, a method disclosed herein is illustrated in FIG. 3. In the method 300, a biological particle 302 comprised of multiple components, here configured as an aggregate or clump, is contacted with a catalyst 306 attached to a support 308 to yield a processed biological particle 310. The biological particle 302 may include multiple cells and/or nuclei. The processed biological particle 310 may include single components, which may be cells or nuclei.

Figure 4:
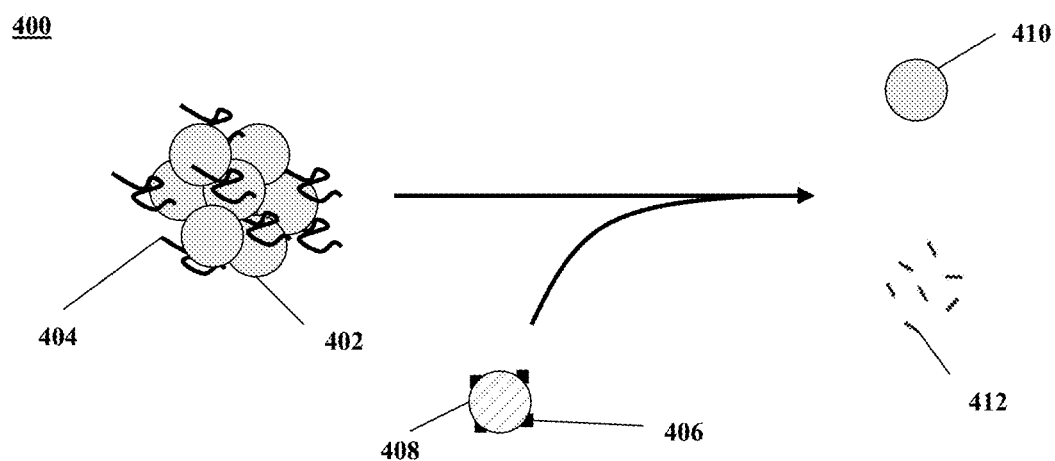
FIG. 4 shows another example method disclosed herein.

In some examples, a method disclosed herein is illustrated in FIG. 4. In the method 400, a biological particle 402 comprised of multiple components, here configured as an aggregate or clump, is contacted with a catalyst 406 attached to a support 408 to yield a processed biological particle 410. The biological particle 402 may include multiple cells and/or nuclei. The processed biological particle 410 may include single components, which may be single cells and/or nuclei. The biological particle 402 may include a substance (e.g., extracellular molecule) 404 that promotes aggregation or clumping of individual components. In some examples, the substance 404 may include nucleic acids, DNA for example. In some 404 may be degraded, inactivated or inhibited by processing with the catalyst 406. In some examples, the substance 404 may be a nucleic acid that is degraded by processing with the catalyst 406. The degraded substance 412 may result from the processing.

In some instances, a method disclosed herein may comprise bringing a support comprising a catalyst, an enzyme for example, in contact with a sample. Bringing the support in contact with the sample may comprise, for example, incubating the support with the sample for a duration of time. In an example, the support may be a bead or a plurality of beads. The beads may be incubated with the sample for a duration of time, for example in a container. The container may be any kind of container such as a tube, microcentrifuge tube, a centrifuge tube, a plate, a multi-well plate, a flask, a dish, a petri-dish, or any other kind of container. For example, the support (e.g., bead) may be incubated with the sample. The support may have any other shape or type. A support may be a surface such as a planar surface (horizontal or vertical) or a non-planar surface (e.g., conical, concave, spherical, etc.). The sample may be disposed on the surface. The sample may pass through the support. For example, the support may be a wall or a column. The support may be a tip or a solid object.

In some instances, the incubation time may depend on a variety of factors such as assay conditions. For example, the sample may be incubated with the support(s) for at least about: 1 second(s), 2 s, 10 s, 20 s, 30 s, 1 minute(s) (min), 2 min, 3 min, 5 min, 10 min, 20 min, 30 min, 45 min, 1 hour(s) (hr), 1.5 hr, 2 hr, 3 hr, 4 hr, or longer. Assay conditions may comprise the composition of the sample and supports and concentrations thereof, the composition of the sample medium such as buffers, temperature, pH, pressure, environmental stimuli, and other factors. In an example, the assay temperature may be about 37° C. In some examples, an assay temperature may be between about 3° C. to about 50° C., for example at a room temperature such as from about 20° C. to about 30° C. In some examples, the temperature of the assay may be at least about: 2° C., 3° C., 4° C., 5° C., 6° C., 7° C., 8° C., 9° C., 10° C., 15° C., 20° C., 25° C., 30° C., 35° C., 40° C., 45° C., 50° C., 60° C., or more. In some cases, the temperature of the assay may be at most about: 60° C., 50° C., 45° C., 40° C., 35° C., 30° C., 25° C., 20° C., 15° C., 10° C., 5° C., 4° C., or less. Alternatively, other temperatures may be used. Assay conditions may be adjusted and/or optimized to enhance a digestion of the extracellular molecules while maintaining cell and/or nucleus integrity and/or viability. Incubation time may vary and may be adjusted accordingly.

The disclosed methods may involve separating the support and the attached catalyst from the processed biological particle. Generally, the concept is that a catalyst may be more easily and efficiently removed from the processed biological particle when attached to a support. Removing the support results in removal of the attached catalyst. Supports may be separated from contact with the biological particle and/or processed biological particle in multiple ways. In some examples, electromagnetic, electromotive, magnetic and/or mechanical forces may be used. In some examples, a centrifugal force may be used. In some examples, filtering and/or affinity separation may be used. In some examples, separation and/or removal may be based on based on differences in physical characteristics of the support as compared to the processed biological particle.

In some instances, a method may comprise processing a sample comprising a cell and/or cell nucleus, thereby providing a composition, such as a processed sample. The sample or composition may be a suspension. The composition (e.g., the processed sample) may comprise a cell and/or cell nucleus. The composition (e.g., processed sample) may further comprise nucleic acid molecule fragments. The nucleic acid molecule fragments may be DNA fragments or RNA fragments, such as the fragments of a DNA or RNA during or after digestion by an enzyme (e.g., an enzyme attached to a support). The nucleic acid molecule fragments may comprise or be a sequence of nucleic acids and/or one or more bases or base pairs. In some cases, a size of a nucleic acid molecule fragment may be at most about 60 bp, 50 bp, 40 bp, 30 bp, 20 bp, 10 bp, 5 bp, or smaller in size. In some cases, the composition (e.g., the processed sample) may be substantially free of extracellular nucleic acid molecules with a size of at least about 60 bp, 70 bp, 80 bp, 100 bp, 200 bp, 300 bp, 400 bp, 500 bp, 600 bp, 700 bp, 800 bp, 900 bp, 1 kbp, or larger. Alternatively, a portion of the extracellular nucleic acid molecules may remain in the processed sample. For example, at most about 99%, 90%, 80%, 70%, 60%, 50%, 40%, 30%, 20%, 10%, 5%, 1%, 0.5%, 0.1% or smaller amounts of the initial extracellular nucleic acid molecules may remain in the processed sample.

In some instances, methods provided herein may yield a processed sample such as a composition and/or a suspension. The processed sample may comprise or be a composition or a suspension. The composition (e.g., a processed sample) may comprise one or more nucleic acid molecule fragments or nucleic acid molecule sequences. The nucleic acid molecule fragments may comprise any size and/or structure. In some cases, the nucleic acid molecule fragments may be linear, cyclic, hairpin, or other structures and/or morphologies. Examples of nucleic acid molecule fragments may comprise elemental nucleotide units. Nucleic acid molecule fragments may comprise a statistical set of oligonucleotides, such as a statistical set of oligonucleotides that may be smaller than an initial extracellular nucleic acid molecule that is degraded or digested by the methods and/or systems provided herein. In an example, a ribonuclease (RNase) may cleave a bond or a plurality of bonds formed by cytidine or uridine nucleotides (e.g., an extracellular nucleic acid molecule) and may form a 3'-phosphorylated product (e.g., a nucleic acid molecule fragment). In another example, an RNase immobilized on a surface of a support may hydrolyze an RNA (e.g., an extracellular nucleic acid molecule) in a sample and may yield nucleic acid molecule fragment such as a 2',3' cyclic nucleotide. Such nucleic acid molecule fragments may remain in the composition (e.g., processed sample). Alternatively, such nucleic acid molecule fragments may be further separated or removed from the processed sample, for example by further processing.

In some instances, the method may further comprise compartmentalizing the sample into a partition or a plurality of partitions. The sample (e.g., a composition such as the processed sample) may be compartmentalized in a plurality of partitions and be subjected to further processing and analysis, such as sequencing (e.g., single cell sequencing in a plurality of droplets or a plurality of wells). Signal reads may be generated for intracellular as well as extracellular nucleic acid molecules that may be present in the sample. Recognized is a need (i) to distinguish the signals generated for the intracellular nucleic acid molecules or nucleic acid molecules inside cell nuclei from the extracellular nucleic acid molecules, or (ii) to partially, substantially, or completely eliminate the signals generated from the extracellular molecules. In some cases, the intracellular vs. extracellular signals may be distinguished using computational methods, systems, and/or tools. Alternatively, the method may comprise reducing the amount of extracellular nucleic acid molecules in a sample comprising a cell and/or cell nucleus that is to be subjected to analysis or removing them. In some cases, the extracellular nucleic acid molecules may be substantially removed or eliminated from a sample comprising cells and/or cell nuclei. The processed sample or composition may be further partitioned in a plurality of partitions after decreasing or substantially removing the extracellular molecules (e.g., extracellular nucleic acid molecules) in the sample.

In some instances, the compartmentalized processed sample or composition may be analyzed, for example by subjecting the processed sample or composition or an emulsion (e.g., plurality of droplets in a continuous phase) thereof to sequencing. Data (e.g., single cell data) may be generated for the cells and/or cell nuclei in the sample. Such data may be analyzed and clustered in a plurality of subpopulations and the characteristics of each subpopulation may be studied and/or defined. In some instances, the reduced amounts of extracellular molecules (e.g., extracellular nucleic acid molecules) or an absence thereof in the composition (e.g., processed sample) may result in more precise and/or more informative data with reduced noise, artifacts, imprecision, and/or error. Such data may comprise higher quality and may result in improved interpretation of results and/or more informed decision making. In some cases, the elimination of extracellular molecules (e.g., extracellular nucleic acid molecules) may reduce the time and expense of data analysis, for example by providing cleaner data comprising reduced noise.

Catalysts and Supports

Generally, the methods disclosed here encompass use of any catalyst. In some examples, the catalyst may be an enzyme. In some instances, the enzyme may be any enzyme configured to digest or degrade an extracellular molecule in the sample (e.g., a sample comprising a cell or cell nucleus). Digestion may comprise hydrolysis. For example, the enzyme may hydrolyze an extracellular molecule. The enzyme may be a hydrolase, a nuclease, a ribonuclease, an exonuclease, a restriction enzyme, a protease, a peptidase, another enzyme, or any combination thereof. The enzyme may be attached to a support, such as a support described elsewhere herein. The support may comprise the enzyme. The enzyme may be attached to the support. The enzyme may be inside the support. The enzyme may degrade an extracellular molecule in the sample while keeping the cell and the intracellular components and/or constituents untouched and/or intact. Likewise, the enzyme and/or support may maintain a cell nucleus in the sample untouched and/or intact.

In some instances, the enzyme may be configured to degrade an extracellular nucleic acid molecule. For example, the extracellular molecule may be DNA, and the enzyme may be deoxyribonuclease configured to digest the DNA. Digestion may comprise hydrolysis or other mechanisms. In some instances, the enzyme may be an exonuclease configured to digest a deoxyribonucleic acid molecule (DNA) in a sample. For example, the sample may be suspected of having an extracellular deoxyribonucleic acid molecule (DNA). A support may be provided to digest the extracellular DNA in the sample, thereby providing a processed sample that may be substantially free of the extracellular DNA molecule. In an example, the enzyme may comprise or be an exonuclease I (ExoI). In some examples, the enzyme may comprise at least one of ribonuclease and exonuclease.

For example, the extracellular molecule may be RNA such as messenger (mRNA), and the enzyme may be ribonuclease configured to digest the RNA. Digestion may comprise hydrolysis or other mechanisms. For example, the sample may be suspected of having an extracellular RNA, and a support comprising a ribonuclease or other enzyme (e.g., attached thereto, such as shown in FIG. 1) may be provided to digest the RNA to smaller pieces, such as to RNA fragments, such that the extracellular nucleic acid molecules (e.g., RNA) be substantially reduced or eliminated in the sample, and thereby providing a more suitable sample (e.g., free of impurities) for performing analyses such as single cell sequencing or other experiments.

In some instances, the enzyme may be permanently or removably attached to the support or a surface thereof, be inside the support, or a combination thereof. For example, the enzyme may be immobilized on a surface of the support. The enzyme may comprise a linker that may be configured to bind a moiety of the surface of the support. For example, the enzyme may be immobilized on a surface of the support by an affinity-tag, entrapment, linkage, cross-linkage, covalent bond, or any combination thereof. In an example, a carbohydrate moiety of the enzyme (e.g., a DNase) may bind the support (e.g., a gel). A gel may comprise any gel listed elsewhere herein. In some examples, gel may comprise agarose, polymer, silica, gel beads, or other kinds of gels. The support may comprise a surface moiety or linker which may be configured to bind the enzyme.

In some instances, attachment of the enzyme to the support may comprise adsorption of the enzyme onto the support (e.g., a matrix). In another example, the enzyme may be included in a gel, such as an inorganic gel by a method such as entrapment. Attachment may comprise chemical attachment (e.g., covalent immobilization). The enzyme may be bound to the surface of the support (e.g., adsorbent surface). For example, an enzyme macromolecule may be attached to a support such as a solid support. In some cases, the bond may remain strong in a wide range of pH, temperature, and/or reaction medium composition. In an example, a reaction (e.g., a direct reaction) may be performed between the amino groups of the enzyme and the support (for example, an epoxy group present in an example support). In another example, a reaction may be performed between an enzyme with an aldehyde-polymer spacer bound to a surface of an example support (e.g., a surface of a monolith support which may be porous).

Generally, enzymes that are associated with a support are enzymes that retain activity when attached to the support. In some instances, an activity of the enzyme, such as, an active conformation geometry of the enzyme may be at least partially maintained upon attachment to the support (e.g., immobilization on the support or a surface thereof). In some cases, the activity of the enzyme may be partially maintained. The activity of the enzyme may be substantially maintained. For example, the activity of the enzyme may be at least about 1%, 5%, 10%, 20%, 30%, 40%, 50%, 60%, 70%, 80%, 90%, 99.99% or more compared to its activity level before being attached or bound to the support.

Various analysis techniques may be used to assess a quality of an attachment or immobilization of the enzyme to the support, such as an immobilization of the enzyme on the surface of the support. For example, chromatography (e.g., high-performance liquid chromatography (HPLC)) may be used to assess an immobilization of an enzyme on the surface of the support.

In some instances, the enzyme may be coupled to the support during or subsequent to the digestion or degradation of the extracellular molecule (e.g., extracellular nucleic acid molecule). For example, the bond between the enzyme and the support may be strong and/or stable under assay conditions for a given duration of time, such as a prolonged duration of time. Alternatively, in some cases, the enzyme may be detached from the support during or after the digestion.

In some instances, the support and/or the enzyme may be configured to be impenetrable to the cell and/or the cell nucleus. The cell nucleus may be internal to or external to a cell in the sample. In some instances, the support and/or the enzymes may not cause physical, chemical, biological, or other kinds of damage to the cell and/or cell nucleus. In some instances, the support and/or the enzymes attached thereto may not trigger apoptosis in the cell, may not alter cellular metabolism, may not interfere with an integrity of the membrane of the cell or cell nucleus, may be inert to the cell and/or cell nucleus, may be safe to the cells, and/or may be compatible for using with a sample comprising a cell and/or cell nucleus.

In some instances, the support (e.g., a bead) may not comprise an enzyme. A support not comprising an enzyme may not degrade an extracellular nucleic acid molecule. In some examples, the method may comprise providing a support configured to bind or attach to an extracellular molecule (e.g., an extracellular nucleic acid molecule). In some examples, the support (e.g., bead) may comprise a coating. The coating may be configured to bind or attach to an extracellular molecule. The coating may be a chemical, a biological, or biochemical coating. In some examples, the coating may comprise a biological particle. Examples of coatings may comprise a molecule or particle such as a nucleic acid molecule, a nucleotide, a sequence of nucleotides, oligonucleotide, a polynucleotide, a double-stranded DNA, RNA, a sequence of amino-acids, a peptide, a virus, a virus DNA, ssDNA, an aptamer, or another molecule. The molecules of the coating may capture extracellular molecules and facilitate their removal from the sample (e.g., by separating the support from the sample). In an example, a support (e.g., a bead) may be a magnetic bead which may be coated with a nucleotide or a chain or sequence of nucleotides (e.g., poly-t). The magnetic bead comprising the coating (e.g., coated by poly-t) may hybridize to a target extracellular nucleic acid molecule (e.g., the poly-A tail of an extracellular mRNA). The magnetic bead may be separated from the sample (e.g., by a magnetic or electromagnetic force), thereby resulting a processed sample. The processed sample may be substantially free of the target extracellular molecule (e.g., mRNA) or comprise low concentrations thereof.

In some instances, the support may be a sphere (e.g., a solid sphere or a gel sphere). The support may be a spherical bead, such as a solid magnetic sphere. The diameter of the sphere may be at least about 0.1 micrometer (μm), 0.2 μm, 0.3 μm 0.4 μm 0.5 μm 0.6 μm 0.7 μm 0.8 μm 0.9 μm, 1 μm, 2 μm, 3 μm, 4 μm, 5 μm, 6 μm, 7 μm, 8 μm, 9 μm, 10 μm, 12 μm, 14 μm, 16 μm, 18 μm, 20 μm, 30 μm, 40 μm, or larger in size. In some examples, the diameter may be between about 1 micrometer (μm) to 20 micrometers (μm). The diameter may be from about 5 micrometers (μm) to 10 micrometers (μm). Alternatively, the diameter may comprise other sizes. Alternatively, the support may comprise a different shape and/or size.

In some instances, the support may be a bead, polymeric matrix, a plane (e.g., a horizontal or vertical planar surface), a tube wall, a pipette tip, a column surface, a micropillar, an array, a well (e.g., one or more surfaces of a well), a particle, a nanoparticle, a molecule, a large molecule, a protein, a peptide, or any combination thereof. The support may be a planar surface. The support may be made of any material. In some examples, the support may be made of a polymeric material. The polymeric material may be any polymeric material provided elsewhere herein. The support or bead may be any support provided elsewhere herein, such as any bead provided elsewhere herein. The support may comprise a polymer, such as a synthetic polymer. As an example, a polymer may comprise or be a monolith. A support may be porous or microporous, such as a microporous monolith.

In some instances, the bead may be a solid bead or a gel bead. The gel bead may be a gel bead provided elsewhere herein. In some examples, the support may be magnetic. For example, the support may be a bead, and the bead may be a magnetic bead. The bead may be a gel bead comprising magnetic particles. The bead may be a solid magnetic microsphere. For example, the support may be a solid microsphere. A magnetic bead may be configured to be separated from the sample using a magnetic or electromagnetic force. Alternatively, the bead may not be magnetic. The bead may be configured to be separated from the sample using techniques other than using a magnetic or electromagnetic force.

In some instances, the support may be a molecule. The molecule may be for example, a peptide, a protein, a sequence, such as a sequence of amino acids, a substrate, or other type of molecule. The support (e.g., molecule) may have an enzyme attached thereto or conjugated thereto. The enzyme may be conjugated to the molecule via a linker, bond, or interaction. The bond may be a chemical bond such as covalent bond or any other kind of bond. The bond or linker may be permanent or removable (e.g., reversible). The molecule may be configured to be impenetrable to the cell. For example, the molecule may comprise a size and/or shape that prevents it from penetrating the cell. For example, a support may be a peptide that is not penetrable to a cell and/or a cell nucleus. Alternatively, the size and/or shape of the molecule alone may not prevent it from penetrating the cell or cell nucleus. The assay conditions may be adjusted or optimized to prevent the penetration of the support into the cell or cell nucleus. For example, a chemical or reagent may be used to prevent the molecule from penetrating the cell or cell nucleus. In an example, a drug, treatment, or inhibitor (e.g., a small molecule inhibitor or other type of inhibitor) may be used to inhibit the penetration of the molecule to the cell or cell nucleus. The molecule (e.g., support) may be degradable upon application of a stimulus. The stimulus may comprise a chemical, light, an energy, heat, PH, force, mechanical force, electrostatic force, an enzyme or any other kind of stimulus. For example, an enzyme may degrade the support. For example, a support may be a peptide molecule, and an enzyme such as a peptidase may be configured to degrade the support, and thereby remove it from the sample.

In some instances, the support (e.g., a bead, a molecule, or other kind of support) may be configured to be impenetrable or substantially impenetrable to the cell and/or the cell nucleus. For example, under the assay conditions, when the support comprising an enzyme is brought into contact with the sample comprising a cell and/or cell nucleus. The support (e.g., bead) and/or the enzymes thereof may not penetrate the cell and/or the cell nucleus. Such assay conditions may comprise temperature, pressure, PH, chemicals, reagents and concentrations thereof, the concentration of the support in the sample, a turbulence in the sample (e.g., due to mixing, vortexing, or other factors), any kind of stimuli that may affect a penetration of the support to the sample. For example, the support may comprise a size and/or shape that may prevent it from penetrating the cell and/or cell nuclei. The size and/or shape of the support may be provided elsewhere herein. Alternatively, the size and/or shape of the support alone may not prevent it from penetrating the cell or cell nucleus, and other assay conditions may be adjusted and/or optimized to prevent the support from penetrating the cell. For example, the temperature of the assay may be adjusted to optimize cell viability and/or to minimize a penetration of the support to the cell or cell nucleus.

In some instances, a support and/or an enzyme thereof may partially penetrate the cells in the sample. For example, a portion of the cell in the sample may be penetrated by the support and/or the enzymes attached thereto, while at least a portion or the cell nucleus remains intact from the supports and/or the enzymes attached thereto. For example, at least about 5%, 10%, 20%, 30%, 40%, 50%, 60%, 70%, 80%, 90%, 99% or more of the cells may be penetrated by the supports and or the enzymes thereof (e.g., the enzymes attached to the supports).

In some instances, the cells penetrated by the support and/or enzyme may remain at least about: 0%, 0.5%, 1%, 2%, 5%, 10%, 15%, 20%, 30%, 40%, 50%, 60%, 70%, 80%, 90%, or a greater portion of the cells may remain viable, intact, or unaffected. In some examples, a portion of the cells penetrated by the supports and/or enzymes thereof may be to some extent affected or compromised (e.g., by the supports and/or enzymes attached thereto). For example, at least about: 0%, 0.5%, 1%, 2%, 5%, 10%, 15%, 20%, 30%, 40%, 50%, 60%, 70%, 80%, 90% of the cells penetrated by the supports and/or enzymes thereof may be affected or compromised. In some examples, at most about 90%, 80%, 70%, 60%, 50%, 40%, 30%, 20%, 10%, 5%, 2%, 1%, or a lower portion of the cells penetrated by the supports and/or enzymes thereof may be affected or compromised.

The cells penetrated by the supports and/or enzymes thereof may remain at least about: 0%, 0.5%, 1%, 2%, 5%, 10%, 15%, 20%, 30%, 40%, 50%, 60%, 70%, 80%, 90%, 99% viable, intact, unaffected, and/or non-compromised. For example, data generated from such cells may be quality data. In some cases, a portion of the cells penetrated by the supports and/or enzymes thereof may be to some extent affected by the supports and/or enzymes attached thereto. For example, at most about: 50%, 40%, 30%, 20%, 10%, 5%, 1%, 0.5%, 0.1%, or less of the cells penetrated by the supports or enzymes thereof may be compromised or affected. In some cases, the cells and/or cell nuclei in the sample may be substantially (e.g., at least 80%, at least 90%, at least 99%, or more) unaffected and/or untouched by the supports and/or enzymes attached thereto. The supports and/or enzymes may degrade the extracellular nucleic acid molecules in the sample without affecting the intracellular nucleic acid molecules or the nucleic acid molecules inside the cell nuclei of the sample.

In some instances, the support and/or the enzymes attached thereto may be compatible to be used with cells and cell nuclei, such that the cell or cell nuclei in the sample would not be compromised and/or affected by the support and/or enzyme attached thereto. For example, the support and or enzymes thereof (e.g., attached thereto) may not alter or affect cellular metabolism, biochemical pathways, intracellular activities, cell organelles, cell viability or functions (e.g., under assay conditions). Quality data may be generated from the cells and cell nuclei in the sample in presence of the supports comprising the enzymes or subsequent to bringing the supports comprising the enzymes in contact with the sample. For example, the intracellular nucleic acid molecules may be analyzed using methods such as single cell sequencing to generate quality data. In some cases, degradation and/or digestion of the extracellular nucleic acid molecules in the sample using the supports and/or enzymes attached thereto may not adversely affect the quality of such data.

In some instances, the support may be configured to be inert or substantially inert to cellular metabolism and intracellular activities. The support and/or enzymes thereof (e.g., attached thereto) may maintain the integrity of the cells or cell nuclei in the sample for at least about 1%, 5%, 10%, 20%, 30%, 40%, 50%, 60%, 70%, 80%, 90%, 99%, or to a greater extent. For example, an integrity of the membrane of the cell and/or nucleus may be substantially maintained. A viability of the cells of the sample may be maintained for at least about 1%, 5%, 10%, 20%, 30%, 40%, 50%, 60%, 70%, 80%, 90%, 99%, or more. The support and or enzymes thereof (e.g., attached thereto) may not trigger apoptosis in the cells.

In some instances, the support may be insoluble in the sample. The sample may comprise a buffer and/or medium. The medium or buffer may be suitable for performing an assay. A buffer may be suitable for providing a condition for the enzyme (e.g., the enzyme attached to the surface of the support) to digest an extracellular molecule in the sample. The buffer may comprise a given composition (e.g., composition of chemical reagents with given concentrations) and given pH. The support may be insoluble in the sample and/or the buffers thereof under the given conditions. Alternatively, in some cases, the support may be at least partially soluble in the sample. In some instances, the solution of the support in the sample may not hinder performing the assay and/or adversely affect the data.

In some instances, the support may be separable from the cell and/or the cell nucleus. The method may further comprise separating the support from the sample. In some examples, the method may comprise separating the support from the sample using a magnetic or electromagnetic force. In other examples, other separation techniques may be used as an alternative or in combination with magnetic separation. Such methods may comprise physical separation, mechanical separation, application of a mechanical force, or other method. A mechanical force may comprise a rotational force, a shear stress, a turbulence, a mechanical force due to fluid flow, pressure, gravity, magnetic enrichment, magnetic force or another force. In some examples, a support may be a magnetic support configured to be separated from the sample via a magnetic or electromagnetic force. For example, a bead may be a solid magnetic sphere or a gel bead comprising magnetic particles. Magnetic beads and magnetic separation may be according to the methods, systems, kits, an/or compositions described in further detail elsewhere herein. Separation techniques may comprise magnetic separation (e.g., separating supports from the sample via a magnetic or electromagnetic force), centrifugation, filtration (e.g., ultrafiltration), using a filter, sorting in a device, using a microfluidic device, a device comprising features configured to trap or otherwise separate the supports, other separation techniques, and/or any combination thereof.

In some instances, a separation technique may comprise using a microfluidic device comprising features such as trappers. A trapper may be a feature that may be configured to separate the support from the sample. A feature may comprise any shape or form. The feature may be two dimensional (2D) or three dimensional (3D). A feature may comprise any geometric shape such as a circle, a cylinder, a rod, a square, a cube, a rectangle, a pyramid, an arc, a semi-arc, a triangle, other shapes, or any combination thereof. In an example, a device comprising features, such as trappers, wells or other features may be configured to separate the supports from the sample. The size of the trappers may be adjusted such that they are configured to trap the supports and thereby separate them from the sample. A processed sample comprising a cell and/or cell nucleus which may be substantially free of extracellular nucleic acid molecules, but which may comprise the supports (e.g., samples 1610 or 1710 shown in FIGS. 16 and 17) may be provided (e.g., inserted or injected) into the device. The supports may be trapped in the features of the device. For example, the features of the device may be cylindrical wells configured to trap a spherical support such as a bead. The size of the well may correspond to the diameter of the support. The diameter of the support may be provided elsewhere herein. In an example, after trapping the supports and separating the sample, the sample (e.g., sample 1620 or 1720 shown in FIGS. 16 and 17). may be provided to a microfluidic device (e.g., a droplet generation junction). The sample may be compartmentalized into partitions such as droplets. The trapping device may be integrated with the droplet generator device. Alternatively, the trapping device may not be integrated with the droplet generator device, and two or separate devices (e.g., microfluidic devices) may be used.

Use in Partition-Based Sample Preparation and Assay Methods

Processed biological particles of this disclosure may be used in partition-based sample preparation and assay methods.

The term "partition," as used herein, generally, refers to a space or volume that may be suitable to contain one or more species or conduct one or more reactions. A partition may be a physical compartment, such as a droplet or well (e.g., a microwell). The partition may isolate space or volume from another space or volume. The droplet may be a first phase (e.g., aqueous phase) in a second phase (e.g., oil) immiscible with the first phase. The droplet may be a first phase in a second phase that does not phase separate from the first phase, such as, for example, a capsule or liposome in an aqueous phase. A partition may comprise one or more other (inner) partitions. In some cases, a partition may be a virtual compartment that can be defined and identified by an index (e.g., indexed libraries) across multiple and/or remote physical compartments. For example, a physical compartment may comprise a plurality of virtual compartments.

A partition may include one or more particles. A partition may include one or more types of particles. For example, a partition of the present disclosure may comprise one or more biological particles and/or macromolecular constituents thereof. A partition may comprise one or more gel beads. A partition may comprise one or more cell beads. A partition may include a single gel bead, a single cell bead, or both a single cell bead and single gel bead. A partition may include one or more reagents. Alternatively, a partition may be unoccupied. For example, a partition may not comprise a bead. A cell bead can be a biological particle and/or one or more of its macromolecular constituents encased inside of a gel or polymer matrix, such as via polymerization of a droplet containing the biological particle and precursors capable of being polymerized or gelled. Unique identifiers, such as barcodes, may be injected into the droplets prior to, subsequent to, or concurrently with droplet generation, such as via a support (e.g., bead), as described elsewhere herein. Microfluidic channel networks (e.g., on a chip) can be utilized to generate partitions as described herein. Alternative mechanisms may also be employed in the partitioning of individual biological particles, including porous membranes through which aqueous mixtures of cells are extruded into non-aqueous fluids.

In an aspect, the systems and methods described herein provide for the compartmentalization, depositing, or partitioning of one or more particles (e.g., biological particles, macromolecular constituents of biological particles, beads, reagents, etc.) into discrete compartments or partitions (referred to interchangeably herein as partitions), where each partition maintains separation of its own contents from the contents of other partitions. The partition can be a droplet in an emulsion. A partition may comprise one or more other partitions.

The partitions can be flowable within fluid streams. The partitions may comprise, for example, micro-vesicles that have an outer barrier surrounding an inner fluid center or core. In some cases, the partitions may comprise a porous matrix that is capable of entraining and/or retaining materials within its matrix. The partitions can be droplets of a first phase within a second phase, wherein the first and second phases are immiscible. For example, the partitions can be droplets of aqueous fluid within a non-aqueous continuous phase (e.g., oil phase). In another example, the partitions can be droplets of a non-aqueous fluid within an aqueous phase. In some examples, the partitions may be provided in a water-in-oil emulsion or oil-in-water emulsion. A variety of different vessels are described in, for example, U.S. Patent Application Publication No. 2014/0155295, which is entirely incorporated herein by reference for all purposes. Emulsion systems for creating stable droplets in non-aqueous or oil continuous phases are described in, for example, U.S. Patent Application Publication No. 2010/0105112, which is entirely incorporated herein by reference for all purposes.

In some instances, a droplet is formed by creating an emulsion by mixing or agitating immiscible phases. Mixing or agitation may comprise various agitation techniques, such as vortexing, pipetting, tube flicking, or other agitation techniques. In some cases, mixing or agitation may be performed without using a microfluidic device. In some examples, a droplet may be formed by exposing a mixture to ultrasound or sonication. For example, to partition contents into droplets, a mixture comprising a first fluid, a second fluid, optionally a surfactant, and the contents can be subject to such agitation techniques to generate a plurality of droplets (first fluid-in-second fluid or second fluid-in-first fluid) comprising the contents, or subsets thereof. In an example, a mixture comprises beads. Upon agitation, the beads in the mixture may limit droplet break-up into droplets smaller than the size of the beads, and a substantially monodisperse population of droplets comprising the beads may result.

In the case of droplets in an emulsion, allocating individual particles to discrete partitions may in one non-limiting example be accomplished by introducing a flowing stream of particles in an aqueous fluid into a flowing stream or reservoir of a non-aqueous fluid, such that droplets are generated (see generally, e.g., FIGS. 5-10, 18A and 18B). Fluid properties (e.g., fluid flow rates, fluid viscosities, etc.), particle properties (e.g., volume fraction, particle size, particle concentration, etc.), microfluidic architectures (e.g., channel geometry, etc.), and other parameters may be adjusted to control the occupancy of the resulting partitions (e.g., number of biological particles per partition, number of beads per partition, etc.). For example, partition occupancy can be controlled by providing the aqueous stream at a certain concentration and/or flow rate of particles. To generate single biological particle partitions, the relative flow rates of the immiscible fluids can be selected such that, on average, the partitions may contain less than one biological particle per partition in order to ensure that those partitions that are occupied are primarily singly occupied. In some cases, partitions among a plurality of partitions may contain at most one biological particle (e.g., bead, DNA, cell or cellular material). In some embodiments, the various parameters (e.g., fluid properties, particle properties, microfluidic architectures, etc.) may be selected or adjusted such that a majority of partitions are occupied, for example, allowing for only a small percentage of unoccupied partitions. The flows and channel architectures can be controlled as to ensure a given number of singly occupied partitions, less than a certain level of unoccupied partitions and/or less than a certain level of multiply occupied partitions.

Preparation of a partition containing a biological sample that is useful in a partition-based assay involves numerous steps (e.g., sample transport, tissue dissociation, liquid phase washing and transfer, library preparation) that typically take from a few hours to days.

One type of partition-based assay is a droplet-based assay. Such assays use a biological sample that is isolated and partitioned in a discrete droplet in an emulsion. The discrete droplet typically includes a unique identifier for the sample in the form of a unique oligonucleotide sequence also contained in the droplet. The discrete droplet can also contain the assay reagents that are used to generate detectable analytes (e.g., 3' cDNA sequences) from the sample and provide useful information about it (e.g., RNA transcript profile).

In at least one embodiment, the method further comprises generating a discrete droplet comprising (e.g., encapsulating) a processed biological sample (e.g., single cell prepared by the methods described herein). In at least one embodiment, the method further comprises generating a discrete droplet comprising the processed biological sample. In at least one embodiment, the method further comprises generating a discrete droplet comprising a processed biological sample, one or more enzymes, one or more primers, templates and, optionally, a bead.

In at least one embodiment wherein the method comprises generating a discrete droplet, the discrete droplet further comprises assay reagents; optionally, wherein the assay reagents are contained in a bead. In at least one embodiment, the discrete droplet further comprises a barcode; optionally, wherein the barcode is contained in a bead.

Methods, techniques, and protocols useful for partitioning biological samples (e.g., individual cells, biomolecular contents of cells, etc.) into discrete droplets are known and well described in the art. The discrete droplets generated may be in a nanoliter-scale container that can maintain separation the droplet contents from the contents of other droplets in the emulsion. Methods and systems for creating stable discrete droplets encapsulating individual particles from biological samples in non-aqueous or oil emulsions are described in, e.g., U.S. Patent Application Publication Nos. 2010/0105112 and 2019/0100632, each of which is entirely incorporated herein by reference for all purposes. Briefly, generation of discrete droplets in an emulsion encapsulating a biological sample is accomplished by introducing a flowing stream of an aqueous fluid containing the biological sample into a flowing stream of a non-aqueous fluid with which it is immiscible, such that droplets are generated at the junction of the two streams (see FIGS. 5, 6 and 7). By providing the aqueous stream at a certain concentration and/or flow rate of the biological sample, the occupancy of the resulting droplets can be controlled. For example, the relative flow rates of the immiscible fluids can be selected such that, on average, the discrete droplet each contains less than one biological particle. Such a flow rate ensures that the droplets that are occupied are primarily occupied by a single sample (e.g., a single cell). Discrete droplets in an emulsion encapsulating a biological sample may also be accomplished using a microfluidic architecture comprising a channel segment having a channel junction with a reservoir (see FIGS. 8, 9 and 10).

In some cases, the droplets among a plurality of discrete droplets formed contain at most one particle (e.g., one bead, one cell). The flows and microfluidic channel architectures also can be controlled to ensure a given number of singly occupied droplets, less than a certain level of unoccupied droplets, and/or less than a certain level of multiply occupied droplets.

In another aspect of the disclosure, processed biological particles may then be partitioned (e.g., in a droplet or well) with other reagents for processing of one or more analytes as described herein. In one embodiment, the processed biological particle may be partitioned with a support (e.g., a bead) comprising nucleic acid molecules suitable for barcoding of the one or more analytes. In another embodiment, the nucleic acid molecules may include nucleic acid sequences that provide identifying information, e.g., barcode sequence(s).

The term "bead," as used herein, generally refers to a particle. The bead may be a solid or semi-solid particle. The bead may be a gel bead. The gel bead may include a polymer matrix (e.g., matrix formed by polymerization or cross-linking). The polymer matrix may include one or more polymers (e.g., polymers having different functional groups or repeat units). Polymers in the polymer matrix may be randomly arranged, such as in random copolymers, and/or have ordered structures, such as in block copolymers. Cross-linking can be via covalent, ionic, or inductive, interactions, or physical entanglement. The bead may be a macromolecule. The bead may be formed of nucleic acid molecules bound together. The bead may be formed via covalent or non-covalent assembly of molecules (e.g., macromolecules), such as monomers or polymers. Such polymers or monomers may be natural or synthetic. Such polymers or monomers may be or include, for example, nucleic acid molecules (e.g., DNA or RNA). The bead may be formed of a polymeric material. The bead may be magnetic or non-magnetic. The bead may be rigid. The bead may be flexible and/or compressible. The bead may be disruptable or dissolvable. The bead may be a solid particle (e.g., a metal-based particle including but not limited to iron oxide, gold or silver) covered with a coating comprising one or more polymers. Such coating may be disruptable or dissolvable.

Figure 5:
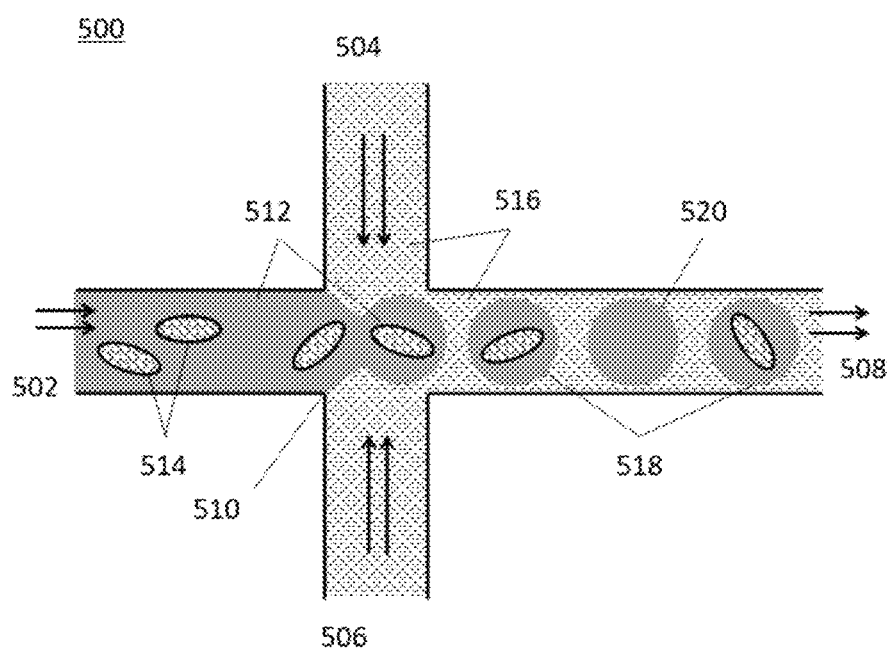
FIG. 5 shows an example of a microfluidic channel structure for partitioning individual biological particles.

FIG. 5 shows an exemplary microfluidic channel structure 500 useful for generating discrete droplets encapsulating a particle from a biological sample, such as a single cell. The channel structure 500 can include channel segments 502, 504, 506 and 508 communicating at a channel junction 510. In operation, a first aqueous fluid 512 that that includes suspended particles (e.g., cells) from a biological sample 514 are transported along channel segment 502 into junction 510, while a second fluid 516 (or "partitioning fluid") that is immiscible with the aqueous fluid 512 is delivered to the junction 510 from each of channel segments 504 and 506 to create discrete droplets 518, 520 of the first aqueous fluid 512 flowing into channel segment 508, and flowing away from junction 510. The channel segment 508 may be fluidically coupled to an outlet reservoir where the discrete droplets can be stored and/or harvested. A discrete droplet generated may include an individual particle from a biological sample 514 (such as droplet 518), or discrete droplet can be generated that includes more than one particle 514 (not shown in FIG. 5). A discrete droplet may contain no biological particle 514 (such as droplet 520). Each discrete droplet is capable of maintaining separation of its own contents (e.g., individual biological sample particle 514) from the contents of other droplets.

Typically, the second fluid 516 comprises an oil, such as a fluorinated oil, that includes a fluoro-surfactant that helps to stabilize the resulting droplets. Examples of useful partitioning fluids and fluoro-surfactants are described in e.g., U.S. Patent Application Publication No. 2010/0105112, which is entirely incorporated herein by reference for all purposes.

The microfluidic channels for generating discrete droplets as exemplified in FIG. 5 may be coupled to any of a variety of different fluid sources or receiving components, including reservoirs, tubing, manifolds, or fluidic components of other systems. Additionally, the microfluidic channel structure 500 may have other geometries, including geometries having more than one channel junction. For example, the microfluidic channel structure can have 2, 3, 4, or 5 channel segments each carrying biological sample particles, assay reagents, and/or beads that meet at a channel junction.

Generally, the fluids used in generating the discrete droplets are directed to flow along one or more channels or reservoirs via one or more fluid flow units. A fluid flow unit can comprise compressors (e.g., providing positive pressure), pumps (e.g., providing negative pressure), actuators, and the like to control flow of the fluid. Fluid may also or otherwise be controlled via applied pressure differentials, centrifugal force, electro-kinetic pumping, vacuum, capillary or gravity flow, or the like.

One of ordinary skill will recognize that numerous different microfluidic channel designs are available that can be used with the methods of the present disclosure to provide discrete droplets containing a biological sample particle, an enzyme composition, and/or a bead with a barcode and/or other assay reagents.

The inclusion of a barcode in a discrete droplet along with the biological sample provides a unique identifier that allows data from the biological sample to be distinguished and individually analyzed. Barcodes can be delivered previous to, subsequent to, or concurrent with the biological sample in discrete droplet. For example, barcodes may be injected into droplets previous to, subsequent to, or concurrently with droplet generation. Barcodes useful in the methods of the present disclosure typically comprise a nucleic acid molecule (e.g., an oligonucleotide). The nucleic acid barcode molecules typically are delivered to a partition via a support, such as bead. In some cases, barcode nucleic acid molecules are initially associated with the bead upon generation of the discrete droplet, and then released from the bead upon application of a stimulus to droplet. Barcode carrying beads useful in the methods of the present disclosure are described in further detail elsewhere herein.

Figure 6:
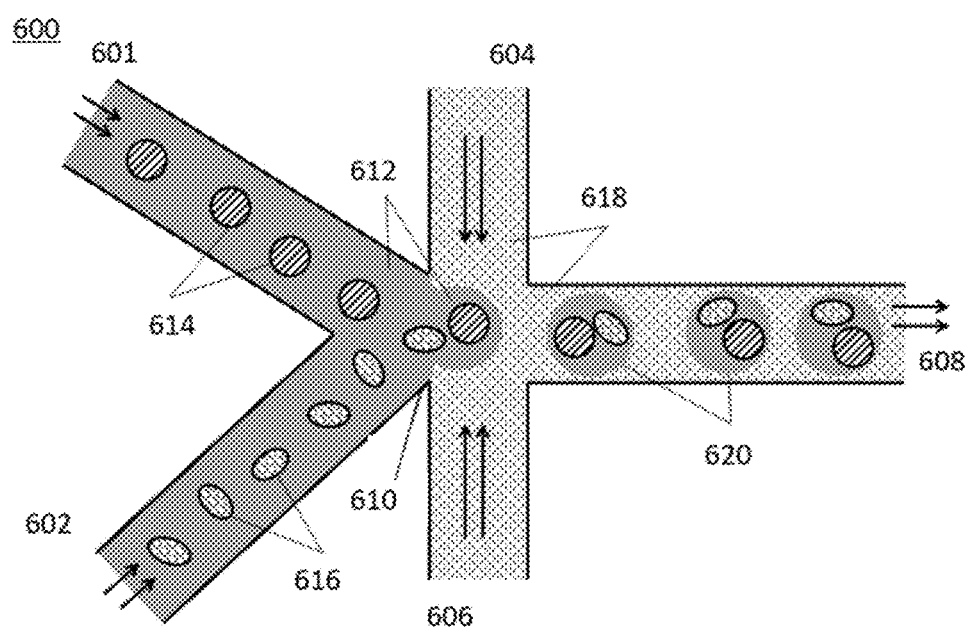
FIG. 6 shows an example of a microfluidic channel structure for delivering barcode carrying beads to droplets.

FIG. 6 shows an exemplary microfluidic channel structure 600 for generating discrete droplets encapsulating a barcode carrying bead 614 along with a biological sample particle 616. The channel structure 600 includes channel segments 601, 602, 604, 606 and 608 in fluid communication at a channel junction 610. In operation, the channel segment 601 transports an aqueous fluid 612 that can include a plurality of beads 614 (e.g., gel beads carrying barcode oligonucleotides) along the channel segment 601 into junction 610. The plurality of beads 614 may be sourced from a suspension of beads. For example, the channel segment 601 can be connected to a reservoir comprising an aqueous suspension of beads 614. The channel segment 602 transports the aqueous fluid 612 that includes a plurality of biological sample particles 616 along the channel segment 602 into junction 610. The plurality of biological sample particles 616 may be sourced from a suspension of biological sample particles. For example, the channel segment 602 may be connected to a reservoir comprising an aqueous suspension of biological sample particles 616. In some instances, the aqueous fluid 612 in either the first channel segment 601 or the second channel segment 602, or in both segments, can include one or more reagents, as further described elsewhere herein. The second fluid 618 that is immiscible with the aqueous fluid 612 is delivered to the junction 610 from each of channel segments 604 and 606. Upon meeting of the aqueous fluid 612 from each of channel segments 601 and 602 and the second fluid 618 (e.g., a fluorinated oil) from each of channel segments 604 and 606 at the channel junction 610, the aqueous fluid 612 is partitioned into discrete droplets 620 in the second fluid 618 and flow away from the junction 610 along channel segment 608. The channel segment 608 can then deliver the discrete droplets encapsulating the biological sample particle and barcode carrying bead to an outlet reservoir fluidly coupled to the channel segment 608, where they can be collected.

As an alternative, the channel segments 601 and 602 may meet at another junction upstream of the junction 610. At such junction, beads and biological particles may form a mixture that is directed along another channel to the junction 610 to yield droplets 620. The mixture may provide the beads and biological particles in an alternating fashion, such that, for example, a droplet comprises a single bead and a single biological particle.

Using such a channel system as exemplified in FIG. 6, discrete droplets 620 can be generated that encapsulate an individual particle of a biological sample, and one bead, wherein the bead can carry a barcode and/or another reagent. It is also contemplated, that in some instances, a discrete droplet may be generated using the channel system of FIG. 6, wherein droplet includes more than one individual biological sample particle or includes no biological sample. Similarly, in some embodiments, the discrete droplet may include more than one bead or no bead. A discrete droplet also may be completely unoccupied (e.g., no bead or biological sample).

In some embodiments, it is desired that the beads, biological sample particles, and generated discrete droplets flow along channels at substantially regular flow rates that generate a discrete droplet containing a single bead and a single biological sample particle. Regular flow rates and devices that may be used to provide such regular flow rates are known in the art, see e.g., U.S. Patent Publication No. 2015/0292988, which is hereby incorporated by reference herein in its entirety. In some embodiments, the flow rates are set to provide discrete droplets containing a single bead and a biological sample particle with a yield rate of greater than 5%, 10%, 20%, 30%, 40%, 50%, 60%, 70%, 80%, 90%, or 95%.

Beads that can carry barcodes and/or other reagents that are useful with the methods of the present disclosure can include beads that are porous, non-porous, solid, semi-solid, semi-fluidic, fluidic, and/or a combination thereof. In some embodiments, the bead can be made of a material that is dissolvable, disruptable, and/or degradable, such as a gel bead comprising a hydrogel. Alternatively, in some embodiments, the bead is not degradable.

In some embodiments of the present disclosure, the bead encapsulated in a discrete droplet with a biological sample is a bead. Typically, the bead useful in the embodiments disclosed herein comprise a hydrogel. Such gel beads can be formed from molecular precursors, such as a polymeric or monomeric species, that undergo a reaction to form cross-linked gel polymer. Another semi-solid bead useful in the present disclosure is a liposomal bead. In some embodiments, beads used can be solid beads that comprise a metal including iron oxide, gold, and silver. In some cases, the bead may be a silica bead. In some cases, the bead can be rigid. In other cases, the bead may be flexible and/or compressible. Generally, the beads can be of any suitable shape. Examples of bead shapes include, but are not limited to, spherical, non-spherical, oval, oblong, amorphous, circular, cylindrical, and variations thereof.

The plurality beads used in the embodiments can be of uniform size or they can comprise a collection of heterogeneous sizes. In some cases, the diameter of a bead is at least about 1 micron (μm), 5 μm, 10 μm, 20 μm, 30 μm, 40 μm, 50 μm, 60 μm, 70 μm, 80 μm, 90 μm, 100 μm, 250 μm, 500 μm, 1000 μm (1 mm), or greater. In some cases, a bead may have a diameter of less than about 1 μm, 5 μm, 10 μm, 20 μm, 30 μm, 40 μm, 50 μm, 60 μm, 70 μm, 80 μm, 90 μm, 100 μm, 250 μm, 500 μm, 1 mm, or less. In some cases, a bead may have a diameter in the range of about 40-75 μm, 30-75 μm, 20-75 μm, 40-85 μm, 40-95 μm, 20-100 μm, 10-100 μm, 1-100 μm, 20-250 μm, or 20-500 μm.

In some embodiments, the beads used are a population or plurality of beads having a relatively monodisperse size distribution. Typically, where it is desirable to provide a consistent amount of a reagent within a discrete droplet, the use of relatively consistent bead characteristics, such as size, provides overall consistency in the content of each droplet. For example, the beads useful in the embodiments of the present disclosure can have size distributions that have a coefficient of variation in their cross-sectional dimensions of less than 50%, less than 40%, less than 30%, less than 20%, and in some cases less than 15%, less than 10%, less than 5%, or less.

The beads useful in the methods of the present disclosure can comprise a range of natural and/or synthetic materials. For example, a bead can comprise a natural polymer, a synthetic polymer or both natural and synthetic polymers. Examples of natural polymers include proteins and sugars such as deoxyribonucleic acid, rubber, cellulose, starch (e.g., amylose, amylopectin), proteins, enzymes, polysaccharides, silks, polyhydroxyalkanoates, chitosan, dextran, collagen, carrageenan, ispaghula, acacia, agar, gelatin, shellac, sterculia gum, xanthan gum, corn sugar gum, guar gum, gum karaya, agarose, alginic acid, alginate, or natural polymers thereof. Examples of synthetic polymers include acrylics, nylons, silicones, spandex, viscose rayon, polycarboxylic acids, polyvinyl acetate, polyacrylamide, polyacrylate, polyethylene glycol, polyurethanes, polylactic acid, silica, polystyrene, polyacrylonitrile, polybutadiene, polycarbonate, polyethylene, polyethylene terephthalate, poly(chlorotrifluoroethylene), poly(ethylene oxide), poly(ethylene terephthalate), polyethylene, polyisobutylene, poly(methyl methacrylate), poly(oxymethylene), polyformaldehyde, polypropylene, polystyrene, poly(tetrafluoroethylene), poly(vinyl acetate), poly(vinyl alcohol), poly(vinyl chloride), poly(vinylidene dichloride), poly(vinylidene difluoride), poly(vinyl fluoride) and/or combinations (e.g., co-polymers) thereof. Beads may also be formed from materials other than polymers, including lipids, micelles, ceramics, glass-ceramics, material composites, metals, other inorganic materials, and others.

Although FIG. 5 and FIG. 6 have been described in terms of providing substantially singly occupied discrete droplets, it is also contemplated in certain embodiments that it is desirable to provide multiply occupied discrete droplets, e.g., a single droplet that contains two, three, four or more cells from a biological sample, and/or multiple different beads, such as a bead carrying a barcode nucleic acid molecule and/or a support (e.g., a bead) carrying a reagent. Accordingly, as noted elsewhere herein, the flow characteristics of the biological particle and/or the supports (e.g., beads) can be controlled to provide for such multiply occupied droplets. In particular, the flow parameters of the liquids used in the channel structures may be controlled to provide a given droplet occupancy rate greater than about 50%, greater than about 75%, and in some cases greater than about 80%, 90%, 95%, or higher.

In some embodiments, the beads useful in the methods of the present disclosure are supports (e.g., beads) capable of delivering reagents into the discrete droplet generated containing the biological sample particle. In some embodiments, the different beads (e.g., containing different reagents) can be introduced from different sources into different inlets leading to a common droplet generation junction (e.g., junction 610). In such cases, the flow and frequency of the different beads into the channel or junction may be controlled to provide for a certain ratio of supports (e.g., beads) from each source, while ensuring a given pairing or combination of such beads into a partition with a given number of biological particles (e.g., one biological particle and one bead per partition).

The discrete droplets described herein generally comprise small volumes, for example, less than about 10 microliters (μL), 5 μL, 1 μL, 900 picoliters (pL), 800 pL, 700 pL, 600 pL, 500 pL, 400 pL, 300 pL, 200 pL, 100 pL, 50 pL, 20 pL, 10 pL, 1 pL, 500 nanoliters (nL), 100 nL, 50 nL, or less. In some embodiments, the discrete droplets generated that encapsulate a biological sample particle have overall volumes that are less than about 1000 pL, 900 pL, 800 pL, 700 pL, 600 pL, 500 pL, 400 pL, 300 pL, 200 pL, 100 pL, 50 pL, 20 pL, 10 pL, 1 pL, or less. It will be appreciated that the sample fluid volume, e.g., including co-partitioned biological particles and/or beads, within the droplets may be less than about 90% of the above described volumes, less than about 80%, less than about 70%, less than about 60%, less than about 50%, less than about 40%, less than about 30%, less than about 20%, or less than about 10% of the above described volumes.

The methods of generating discrete droplets useful with the methods of the present disclosure, result in the generation of a population or plurality of discrete droplets containing a biological sample particle and other reagents. Generally, the methods are easily controlled to provide for any suitable number of droplets. For example, at least about 1,000 discrete droplets, at least about 5,000 discrete droplets, at least about 10,000 discrete droplets, at least about 50,000 discrete droplets, at least about 100,000 discrete droplets, at least about 500,000 discrete droplets, at least about 1,000,000 discrete droplets, at least about 5,000,000 discrete droplets, at least about 10,000,000 discrete droplets, or more discrete droplets can be generated or otherwise provided. Moreover, the plurality of discrete droplets may comprise both unoccupied and occupied droplets.

As described elsewhere herein, in some embodiments of the methods of the present disclosure, the generated discrete droplets encapsulating a biological sample particle, and optionally, one or more different beads, also contain other reagents. In some embodiments, the other reagents encapsulated in the droplet include lysis agents that act to release the biomolecule contents of the biological sample particle within the droplet. In some embodiments, the lysis agents can be contacted with the biological sample suspension concurrently with, or immediately prior to, the introduction of the biological sample particles into the droplet generation junction of the microfluidic system (e.g., junction 210). In some embodiments, the agents are introduced through an additional channel or channels upstream of the channel junction.

Figure 7:
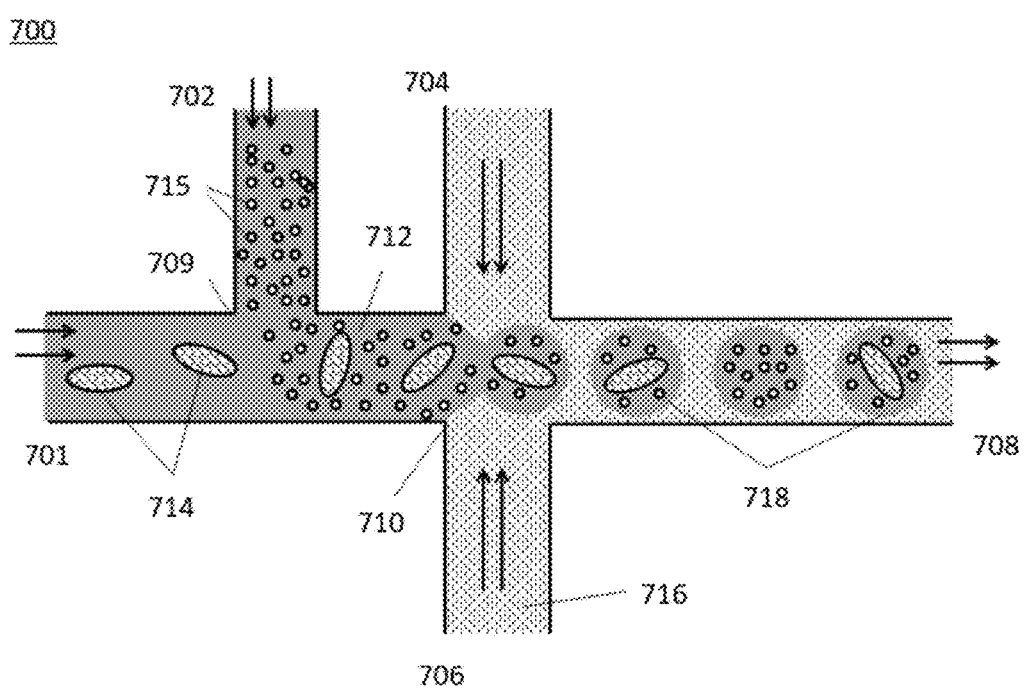
FIG. 7 shows an example of a microfluidic channel structure for co-partitioning biological particles and reagents.

In some embodiments, a biological sample particle can be co-partitioned along with the other reagents. FIG. 7 shows an example of a microfluidic channel structure 700 for co-partitioning biological sample particles and other reagents. The channel structure 700 can include channel segments 701, 702, 704, 706 and 708. Channel segments 701 and 702 communicate at a first channel junction 709. Channel segments 702, 704, 706, and 708 communicate at a second channel junction 710. In exemplary co-partitioning operation, the channel segment 701 may transport an aqueous fluid 712 that includes a plurality of biological sample particles 714 along the channel segment 701 into the second junction 710. As an alternative or in addition to, channel segment 701 may transport beads (e.g., beads that carry barcodes). For example, the channel segment 701 may be connected to a reservoir comprising an aqueous suspension of biological sample particles 714. Upstream of, and immediately prior to reaching, the second junction 710, the channel segment 701 may meet the channel segment 702 at the first junction 709. The channel segment 702 can transport a plurality of reagents 715 in the aqueous fluid 712 along the channel segment 702 into the first junction 709. For example, the channel segment 702 may be connected to a reservoir comprising the reagents 715. After the first junction 709, the aqueous fluid 712 in the channel segment 701 can carry both the biological sample particles 714 and the reagents 715 towards the second junction 710. In some instances, the aqueous fluid 712 in the channel segment 701 can include one or more reagents, which can be the same or different reagents as the reagents 715. A second fluid 716 that is immiscible with the aqueous fluid 712 (e.g., a fluorinated oil) can be delivered to the second junction 710 from each of channel segments 704 and 706. Upon meeting of the aqueous fluid 712 from the channel segment 701 and the second fluid 716 from each of channel segments 704 and 706 at the second channel junction 710, the aqueous fluid 712 is partitioned as discrete droplets 718 in the second fluid 716 and flow away from the second junction 710 along channel segment 708. The channel segment 708 may deliver the discrete droplets 718 to an outlet reservoir fluidly coupled to the channel segment 708, where they may be collected for further analysis.

Discrete droplets generated can include an individual biological sample particle 714 and/or one or more reagents 715, depending on what reagents are included in channel segment 702. In some instances, a discrete droplet generated may also include a barcode carrying bead (not shown), such as can be added via other channel structures described elsewhere herein. In some instances, a discrete droplet may be unoccupied (e.g., no reagents, no biological particles). Generally, the channel segments described herein may be coupled to any of a variety of different fluid sources or receiving components, including reservoirs, tubing, manifolds, or fluidic components of other systems. As will be appreciated, the microfluidic channel structure 700 may have other geometries. For example, a microfluidic channel structure can have more than two channel junctions. For example, a microfluidic channel structure can have 2, 3, 4, 5 channel segments or more each carrying the same or different types of beads, reagents, and/or biological sample particles that meet at a channel junction. Fluid flow in each channel segment may be controlled to control the partitioning of the different elements into droplets. Fluid may be directed flow along one or more channels or reservoirs via one or more fluid flow units. A fluid flow unit can comprise compressors (e.g., providing positive pressure), pumps (e.g., providing negative pressure), actuators, and the like to control flow of the fluid. Fluid may also or otherwise be controlled via applied pressure differentials, centrifugal force, electro-kinetic pumping, vacuum, capillary or gravity flow, or the like.

Figure 8:
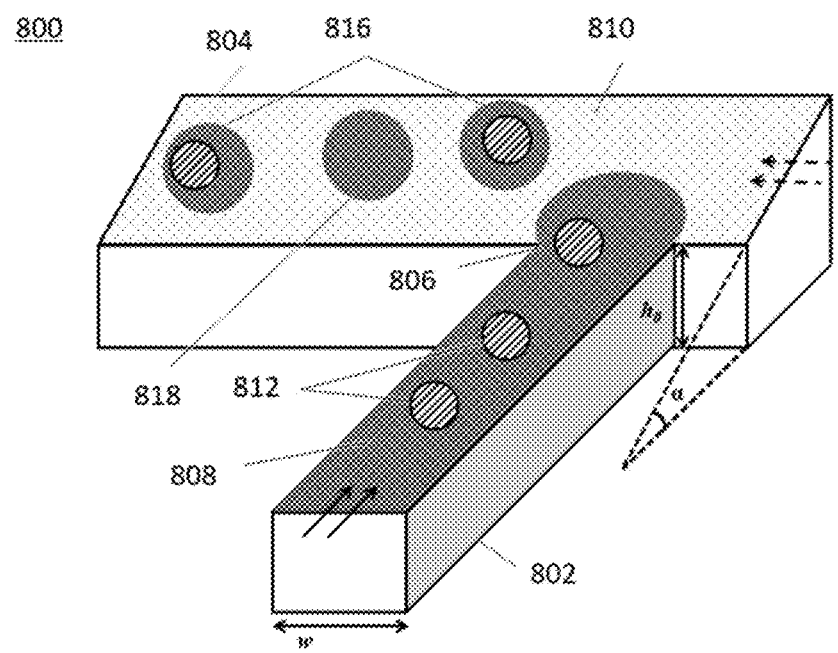
FIG. 8 shows an example of a microfluidic channel structure for the controlled partitioning of beads into discrete droplets.

FIG. 8 shows an example of a microfluidic channel structure for the controlled partitioning of beads into discrete droplets. A channel structure 800 can include a channel segment 802 communicating at a channel junction 806 (or intersection) with a reservoir 804. The reservoir 804 can be a chamber. Any reference to "reservoir," as used herein, can also refer to a "chamber." In operation, an aqueous fluid 808 that includes suspended beads 812 may be transported along the channel segment 802 into the junction 806 to meet a second fluid 810 that is immiscible with the aqueous fluid 808 in the reservoir 804 to create droplets 816, 818 of the aqueous fluid 808 flowing into the reservoir 804. At the junction 806 where the aqueous fluid 808 and the second fluid 810 meet, droplets can form based on factors such as the hydrodynamic forces at the junction 806, flow rates of the two fluids 808, 810, fluid properties, and certain geometric parameters (e.g., w, h0, α, etc.) of the channel structure 800. A plurality of droplets can be collected in the reservoir 804 by continuously injecting the aqueous fluid 808 from the channel segment 802 through the junction 806.

Figure 9:
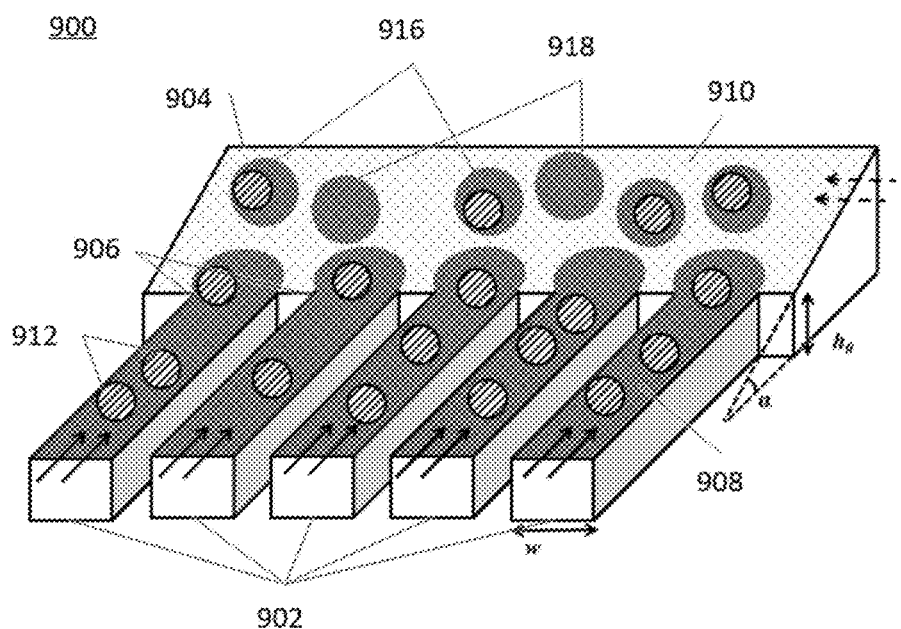
FIG. 9 shows an example of a microfluidic channel structure for increased droplet generation throughput.

FIG. 9 shows an example of a microfluidic channel structure for increased droplet generation throughput. A microfluidic channel structure 900 can comprise a plurality of channel segments 902 and a reservoir 904. Each of the plurality of channel segments 902 may be in fluid communication with the reservoir 904. The channel structure 900 can comprise a plurality of channel junctions 906 between the plurality of channel segments 902 and the reservoir 904.

Each channel junction can be a point of droplet generation. The channel segment 802 from the channel structure 800 in FIG. 8 and any description to the components thereof may correspond to a given channel segment of the plurality of channel segments 902 in channel structure 900 and any description to the corresponding components thereof. The reservoir 804 from the channel structure 800 and any description to the components thereof may correspond to the reservoir 904 from the channel structure 900 and any description to the corresponding components thereof.

Figure 10:
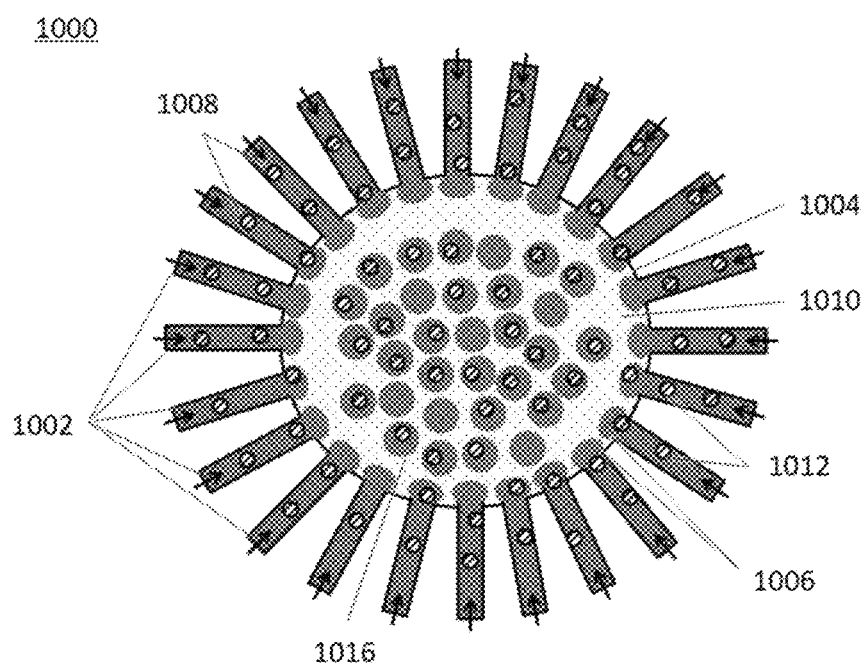
FIG. 10 shows another example of a microfluidic channel structure for increased droplet generation throughput.

FIG. 10 shows another example of a microfluidic channel structure for increased droplet generation throughput. A microfluidic channel structure 1000 can comprise a plurality of channel segments 1002 arranged generally circularly around the perimeter of a reservoir 1004. Each of the plurality of channel segments 1002 may be in fluid communication with the reservoir 1004. The channel structure 1000 can comprise a plurality of channel junctions 1006 between the plurality of channel segments 1002 and the reservoir 1004. Each channel junction can be a point of droplet generation. The channel segment 802 from the channel structure 800 in FIG. 8 and any description to the components thereof may correspond to a given channel segment of the plurality of channel segments 1002 in channel structure 1000 and any description to the corresponding components thereof. The reservoir 804 from the channel structure 800 and any description to the components thereof may correspond to the reservoir 1004 from the channel structure 1000 and any description to the corresponding components thereof. Additional aspects of the microfluidic structures depicted in FIGS. 8, 9 and 10, including systems and methods implementing the same, are provided in US Published Patent Application No 20190323088, which is incorporated herein by reference in its entirety.

Figure 18A:
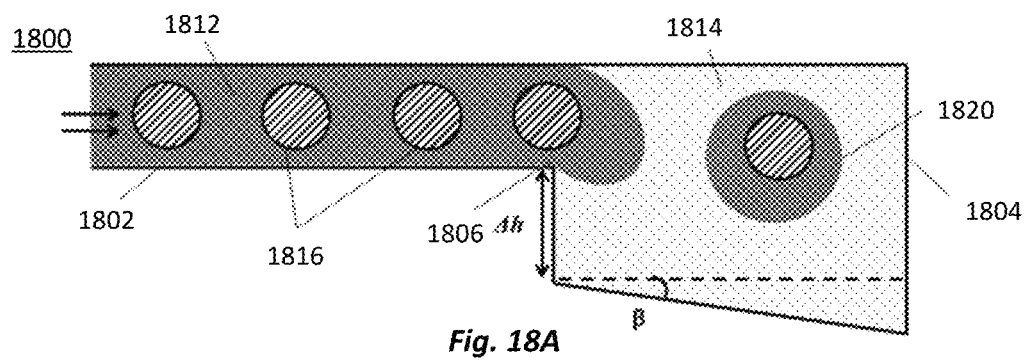
FIG. 18A shows a cross-section view of another example of a microfluidic channel structure with a geometric feature for controlled partitioning.
Figure 18B:
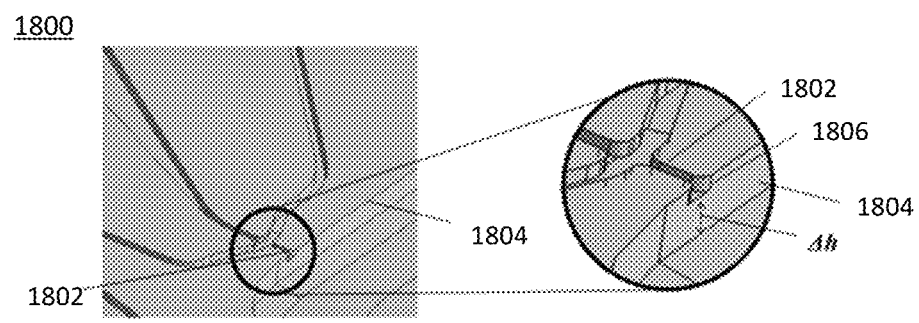
FIG. 18B shows a perspective view of the channel structure of FIG. 18A.

FIG. 18A shows a cross-section view of another example of a microfluidic channel structure with a geometric feature for controlled partitioning. A channel structure 1800 can include a channel segment 1802 communicating at a channel junction 1806 (or intersection) with a reservoir 1804. FIG. 18B shows a perspective view of the channel structure 1800 of FIG. 18A.

An aqueous fluid 1812 comprising a plurality of particles 1816 may be transported along the channel segment 1802 into the junction 1806 to meet a second fluid 1814 (e.g., oil, etc.) that is immiscible with the aqueous fluid 1812 in the reservoir 1804 to create droplets 1820 of the aqueous fluid 1812 flowing into the reservoir 1804. At the junction 1806 where the aqueous fluid 1812 and the second fluid 1814 meet, droplets can form based on factors such as the hydrodynamic forces at the junction 1806, relative flow rates of the two fluids 1812, 1814, fluid properties, and certain geometric parameters (e.g., Δh, etc.) of the channel structure 1800. A plurality of droplets can be collected in the reservoir 1804 by continuously injecting the aqueous fluid 1812 from the channel segment 1802 at the junction 1806.

A discrete droplet generated may comprise one or more particles of the plurality of particles 1816. As described elsewhere herein, a particle may be any particle, such as a bead, cell bead, gel bead, biological particle, macromolecular constituents of biological particle, or other particles. Alternatively, a discrete droplet generated may not include any particles.

In some instances, the aqueous fluid 1812 can have a substantially uniform concentration or frequency of particles 1816. The particles 1816 (e.g., beads) can be introduced into the channel segment 1802 from a separate channel (not shown in FIGS. 18A and 18B). The frequency of particles 1816 in the channel segment 1802 may be controlled by controlling the frequency in which the particles 1816 are introduced into the channel segment 1802 and/or the relative flow rates of the fluids in the channel segment 1802 and the separate channel. In some instances, the particles 1816 can be introduced into the channel segment 1802 from a plurality of different channels, and the frequency controlled accordingly. In some instances, different particles may be introduced via separate channels. For example, a first separate channel can introduce beads and a second separate channel can introduce biological particles into the channel segment 1802. The first separate channel introducing the beads may be upstream or downstream of the second separate channel introducing the biological particles.

In some instances, the second fluid 1814 may not be subjected to and/or directed to any flow in or out of the reservoir 1804. For example, the second fluid 1814 may be substantially stationary in the reservoir 1804. In some instances, the second fluid 1814 may be subjected to flow within the reservoir 1804, but not in or out of the reservoir 1804, such as via application of pressure to the reservoir 1804 and/or as affected by the incoming flow of the aqueous fluid 1812 at the junction 1806. Alternatively, the second fluid 1814 may be subjected and/or directed to flow in or out of the reservoir 1804. For example, the reservoir 1804 can be a channel directing the second fluid 1814 from upstream to downstream, transporting the generated droplets.

The channel structure 1800 at or near the junction 1806 may have certain geometric features that at least partly determine the sizes and/or shapes of the droplets formed by the channel structure 1800. The channel segment 1802 can have a first cross-section height, $h_1$, and the reservoir 1804 can have a second cross-section height, $h_2$. The first cross-section height, $h_1$, and the second cross-section height, $h_2$, may be different, such that at the junction 1806, there is a height difference of Δh. The second cross-section height, $h_2$, may be greater than the first cross-section height, $h_1$. In some instances, the reservoir may thereafter gradually increase in cross-section height, for example, the more distant it is from the junction 1806. In some instances, the cross-section height of the reservoir may increase in accordance with expansion angle, #, at or near the junction 1806. The height difference, Δh, and/or expansion angle, #, can allow the tongue (portion of the aqueous fluid 1812 leaving channel segment 1802 at junction 1806 and entering the reservoir 1804 before droplet formation) to increase in depth and facilitate decrease in curvature of the intermediately formed droplet. For example, droplet size may decrease with increasing height difference and/or increasing expansion angle.

The height difference, Δh, can be at least about 1 μm. Alternatively, the height difference can be at least about 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 200, 300, 400, 500 μm or more. Alternatively, the height difference can be at most about 500, 400, 300, 200, 100, 90, 80, 70, 60, 50, 45, 40, 35, 30, 25, 20, 19, 18, 17, 16, 15, 14, 13, 12, 11, 10, 9, 8, 7, 6, 5, 4, 3, 2, 1 μm or less. In some instances, the expansion angle, #, may be between a range of from about 0.5° to about 4°, from about 0.1° to about 10°, or from about 0° to about 90°. For example, the expansion angle can be at least about 0.01°, 0.1°, 0.2°, 0.3°, 0.4°, 0.5°, 0.6°, 0.7°, 0.8°, 0.9°, 1°, 2°, 3°, 4°, 5°, 6°, 7°, 8°, 9°, 10°, 15°, 20°, 25°, 30°, 35°, 40°, 45°, 50°, 55°, 60°, 65°, 70°, 75°, 80°, 85°, or higher. In some instances, the expansion angle can be at most about 89°, 88°, 87°, 86°, 85°, 84°, 83°, 82°, 81°, 80°, 75°, 70°, 65°, 60°, 55°, 50°, 45°, 40°, 35°, 30°, 25°, 20°, 15°, 10°, 9°, 8°, 7°, 6°, 5°, 4°, 3°, 2°, 1°, 0.1°, 0.01°, or less.

In some instances, the flow rate of the aqueous fluid 1812 entering the junction 1806 can be between about 0.04 microliters (μL)/minute (min) and about 40 μL/min. In some instances, the flow rate of the aqueous fluid 1812 entering the junction 1806 can be between about 0.01 microliters (μL)/minute (min) and about 100 μL/min. Alternatively, the flow rate of the aqueous fluid 1812 entering the junction 1806 can be less than about 0.01 μL/min. Alternatively, the flow rate of the aqueous fluid 1812 entering the junction 1806 can be greater than about 40 μL/min, such as 45 μL/min, 50 μL/min, 55 μL/min, 60 μL/min, 65 μL/min, 70 μL/min, 75 μL/min, 80 μL/min, 85 μL/min, 90 μL/min, 95 μL/min, 100 μL/min, 110 μL/min, 120 μL/min, 130 μL/min, 140 μL/min, 150 μL/min, or greater. At lower flow rates, such as flow rates of about less than or equal to 10 microliters/minute, the droplet radius may not be dependent on the flow rate of the aqueous fluid 1812 entering the junction 1806. The second fluid 1814 may be stationary, or substantially stationary, in the reservoir 1804. Alternatively, the second fluid 1814 may be flowing, such as at the above flow rates described for the aqueous fluid 1812.

In some instances, at least about 50% of the droplets generated can have uniform size. In some instances, at least about 55%, 60%, 65%, 70%, 75%, 80%, 85%, 90%, 95%, 96%, 97%, 98%, 99%, or greater of the droplets generated can have uniform size. Alternatively, less than about 50% of the droplets generated can have uniform size.

While FIGS. 18A and 18B illustrate the height difference, Δh, being abrupt at the junction 1806 (e.g., a step increase), the height difference may increase gradually (e.g., from about 0 μm to a maximum height difference). Alternatively, the height difference may decrease gradually (e.g., taper) from a maximum height difference. A gradual increase or decrease in height difference, as used herein, may refer to a continuous incremental increase or decrease in height difference, wherein an angle between any one differential segment of a height profile and an immediately adjacent differential segment of the height profile is greater than 90°. For example, at the junction 1806, a bottom wall of the channel and a bottom wall of the reservoir can meet at an angle greater than 90°. Alternatively, or in addition, a top wall (e.g., ceiling) of the channel and a top wall (e.g., ceiling) of the reservoir can meet an angle greater than 90°. A gradual increase or decrease may be linear or non-linear (e.g., exponential, sinusoidal, etc.). Alternatively, or in addition, the height difference may variably increase and/or decrease linearly or non-linearly. While FIGS. 18A and 18B illustrate the expanding reservoir cross-section height as linear (e.g., constant expansion angle, β), the cross-section height may expand non-linearly. For example, the reservoir may be defined at least partially by a dome-like (e.g., hemispherical) shape having variable expansion angles. The cross-section height may expand in any shape. Once the lysis agents are co-partitioned in a droplet with a biological sample particle, these reagents can facilitate the release of the biomolecular contents of the biological sample particle within the droplet. As described elsewhere herein, the biomolecular contents released in a droplet remain discrete from the contents of other droplets, thereby allowing for detection and quantitation of the biomolecular analytes of interest present in that distinct biological sample.

Examples of lysis agents useful in the methods of the present disclosure are described elsewhere in this application.

In addition to the lysis agents co-partitioned into discrete droplets with the biological sample particles, it is further contemplated that other assay reagents can also be co-partitioned in the droplet, as described elsewhere in this application.

In some embodiments, the biological sample particles encapsulated in discrete droplets with other reagents are exposed to an appropriate stimulus to release the biomolecular contents of the sample particles and/or the contents of a co-partitioned support (e.g., bead). For example, in some embodiments, a chemical stimulus may be co-partitioned in the droplet along with a biological sample particle and a support (e.g., a bead such as a gel bead) to allow for the degradation of the support and release of the its contents into the droplet.

Additional assay reagents may also be co-partitioned into discrete droplets with the biological samples, as described elsewhere in this application.

In some embodiments, template switching can be used to increase the length of cDNA generated in an assay. In some embodiments, template switching can be used to append a predefined nucleic acid sequence to the cDNA. In an example of template switching, cDNA can be generated from reverse transcription of a template, e.g., cellular mRNA, where a reverse transcriptase with terminal transferase activity can add additional nucleotides, e.g., polyC, to the cDNA in a template independent manner.

Once the contents of a biological sample cell are released into a discrete droplet, the biomolecular components (e.g., macromolecular constituents of biological samples, such as RNA, DNA, or proteins) contained therein may be further processed within the droplet. In accordance with the methods and systems described herein, the biomolecular contents of individual biological samples can be provided with unique barcode identifiers, and upon characterization of the biomolecular components (e.g., in a sequencing assay) they may be attributed as having been derived from the same biological sample. The ability to attribute characteristics to individual biological samples or groups of biological samples is provided by the assignment of a nucleic acid barcode sequence specifically to an individual biological sample or groups of biological samples.

In some aspects, the unique identifier barcodes are provided in the form of nucleic acid molecules (e.g., oligonucleotides) that comprise sequences that may be attached to or otherwise associated with the nucleic acid contents of individual biological sample, or to other components of the biological sample, and particularly to fragments of those nucleic acids. In some embodiments, only one nucleic acid barcode sequence is associated with a given discrete droplet, although in some cases, two or more different barcode sequences may be present. The nucleic acid barcode sequences can include from about 6 to about 20 or more nucleotides within the sequence of the nucleic acid molecules (e.g., oligonucleotides). In some cases, the length of a barcode sequence may be about 6, 7, 8, 9, 10, 11, 12, 13, 14, 15, 16, 17, 18, 19, 20 nucleotides or longer. In some cases, the length of a barcode sequence may be at least about 6, 7, 8, 9, 10, 11, 12, 13, 14, 15, 16, 17, 18, 19, 20 nucleotides or longer. In some cases, the length of a barcode sequence may be at most about 6, 7, 8, 9, 10, 11, 12, 13, 14, 15, 16, 17, 18, 19, 20 nucleotides or shorter. These nucleotides may be completely contiguous, i.e., in a single stretch of adjacent nucleotides, or they may be separated into two or more separate subsequences that are separated by 1 or more nucleotides. In some cases, separated barcode subsequences can be from about 4 to about 16 nucleotides in length. In some cases, the barcode subsequence may be about 4, 5, 6, 7, 8, 9, 10, 11, 12, 13, 14, 15, 16 nucleotides or longer. In some cases, the barcode subsequence may be at least about 4, 5, 6, 7, 8, 9, 10, 11, 12, 13, 14, 15, 16 nucleotides or longer. In some cases, the barcode subsequence may be at most about 4, 5, 6, 7, 8, 9, 10, 11, 12, 13, 14, 15, 16 nucleotides or shorter.

In some embodiments, the nucleic acid barcode molecules can also comprise other functional sequences useful in the processing of the nucleic acids from the biological sample in the droplet. These functional sequences can include, e.g., targeted or random/universal amplification primer sequences for amplifying the nucleic acid molecules from the individual biological samples within the partitions while attaching the associated barcode sequences, sequencing primers or primer recognition sites, hybridization or probing sequences, e.g., for identification of presence of the sequences or for pulling down barcoded nucleic acid molecules, or any of a number of other potential functional sequences.

Beads and Barcode Molecules

Nucleic acid barcode molecules may be delivered to a partition (e.g., a droplet or well) via a support (e.g., a solid support) or carrier (e.g., a bead). In some cases, nucleic acid barcode molecules are initially associated with the support and then released from the support upon application of a stimulus, which allows the nucleic acid barcode molecules to dissociate or to be released from the support. In specific examples, nucleic acid barcode molecules are initially associated with the support (e.g., bead) and then released from the support upon application of a biological stimulus, a chemical stimulus, a thermal stimulus, an electrical stimulus, a magnetic stimulus, and/or a photo stimulus.

A nucleic acid barcode molecule may contain a barcode sequence and a functional sequence, such as a nucleic acid primer sequence or a template switch oligonucleotide (TSO) sequence.

The support may be a bead. A support such as a solid support, e.g., a bead, may be porous, non-porous, hollow, solid, semi-solid, and/or a combination thereof. Beads may be solid, semi-solid, semi-fluidic, fluidic, and/or a combination thereof. In some instances, a support, e.g., a bead, may be dissolvable, disruptable, and/or degradable. In some cases, a support, e.g., a bead, may not be degradable. In some cases, the support, e.g., a bead, may be a gel bead. A gel bead may be a hydrogel bead. A gel bead may be formed from molecular precursors, such as a polymeric or monomeric species. A semi-solid support, e.g., a bead, may be a liposomal bead. Supports, e.g., beads, may comprise metals including iron oxide, gold, and silver. In some cases, the solid support, e.g., the bead, may be a silica bead. In some cases, the support, e.g., a bead, can be rigid. In other cases, the support, e.g., a bead, may be flexible and/or compressible.

A partition may comprise one or more unique identifiers, such as barcodes. Barcodes may be previously, subsequently or concurrently delivered to the partitions that hold the compartmentalized or partitioned biological particle. For example, barcodes may be injected into droplets before, after, or concurrently with droplet generation. The delivery of the barcodes to a particular partition allows for the later attribution of the characteristics of the individual biological particle to the partition. Barcodes may be delivered, for example on a nucleic acid molecule (e.g., an oligonucleotide), to a partition via any suitable mechanism. Beads are described in further detail herein.

In some cases, barcoded nucleic acid molecules can be initially associated with the bead and then released from the bead. Release of the barcoded nucleic acid molecules can be passive (e.g., by diffusion out of the bead). In addition, or alternatively, release from the bead can be upon application of a stimulus which allows the barcoded nucleic acid nucleic acid molecules to dissociate or to be released from the bead. Such stimulus may disrupt the bead, an interaction that couples the barcoded nucleic acid molecules to or within the bead, or both. Such stimulus can include, for example, a thermal stimulus, photo-stimulus, chemical stimulus (e.g., change in pH or use of a reducing agent(s)), a mechanical stimulus, a radiation stimulus; a biological stimulus (e.g., enzyme), or any combination thereof.

In some examples, beads, biological particles (or membrane bound particles) and droplets may flow along channels at substantially regular flow profiles (e.g., at regular flow rates). Such regular flow profiles may permit a droplet to include a single bead and a single biological particle. Such regular flow profiles may permit the droplets to have an occupancy (e.g., droplets having beads and biological particles) greater than 5%, 10%, 20%, 30%, 40%, 50%, 60%, 70%, 80%, 90%, or 95%. Such regular flow profiles and devices that may be used to provide such regular flow profiles are provided in, for example, U.S. Patent Publication No. 2015/0292988, which is entirely incorporated herein by reference.

Beneficially, a discrete droplet partitioning a biological particle and a barcode carrying bead may effectively allow the attribution of the barcode to macromolecular constituents of the biological particle within the partition. The contents of a partition may remain discrete from the contents of other partitions.

A bead may be porous, non-porous, solid, semi-solid, semi-fluidic, fluidic, and/or a combination thereof. In some instances, a bead may be dissolvable, disruptable, and/or degradable. In some cases, a bead may not be degradable. In some cases, the bead may be a gel bead. A gel bead may be a hydrogel bead. A gel bead may be formed from molecular precursors, such as a polymeric or monomeric species. A semi-solid bead may be a liposomal bead. Solid beads may comprise metals including iron oxide, gold, and silver. In some cases, the bead may be a silica bead. In some cases, the bead can be rigid. In other cases, the bead may be flexible and/or compressible.

A bead may be of any suitable shape. Examples of bead shapes include, but are not limited to, spherical, non-spherical, oval, oblong, amorphous, circular, cylindrical, and variations thereof.

Beads may be of uniform size or heterogeneous size. In some cases, the diameter of a bead may be at least about 10 nanometers (nm), 100 nm, 500 nm, 1 micrometer (μm), 5 μm, 10 μm, 20 μm, 30 μm, 40 μm, 50 μm, 60 μm, 70 μm, 80 μm, 90 μm, 100 μm, 250 μm, 500 μm, 1 mm, or greater. In some cases, a bead may have a diameter of less than about 10 nm, 100 nm, 500 nm, 1 μm, 5 μm, 10 μm, 20 μm, 30 μm, 40 μm, 50 μm, 60 μm, 70 μm, 80 μm, 90 μm, 100 μm, 250 μm, 500 μm, 1 mm, or less. In some cases, a bead may have a diameter in the range of about 40-75 μm, 30-75 μm, 20-75 μm, 40-85 μm, 40-95 μm, 20-100 μm, 10-100 μm, 1-100 μm, 20-250 μm, or 20-500 μm.

In certain aspects, beads can be provided as a population or plurality of beads having a relatively monodisperse size distribution. Where it may be desirable to provide relatively consistent amounts of reagents within partitions, maintaining relatively consistent bead characteristics, such as size, can contribute to the overall consistency. In particular, the beads described herein may have size distributions that have a coefficient of variation in their cross-sectional dimensions of less than 50%, less than 40%, less than 30%, less than 20%, and in some cases less than 15%, less than 10%, less than 5%, or less.

A bead may comprise natural and/or synthetic materials. For example, a bead can comprise a natural polymer, a synthetic polymer or both natural and synthetic polymers. Examples of natural polymers include proteins and sugars such as deoxyribonucleic acid, rubber, cellulose, starch (e.g., amylose, amylopectin), proteins, enzymes, polysaccharides, silks, polyhydroxyalkanoates, chitosan, dextran, collagen, carrageenan, ispaghula, acacia, agar, gelatin, shellac, sterculia gum, xanthan gum, Corn sugar gum, guar gum, gum karaya, agarose, alginic acid, alginate, or natural polymers thereof. Examples of synthetic polymers include acrylics, nylons, silicones, spandex, viscose rayon, polycarboxylic acids, polyvinyl acetate, polyacrylamide, polyacrylate, polyethylene glycol, polyurethanes, polylactic acid, silica, polystyrene, polyacrylonitrile, polybutadiene, polycarbonate, polyethylene, polyethylene terephthalate, poly(chlorotrifluoroethylene), poly(ethylene oxide), poly(ethylene terephthalate), polyethylene, polyisobutylene, poly(methyl methacrylate), poly(oxymethylene), polyformaldehyde, polypropylene, polystyrene, poly(tetrafluoroethylene), poly (vinyl acetate), poly(vinyl alcohol), poly(vinyl chloride), poly(vinylidene dichloride), poly(vinylidene difluoride), poly(vinyl fluoride) and/or combinations (e.g., co-polymers) thereof. Beads may also be formed from materials other than polymers, including lipids, micelles, ceramics, glass-ceramics, material composites, metals, other inorganic materials, and others.

In some instances, the bead may contain molecular precursors (e.g., monomers or polymers), which may form a polymer network via polymerization of the molecular precursors. In some cases, a precursor may be an already polymerized species capable of undergoing further polymerization via, for example, a chemical cross-linkage. In some cases, a precursor can comprise one or more of an acrylamide or a methacrylamide monomer, oligomer, or polymer. In some cases, the bead may comprise prepolymers, which are oligomers capable of further polymerization. For example, polyurethane beads may be prepared using prepolymers. In some cases, the bead may contain individual polymers that may be further polymerized together. In some cases, beads may be generated via polymerization of different precursors, such that they comprise mixed polymers, co-polymers, and/or block co-polymers. In some cases, the bead may comprise covalent or ionic bonds between polymeric precursors (e.g., monomers, oligomers, linear polymers), nucleic acid molecules (e.g., oligonucleotides), primers, and other entities. In some cases, the covalent bonds can be carbon-carbon bonds, thioether bonds, or carbon-heteroatom bonds.

Cross-linking may be permanent or reversible, depending upon the particular cross-linker used. Reversible cross-linking may allow for the polymer to linearize or dissociate under appropriate conditions. In some cases, reversible cross-linking may also allow for reversible attachment of a material bound to the surface of a bead. In some cases, a cross-linker may form disulfide linkages. In some cases, the chemical cross-linker forming disulfide linkages may be cystamine or a modified cystamine.

In some cases, disulfide linkages can be formed between molecular precursor units (e.g., monomers, oligomers, or linear polymers) or precursors incorporated into a bead and nucleic acid molecules (e.g., oligonucleotides). Cystamine (including modified cystamines), for example, is an organic agent comprising a disulfide bond that may be used as a crosslinker agent between individual monomeric or polymeric precursors of a bead. Polyacrylamide may be polymerized in the presence of cystamine or a species comprising cystamine (e.g., a modified cystamine) to generate polyacrylamide gel beads comprising disulfide linkages (e.g., chemically degradable beads comprising chemically-reducible cross-linkers). The disulfide linkages may permit the bead to be degraded (or dissolved) upon exposure of the bead to a reducing agent.

In some cases, chitosan, a linear polysaccharide polymer, may be crosslinked with glutaraldehyde via hydrophilic chains to form a bead. Crosslinking of chitosan polymers may be achieved by chemical reactions that are initiated by heat, pressure, change in pH, and/or radiation.

In some cases, a bead may comprise an acrydite moiety, which in certain aspects may be used to attach one or more nucleic acid molecules (e.g., barcode sequence, barcoded nucleic acid molecule, barcoded oligonucleotide, primer, or other oligonucleotide) to the bead. In some cases, an acrydite moiety can refer to an acrydite analogue generated from the reaction of acrydite with one or more species, such as, the reaction of acrydite with other monomers and cross-linkers during a polymerization reaction. Acrydite moieties may be modified to form chemical bonds with a species to be attached, such as a nucleic acid molecule (e.g., barcode sequence, barcoded nucleic acid molecule, barcoded oligonucleotide, primer, or other oligonucleotides). Acrydite moieties may be modified with thiol groups capable of forming a disulfide bond or may be modified with groups already comprising a disulfide bond. The thiol or disulfide (via disulfide exchange) may be used as an anchor point for a species to be attached or another part of the acrydite moiety may be used for attachment. In some cases, attachment can be reversible, such that when the disulfide bond is broken (e.g., in the presence of a reducing agent), the attached species is released from the bead. In other cases, an acrydite moiety can comprise a reactive hydroxyl group that may be used for attachment.

Functionalization of beads for attachment of nucleic acid molecules (e.g., oligonucleotides) may be achieved through a wide range of different approaches, including activation of chemical groups within a polymer, incorporation of active or activatable functional groups in the polymer structure, or attachment at the pre-polymer or monomer stage in bead production.

For example, precursors (e.g., monomers, cross-linkers) that are polymerized to form a bead may comprise acrydite moieties, such that when a bead is generated, the bead also comprises acrydite moieties. The acrydite moieties can be attached to a nucleic acid molecule (e.g., oligonucleotide) that comprises one or more functional sequences, such as a TSO sequence or a primer sequence (e.g., a poly T sequence, or a nucleic acid primer sequence complementary to a target nucleic acid sequence and/or for amplifying a target nucleic acid sequence, a random primer, or a primer sequence for messenger RNA) that is useful for incorporation into the bead, etc.) and/or one or more barcode sequences. The one or more barcode sequences may include sequences that are the same for all nucleic acid molecules coupled to a given bead and/or sequences that are different across all nucleic acid molecules coupled to the given bead. The nucleic acid molecule may be incorporated into the bead.

In some cases, the nucleic acid molecule can comprise one or more functional sequences. For example, a functional sequence can comprise a sequence for attachment to a sequencing flow cell, such as, for example, a P5 sequence for Illumina® sequencing. In some cases, the nucleic acid molecule or derivative thereof (e.g., oligonucleotide or polynucleotide generated from the nucleic acid molecule) can comprise another functional sequence, such as, for example, a P7 sequence for attachment to a sequencing flow cell for Illumina sequencing. In some cases, the functional sequence can comprise a barcode sequence or multiple barcode sequences. In some cases, the functional sequence can comprise a unique molecular identifier (UMI). In some cases, the functional sequence can comprise a primer sequence (e.g., an R1 primer sequence for Illumina sequencing, an R2 primer sequence for Illumina sequencing, etc.). In some cases, a functional sequence can comprise a partial sequence, such as a partial barcode sequence, partial anchoring sequence, partial sequencing primer sequence (e.g., partial R1 sequence, partial R2 sequence, etc.), a partial sequence configured to attach to the flow cell of a sequencer (e.g., partial P5 sequence, partial P7 sequence, etc.), or a partial sequence of any other type of sequence described elsewhere herein. A partial sequence may contain a contiguous or continuous portion or segment, but not all, of a full sequence, for example. In some cases, a downstream procedure may extend the partial sequence, or derivative thereof, to achieve a full sequence of the partial sequence, or derivative thereof. Examples of such nucleic acid molecules (e.g., oligonucleotides, polynucleotides, etc.) and uses thereof, as may be used with compositions, devices, methods and systems of the present disclosure, are provided in U.S. Patent Pub. Nos. 2014/0378345 and 2015/0376609, each of which is entirely incorporated herein by reference.

Figure 11:
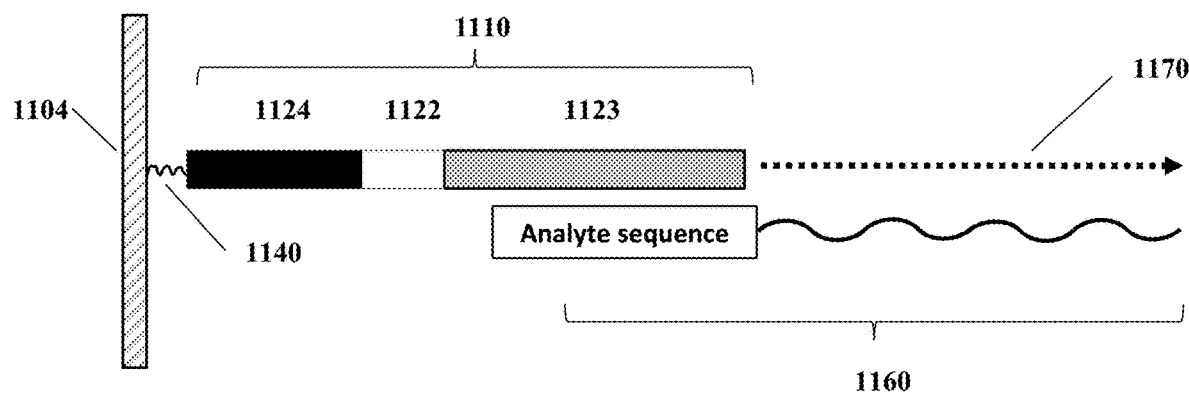
FIG. 11 is a schematic drawing (side view) that illustrates an example of a capture probe attached to a support.

An example barcoded oligonucleotide carried by a bead used in these methods is shown in FIG. 11. In FIG. 11, a barcoded oligonucleotide or capture probe 1110 comprises a barcode sequence 1122 corresponding to a location on a support 1104 to which the oligonucleotide is attached (as illustrated in this example, the oligonucleotide 1110 is attached to the support 1104 via a modification or chemical moiety 1140 capable of attaching to the support 1104). The illustrated oligonucleotide 1110 also comprises a sequence 1123 (i.e., an analyte capture sequence or capture domain) complementary to a sequence of an analyte (e.g., mRNA molecule) 1160 from a biological particle (e.g., cell or nucleus). In some instances, sequence 1123 comprises a sequence specific for an mRNA molecule. In some instances, sequence 1123 comprises a poly(dT) sequence. In some instances, sequence 1123 comprises a defined nucleotide sequence, a semi-random nucleotide sequence or a random nucleotide sequence. Sequence 1123 is hybridized to mRNA molecule 1160 (i.e., the mRNA is captured by the 1123 sequence) and extended via a nucleic acid reaction (e.g., a cDNA molecule 1170 is generated in a reverse transcription reaction) generating a complementary oligonucleotide comprising barcode sequence 1123 (e.g., a spatial barcode sequence, or a reverse complement thereof) and a sequence of the extended nucleic acid (e.g., cDNA 970) (or a portion thereof). A functional sequence 1124, such as a primer binding site for amplification and/or a sequencing related primer binding site (e.g., a sequence used for a sequencing reaction), etc. is also included in the barcoded oligonucleotide or capture probe. In some examples, barcoded nucleic acid molecules can then be optionally processed as described elsewhere herein, e.g., to amplify the molecules and/or append sequencing platform specific sequences to the fragments. Barcoded nucleic acid molecules, or derivatives generated therefrom, can then be sequenced on a suitable sequencing platform. Nucleic acid barcode molecule 1110 may be attached to support 1104 optionally via a releasable linkage 1140 (e.g., comprising a labile bond), such as those described in WO2020/047007A2 (Appl. No. PCT/US2019/048430), WO2020/047010A2 (Appl. No. PCT/US2019/048434), WO2020/047004A3 (Appl. No. PCT/US2019/048427), and WO2020/047005A1 (PCT/US2019/048428), each of which are incorporated by reference herein in their entirety.

Figure 12:
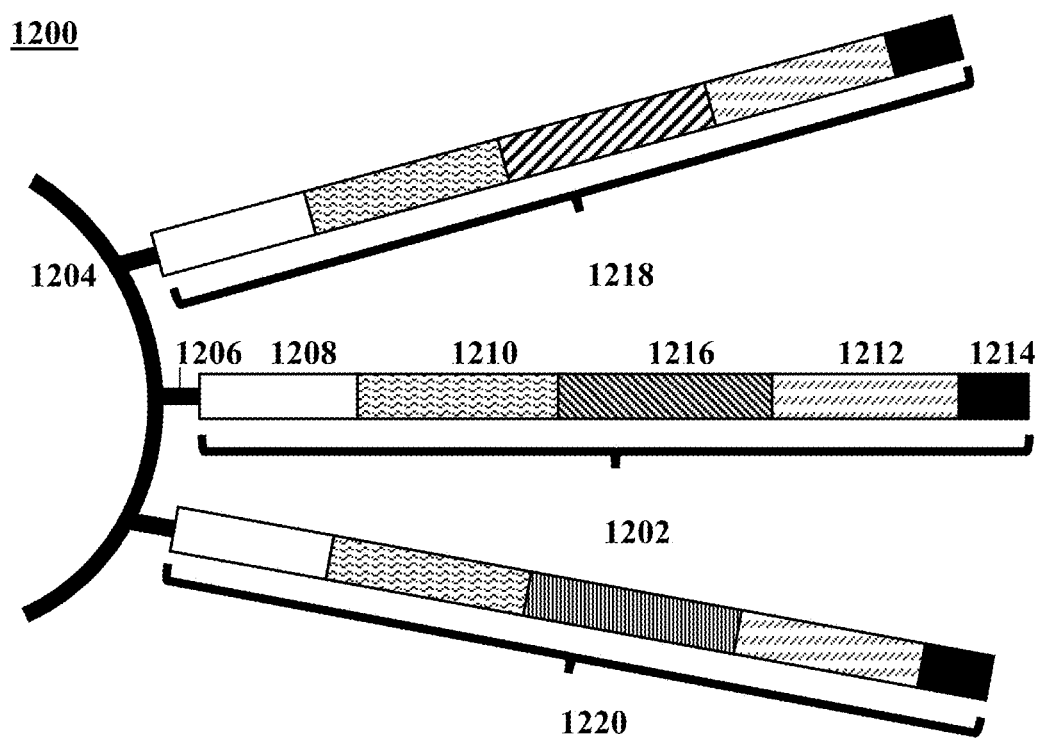
FIG. 12 illustrates an example of a barcode carrying bead.

FIG. 12 illustrates an example of a barcode carrying bead. A nucleic acid molecule 1202, such as an oligonucleotide, can be coupled to a bead 1204 by a releasable linkage 1206, such as, for example, a disulfide linker. The same bead 1204 may be coupled (e.g., via releasable linkage) to one or more other nucleic acid molecules 1218, 1220. The nucleic acid molecule 1202 may be or comprise a barcode. As noted elsewhere herein, the structure of the barcode may comprise several sequence elements. The nucleic acid molecule 1202 may comprise a functional sequence 1208 that may be used in subsequent processing. For example, the functional sequence 1208 may include one or more of a sequencer specific flow cell attachment sequence (e.g., a P5 sequence for Illumina® sequencing systems) and a sequencing primer sequence (e.g., a R1 primer for Illumina® sequencing systems), or partial sequence(s) thereof. The nucleic acid molecule 1202 may comprise a barcode sequence 1210 for use in barcoding the sample (e.g., DNA, RNA, protein, etc.). In some cases, the barcode sequence 1210 can be bead-specific such that the barcode sequence 1210 is common to all nucleic acid molecules (e.g., including nucleic acid molecule 1202) coupled to the same bead 1204. Alternatively, or in addition, the barcode sequence 1210 can be partition-specific such that the barcode sequence 1210 is common to all nucleic acid molecules coupled to one or more beads that are partitioned into the same partition. The nucleic acid molecule 1202 may comprise a specific priming sequence 1212, such as an mRNA specific priming sequence (e.g., poly-T sequence), a targeted priming sequence, and/or a random priming sequence. The nucleic acid molecule 1202 may comprise an anchoring sequence 1214 to ensure that the specific priming sequence 1212 hybridizes at the sequence end (e.g., of the mRNA). For example, the anchoring sequence 1214 can include a random short sequence of nucleotides, such as a 1-mer, 2-mer, 3-mer or longer sequence, which can ensure that a poly-T segment is more likely to hybridize at the sequence end of the poly-A tail of the mRNA.

The nucleic acid molecule 1202 may comprise a unique molecular identifying sequence 1216 (e.g., unique molecular identifier (UMI)). In some cases, the unique molecular identifying sequence 1216 may comprise from about 5 to about 3 nucleotides. Alternatively, the unique molecular identifying sequence 1216 may compress less than about 5 or more than about 8 nucleotides. The unique molecular identifying sequence 1216 may be a unique sequence that varies across individual nucleic acid molecules (e.g., 1202, 1218, 1220, etc.) coupled to a single bead (e.g., bead 1204). In some cases, the unique molecular identifying sequence 1216 may be a random sequence (e.g., such as a random N-mer sequence). For example, the UMI may provide a unique identifier of the starting mRNA molecule that was captured, to allow quantitation of the number of original expressed RNA. As will be appreciated, although FIG. 12 shows three nucleic acid molecules 1202, 1218, 1220 coupled to the surface of the bead 1204, an individual bead may be coupled to any number of individual nucleic acid molecules, for example, from one to tens to hundreds of thousands or even millions of individual nucleic acid molecules. The respective barcodes for the individual nucleic acid molecules can comprise both common sequence segments or relatively common sequence segments (e.g., 1208, 1210, 1212, etc.) and variable or unique sequence segments (e.g., 1216) between different individual nucleic acid molecules coupled to the same bead.

In operation, a biological particle (e.g., cell, nucleus, DNA, RNA, etc.) can be co-partitioned along with a barcode bearing bead 1204. The barcoded nucleic acid molecules 1202, 1218, 1220 can be released from the bead 1204 in the partition. By way of example, in the context of analyzing sample RNA, the poly-T segment (e.g., 1212) of one of the released nucleic acid molecules (e.g., 1202) can hybridize to the poly-A tail of a mRNA molecule. Reverse transcription may result in a cDNA transcript of the mRNA, but which transcript includes each of the sequence segments 1208, 1210, 1216 of the nucleic acid molecule 1202. Because the nucleic acid molecule 1202 comprises an anchoring sequence 1214, it will more likely hybridize to and prime reverse transcription at the sequence end of the poly-A tail of the mRNA. Within any given partition, all the cDNA transcripts of the individual mRNA molecules may include a common barcode sequence segment 1210. However, the transcripts made from the different mRNA molecules within a given partition may vary at the unique molecular identifying sequence 1216 segment (e.g., UMI segment). Beneficially, even following any subsequent amplification of the contents of a given partition, the number of different UMIs can be indicative of the quantity of mRNA originating from a given partition, and thus from the biological particle (e.g., cell or nucleus). As noted above, the transcripts can be amplified, cleaned up and sequenced to identify the sequence of the cDNA transcript of the mRNA, as well as to sequence the barcode segment and the UMI segment. While a poly-T primer sequence is described, other targeted or random priming sequences may also be used in priming the reverse transcription reaction. Likewise, although described as releasing the barcoded oligonucleotides into the partition, in some cases, the nucleic acid molecules bound to the bead (e.g., gel bead) may be used to hybridize and capture the mRNA on the solid phase of the bead, for example, in order to facilitate the separation of the RNA from other cell or nucleus contents.

In some instances, a bead may comprise a capture sequence or binding sequence configured to bind to a corresponding capture sequence or binding sequence. In some instances, a bead may comprise a plurality of different capture sequences or binding sequences configured to bind to different respective corresponding capture sequences or binding sequences. For example, a bead may comprise a first subset of one or more capture sequences each configured to bind to a first corresponding capture sequence, a second subset of one or more capture sequences each configured to bind to a second corresponding capture sequence, a third subset of one or more capture sequences each configured to bind to a third corresponding capture sequence, and etc. A bead may comprise any number of different capture sequences. In some instances, a bead may comprise at least 2, 3, 4, 5, 6, 7, 8, 9, 10 or more different capture sequences or binding sequences configured to bind to different respective capture sequences or binding sequences, respectively. Alternatively, or in addition, a bead may comprise at most about 10, 9, 8, 7, 6, 5, 4, 3, or 2 different capture sequences or binding sequences configured to bind to different respective capture sequences or binding sequences. In some instances, the different capture sequences or binding sequences may be configured to facilitate analysis of a same type of analyte. In some instances, the different capture sequences or binding sequences may be configured to facilitate analysis of different types of analytes (with the same bead). The capture sequence may be designed to attach to a corresponding capture sequence. Beneficially, such corresponding capture sequence may be introduced to, or otherwise induced in, a biological particle (e.g., cell, nucleus, cell bead, etc.) for performing different assays in various formats (e.g., barcoded antibodies comprising the corresponding capture sequence, barcoded MHC dextramers comprising the corresponding capture sequence, barcoded guide RNA molecules comprising the corresponding capture sequence, etc.), such that the corresponding capture sequence may later interact with the capture sequence associated with the bead. In some instances, a capture sequence coupled to a bead (or other support) may be configured to attach to a linker molecule, such as a splint molecule, wherein the linker molecule is configured to couple the bead (or other support) to other molecules through the linker molecule, such as to one or more analytes or one or more other linker molecules.

Figure 13:
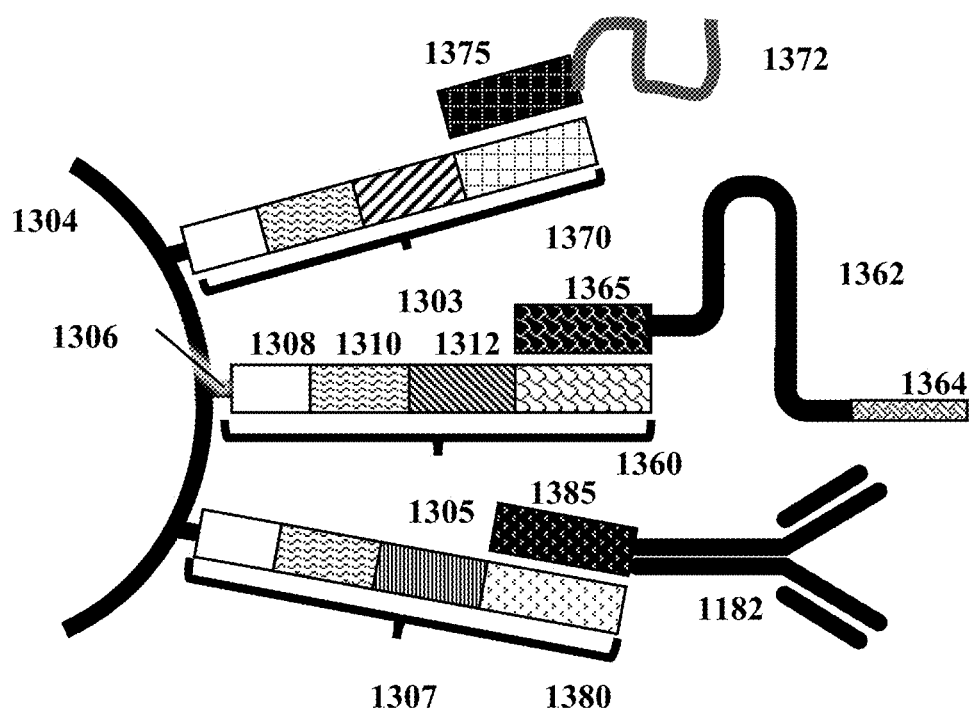
FIG. 13 illustrates another example of a barcode carrying bead.

FIG. 13 illustrates another example of a barcode carrying bead. A nucleic acid molecule 1305, such as an oligonucleotide, can be coupled to a bead 1304 by a releasable linkage 1306, such as, for example, a disulfide linker. The nucleic acid molecule 1305 may comprise a first capture sequence 1360. The same bead 1304 may be coupled (e.g., via releasable linkage) to one or more other nucleic acid molecules 1303, 1307 comprising other capture sequences. The nucleic acid molecule 1305 may be or comprise a barcode. As noted elsewhere herein, the structure of the barcode may comprise a number of sequence elements, such as a functional sequence 1308 (e.g., flow cell attachment sequence, sequencing primer sequence, etc.), a barcode sequence 1310 (e.g., bead-specific sequence common to bead, partition-specific sequence common to partition, etc.), and a unique molecular identifier 1312 (e.g., unique sequence within different molecules attached to the bead), or partial sequences thereof. The capture sequence 1360 may be configured to attach to a corresponding capture sequence 1365. In some instances, the corresponding capture sequence 1365 may be coupled to another molecule that may be an analyte or an intermediary carrier. For example, as illustrated in FIG. 13, the corresponding capture sequence 1365 is coupled to a guide RNA molecule 1362 comprising a target sequence 1364, wherein the target sequence 1364 is configured to attach to the analyte. Another oligonucleotide molecule 1307 attached to the bead 1304 comprises a second capture sequence 1380 which is configured to attach to a second corresponding capture sequence 1385. As illustrated in FIG. 13, the second corresponding capture sequence 1385 is coupled to an antibody 1382. In some cases, the antibody 1382 may have binding specificity to an analyte (e.g., surface protein). Alternatively, the antibody 1382 may not have binding specificity. Another oligonucleotide molecule 1303 attached to the bead 1304 comprises a third capture sequence 1370 which is configured to attach to a second corresponding capture sequence 1375. As illustrated in FIG. 13, the third corresponding capture sequence 1375 is coupled to a molecule 1372. The molecule 1372 may or may not be configured to target an analyte. The other oligonucleotide molecules 1303, 1307 may comprise the other sequences (e.g., functional sequence, barcode sequence, UMI, etc.) described with respect to oligonucleotide molecule 1305. While a single oligonucleotide molecule comprising each capture sequence is illustrated in FIG. 13, it will be appreciated that, for each capture sequence, the bead may comprise a set of one or more oligonucleotide molecules each comprising the capture sequence. For example, the bead may comprise any number of sets of one or more different capture sequences. Alternatively, or in addition, the bead 1304 may comprise other capture sequences. Alternatively, or in addition, the bead 1304 may comprise fewer types of capture sequences (e.g., two capture sequences). Alternatively or in addition, the bead 1304 may comprise oligonucleotide molecule(s) comprising a priming sequence, such as a specific priming sequence such as an mRNA specific priming sequence (e.g., poly-T sequence), a targeted priming sequence, and/or a random priming sequence, for example, to facilitate an assay for gene expression.

In operation, the barcoded oligonucleotides may be released (e.g., in a partition), as described elsewhere herein. Alternatively, the nucleic acid molecules bound to the bead (e.g., gel bead) may be used to hybridize and capture analytes (e.g., one or more types of analytes) on the solid phase of the bead.

In some cases, precursors comprising a functional group that is reactive or capable of being activated such that it becomes reactive can be polymerized with other precursors to generate gel beads comprising the activated or activatable functional group. The functional group may then be used to attach additional species (e.g., disulfide linkers, primers, other oligonucleotides, etc.) to the gel beads. For example, some precursors comprising a carboxylic acid (COOH) group can co-polymerize with other precursors to form a gel bead that also comprises a COOH functional group. In some cases, acrylic acid (a species comprising free COOH groups), acrylamide, and bis(acryloyl)cystamine can be co-polymerized together to generate a gel bead comprising free COOH groups. The COOH groups of the gel bead can be activated (e.g., via 1-Ethyl-3-(3-dimethylaminopropyl)carbodiimide (EDC) and N-Hydroxysuccinimide (NHS) or 4-(4,6-Dimethoxy-1,3,5-triazin-2-yl)-4-methylmorpholinium chloride (DMTMM)) such that they are reactive (e.g., reactive to amine functional groups where EDC/NHS or DMTMM are used for activation). The activated COOH groups can then react with an appropriate species (e.g., a species comprising an amine functional group where the carboxylic acid groups are activated to be reactive with an amine functional group) comprising a moiety to be linked to the bead.

Beads comprising disulfide linkages in their polymeric network may be functionalized with additional species via reduction of some of the disulfide linkages to free thiols. The disulfide linkages may be reduced via, for example, the action of a reducing agent (e.g., DTT, TCEP, etc.) to generate free thiol groups, without dissolution of the bead. Free thiols of the beads can then react with free thiols of a species or a species comprising another disulfide bond (e.g., via thiol-disulfide exchange) such that the species can be linked to the beads (e.g., via a generated disulfide bond). In some cases, free thiols of the beads may react with any other suitable group. For example, free thiols of the beads may react with species comprising an acrydite moiety. The free thiol groups of the beads can react with the acrydite via Michael addition chemistry, such that the species comprising the acrydite is linked to the bead. In some cases, uncontrolled reactions can be prevented by inclusion of a thiol capping agent such as N-ethylmalieamide or iodoacetate.

Activation of disulfide linkages within a bead can be controlled such that only a small number of disulfide linkages are activated. Control may be exerted, for example, by controlling the concentration of a reducing agent used to generate free thiol groups and/or concentration of reagents used to form disulfide bonds in bead polymerization. In some cases, a low concentration (e.g., molecules of reducing agent:gel bead ratios of less than or equal to about 1:100,000,000,000, less than or equal to about 1:10,000,000,000, less than or equal to about 1:1,000,000,000, less than or equal to about 1:100,000,000, less than or equal to about 1:10,000,000, less than or equal to about 1:1,000,000, less than or equal to about 1:100,000, less than or equal to about 1:10,000) of reducing agent may be used for reduction. Controlling the number of disulfide linkages that are reduced to free thiols may be useful in ensuring bead structural integrity during functionalization. In some cases, optically-active agents, such as fluorescent dyes may be coupled to beads via free thiol groups of the beads and used to quantify the number of free thiols present in a bead and/or track a bead.

In some cases, addition of moieties to a gel bead after gel bead formation may be advantageous. For example, addition of an oligonucleotide (e.g., barcoded oligonucleotide) after gel bead formation may avoid loss of the species during chain transfer termination that can occur during polymerization. Moreover, smaller precursors (e.g., monomers or cross linkers that do not comprise side chain groups and linked moieties) may be used for polymerization and can be minimally hindered from growing chain ends due to viscous effects. In some cases, functionalization after gel bead synthesis can minimize exposure of species (e.g., oligonucleotides) to be loaded with potentially damaging agents (e.g., free radicals) and/or chemical environments. In some cases, the generated gel may possess an upper critical solution temperature (UCST) that can permit temperature driven swelling and collapse of a bead. Such functionality may aid in oligonucleotide (e.g., a primer) infiltration into the bead during subsequent functionalization of the bead with the oligonucleotide. Post-production functionalization may also be useful in controlling loading ratios of species in beads, such that, for example, the variability in loading ratio is minimized. Species loading may also be performed in a batch process such that a plurality of beads can be functionalized with the species in a single batch.

A bead injected or otherwise introduced into a partition may comprise releasably, cleavably, or reversibly attached barcodes. A bead injected or otherwise introduced into a partition may comprise activatable barcodes. A bead injected or otherwise introduced into a partition may be degradable, disruptable, or dissolvable beads.

Barcodes can be releasably, cleavably or reversibly attached to the beads such that barcodes can be released or be releasable through cleavage of a linkage between the barcode molecule and the bead, or released through degradation of the underlying bead itself, allowing the barcodes to be accessed or be accessible by other reagents, or both.

In non-limiting examples, cleavage may be achieved through reduction of di-sulfide bonds, use of restriction enzymes, photo-activated cleavage, or cleavage via other types of stimuli (e.g., chemical, thermal, pH, enzymatic, etc.) and/or reactions, such as described elsewhere herein. Releasable barcodes may sometimes be referred to as being activatable, in that they are available for reaction once released. Thus, for example, an activatable barcode may be activated by releasing the barcode from a bead (or other suitable type of partition described herein). Other activatable configurations are also envisioned in the context of the described methods and systems.

In addition to, or as an alternative to the cleavable linkages between the beads and the associated molecules, such as barcode containing nucleic acid molecules (e.g., barcoded oligonucleotides), the beads may be degradable, disruptable, or dissolvable spontaneously or upon exposure to one or more stimuli (e.g., temperature changes, pH changes, exposure to particular chemical species or phase, exposure to light, reducing agent, etc.). In some cases, a bead may be dissolvable, such that material components of the beads are solubilized when exposed to a particular chemical species or an environmental change, such as a change temperature or a change in pH. In some cases, a gel bead can be degraded or dissolved at elevated temperature and/or in basic conditions. In some cases, a bead may be thermally degradable such that when the bead is exposed to an appropriate change in temperature (e.g., heat), the bead degrades. Degradation or dissolution of a bead bound to a species (e.g., a nucleic acid molecule, e.g., barcoded oligonucleotide) may result in release of the species from the bead.

As will be appreciated from the above disclosure, the degradation of a bead may refer to the disassociation of a bound or entrained species from a bead, both with and without structurally degrading the physical bead itself. For example, the degradation of the bead may involve cleavage of a cleavable linkage via one or more species and/or methods described elsewhere herein. In another example, entrained species may be released from beads through osmotic pressure differences due to, for example, changing chemical environments. By way of example, alteration of bead pore sizes due to osmotic pressure differences can generally occur without structural degradation of the bead itself. In some cases, an increase in pore size due to osmotic swelling of a bead can permit the release of entrained species within the bead. In other cases, osmotic shrinking of a bead may cause a bead to better retain an entrained species due to pore size contraction.

A degradable bead may be introduced into a partition, such as a droplet of an emulsion or a well, such that the bead degrades within the partition and any associated species (e.g., oligonucleotides) are released within the droplet when the appropriate stimulus is applied. The free species (e.g., oligonucleotides, nucleic acid molecules) may interact with other reagents contained in the partition. For example, a polyacrylamide bead comprising cystamine and linked, via a disulfide bond, to a barcode sequence, may be combined with a reducing agent within a droplet of a water-in-oil emulsion. Within the droplet, the reducing agent can break the various disulfide bonds, resulting in bead degradation and release of the barcode sequence into the aqueous, inner environment of the droplet. In another example, heating of a droplet comprising a bead-bound barcode sequence in basic solution may also result in bead degradation and release of the attached barcode sequence into the aqueous, inner environment of the droplet.

Any suitable number of molecular tag molecules (e.g., primer, barcoded oligonucleotide) can be associated with a bead such that, upon release from the bead, the molecular tag molecules (e.g., primer, e.g., barcoded oligonucleotide) are present in the partition at a pre-defined concentration. Such pre-defined concentration may be selected to facilitate certain reactions for generating a sequencing library, e.g., amplification, within the partition. In some cases, the pre-defined concentration of the primer can be limited by the process of producing nucleic acid molecule (e.g., oligonucleotide) bearing beads.

In some cases, beads can be non-covalently loaded with one or more reagents. The beads can be non-covalently loaded by, for instance, subjecting the beads to conditions sufficient to swell the beads, allowing sufficient time for the reagents to diffuse into the interiors of the beads, and subjecting the beads to conditions sufficient to de-swell the beads. The swelling of the beads may be accomplished, for instance, by placing the beads in a thermodynamically favorable solvent, subjecting the beads to a higher or lower temperature, subjecting the beads to a higher or lower ion concentration, and/or subjecting the beads to an electric field. The swelling of the beads may be accomplished by various swelling methods. The de-swelling of the beads may be accomplished, for instance, by transferring the beads in a thermodynamically unfavorable solvent, subjecting the beads to lower or high temperatures, subjecting the beads to a lower or higher ion concentration, and/or removing an electric field. The de-swelling of the beads may be accomplished by various de-swelling methods. Transferring the beads may cause pores in the bead to shrink. The shrinking may then hinder reagents within the beads from diffusing out of the interiors of the beads. The hindrance may be due to steric interactions between the reagents and the interiors of the beads. The transfer may be accomplished microfluidically. For instance, the transfer may be achieved by moving the beads from one co-flowing solvent stream to a different co-flowing solvent stream. The swellability and/or pore size of the beads may be adjusted by changing the polymer composition of the bead.

In some cases, an acrydite moiety linked to a precursor, another species linked to a precursor, or a precursor itself can comprise a labile bond, such as chemically, thermally, or photo-sensitive bond e.g., disulfide bond, UV sensitive bond, or the like. Once acrydite moieties or other moieties comprising a labile bond are incorporated into a bead, the bead may also comprise the labile bond. The labile bond may be, for example, useful in reversibly linking (e.g., covalently linking) species (e.g., barcodes, primers, etc.) to a bead. In some cases, a thermally labile bond may include a nucleic acid hybridization based attachment, e.g., where an oligonucleotide is hybridized to a complementary sequence that is attached to the bead, such that thermal melting of the hybrid releases the oligonucleotide, e.g., a barcode containing sequence, from the support (e.g., bead).

The addition of multiple types of labile bonds to a gel bead may result in the generation of a bead capable of responding to varied stimuli. Each type of labile bond may be sensitive to an associated stimulus (e.g., chemical stimulus, light, temperature, enzymatic, etc.) such that release of species attached to a bead via each labile bond may be controlled by the application of the appropriate stimulus. Such functionality may be useful in controlled release of species from a gel bead. In some cases, another species comprising a labile bond may be linked to a gel bead after gel bead formation via, for example, an activated functional group of the gel bead as described above. As will be appreciated, barcodes that are releasably, cleavably or reversibly attached to the beads described herein include barcodes that are released or releasable through cleavage of a linkage between the barcode molecule and the bead, or that are released through degradation of the underlying bead itself, allowing the barcodes to be accessed or accessible by other reagents, or both.

In some cases, a species (e.g., oligonucleotide molecules comprising barcodes) that are attached to a solid support (e.g., a bead) may comprise a U-excising element that allows the species to release from the bead. In some cases, the U-excising element may comprise a single-stranded DNA (ssDNA) sequence that contains at least one uracil. The species may be attached to a solid support via the ssDNA sequence containing the at least one uracil. The species may be released by a combination of uracil-DNA glycosylase (e.g., to remove the uracil) and an endonuclease (e.g., to induce an ssDNA break). If the endonuclease generates a 5' phosphate group from the cleavage, then additional enzyme treatment may be included in downstream processing to eliminate the phosphate group, e.g., prior to ligation of additional sequencing handle elements, e.g., Illumina full P5 sequence, partial P5 sequence, full R1 sequence, and/or partial R1 sequence.

The barcodes that are releasable as described herein may sometimes be referred to as being activatable, in that they are available for reaction once released. Thus, for example, an activatable barcode may be activated by releasing the barcode from a bead (or other suitable type of partition described herein). Other activatable configurations are also envisioned in the context of the described methods and systems.

In addition to thermally cleavable bonds, disulfide bonds and UV sensitive bonds, other non-limiting examples of labile bonds that may be coupled to a precursor or bead include an ester linkage (e.g., cleavable with an acid, a base, or hydroxylamine), a vicinal diol linkage (e.g., cleavable via sodium periodate), a Diels-Alder linkage (e.g., cleavable via heat), a sulfone linkage (e.g., cleavable via a base), a silyl ether linkage (e.g., cleavable via an acid), a glycosidic linkage (e.g., cleavable via an amylase), a peptide linkage (e.g., cleavable via a protease), or a phosphodiester linkage (e.g., cleavable via a nuclease; e.g., DNase). A bond may be cleavable via other nucleic acid molecule targeting enzymes, such as restriction enzymes (e.g., restriction endonucleases), as described further below.

Species may be encapsulated in beads during bead generation (e.g., during polymerization of precursors). Such species may or may not participate in polymerization. Such species may be entered into polymerization reaction mixtures such that generated beads comprise the species upon bead formation. In some cases, such species may be added to the gel beads after formation. Such species may include, for example, nucleic acid molecules (e.g., oligonucleotides), reagents for a nucleic acid amplification reaction (e.g., primers, polymerases, dNTPs, co-factors (e.g., ionic co-factors), buffers) including those described herein, reagents for enzymatic reactions (e.g., enzymes, co-factors, substrates, buffers), reagents for nucleic acid modification reactions such as polymerization, ligation, or digestion, and/or reagents for template preparation (e.g., tagmentation) for one or more sequencing platforms (e.g., Nextera® for Illumina®). Such species may include one or more enzymes described herein, including without limitation, polymerase, reverse transcriptase, restriction enzymes (e.g., endonuclease), transposase, ligase, proteinase K, DNase, etc. Such species may include one or more reagents described elsewhere herein (e.g., lysis agents, inhibitors, inactivating agents, chelating agents, stimulus). Trapping of such species may be controlled by the polymer network density generated during polymerization of precursors, control of ionic charge within the gel bead (e.g., via ionic species linked to polymerized species), or by the release of other species. Encapsulated species may be released from a bead upon bead degradation and/or by application of a stimulus capable of releasing the species from the bead. Alternatively, or in addition, species may be partitioned in a partition (e.g., droplet) during or after partition formation. Such species may include, without limitation, the abovementioned species that may also be encapsulated in a bead.

A degradable bead may comprise one or more species with a labile bond such that, when the bead/species is exposed to the appropriate stimuli, the bond is broken, and the bead degrades. The labile bond may be a chemical bond (e.g., covalent bond, ionic bond) or may be another type of physical interaction (e.g., van der Waals interactions, dipole-dipole interactions, etc.). In some cases, a crosslinker used to generate a bead may comprise a labile bond. Upon exposure to the appropriate conditions, the labile bond can be broken, and the bead degraded. For example, upon exposure of a polyacrylamide gel bead comprising cystamine crosslinkers to a reducing agent, the disulfide bonds of the cystamine can be broken and the bead degraded.

A degradable bead may be useful in more quickly releasing an attached species (e.g., a nucleic acid molecule, a barcode sequence, a primer, etc.) from the bead when the appropriate stimulus is applied to the bead as compared to a bead that does not degrade. For example, for a species bound to an inner surface of a porous bead or in the case of an encapsulated species, the species may have greater mobility and accessibility to other species in solution upon degradation of the bead. In some cases, a species may also be attached to a degradable bead via a degradable linker (e.g., disulfide linker). The degradable linker may respond to the same stimuli as the degradable bead or the two degradable species may respond to different stimuli. For example, a barcode sequence may be attached, via a disulfide bond, to a polyacrylamide bead comprising cystamine. Upon exposure of the barcoded bead to a reducing agent, the bead degrades, and the barcode sequence is released upon breakage of both the disulfide linkage between the barcode sequence and the bead and the disulfide linkages of the cystamine in the bead.

As will be appreciated from the above disclosure, while referred to as degradation of a bead, in many instances as noted above, that degradation may refer to the disassociation of a bound or entrained species from a bead, both with and without structurally degrading the physical bead itself. For example, entrained species may be released from beads through osmotic pressure differences due to, for example, changing chemical environments. By way of example, alteration of bead pore sizes due to osmotic pressure differences can generally occur without structural degradation of the bead itself. In some cases, an increase in pore size due to osmotic swelling of a bead can permit the release of entrained species within the bead. In other cases, osmotic shrinking of a bead may cause a bead to better retain an entrained species due to pore size contraction.

Where degradable beads are provided, it may be beneficial to avoid exposing such beads to the stimulus or stimuli that cause such degradation prior to a given time, in order to, for example, avoid premature bead degradation and issues that arise from such degradation, including for example poor flow characteristics and aggregation. By way of example, where beads comprise reducible cross-linking groups, such as disulfide groups, it will be desirable to avoid contacting such beads with reducing agents, e.g., DTT or other disulfide cleaving reagents. In such cases, treatment to the beads described herein will, in some cases be provided free of reducing agents, such as DTT. Because reducing agents are often provided in commercial enzyme preparations, it may be desirable to provide reducing agent free (or DTT free) enzyme preparations in treating the beads described herein. Examples of such enzymes include, e.g., polymerase enzyme preparations, reverse transcriptase enzyme preparations, ligase enzyme preparations, as well as many other enzyme preparations that may be used to treat the beads described herein. The terms "reducing agent free" or "DTT free" preparations can refer to a preparation having less than about 1/10th, less than about 1/50th, or even less than about 1/100th of the lower ranges for such materials used in degrading the beads. For example, for DTT, the reducing agent free preparation can have less than about 0.01 millimolar (mM), 0.005 mM, 0.001 mM DTT, 0.0005 mM DTT, or even less than about 0.0001 mM DTT. In many cases, the amount of DTT can be undetectable.

Numerous chemical triggers may be used to trigger the degradation of beads. Examples of these chemical changes may include but are not limited to pH-mediated changes to the integrity of a component within the bead, degradation of a component of a bead via cleavage of cross-linked bonds, and depolymerization of a component of a bead.

In some embodiments, a bead may be formed from materials that comprise degradable chemical crosslinkers, such as BAC or cystamine. Degradation of such degradable crosslinkers may be accomplished through several mechanisms. In some examples, a bead may be contacted with a chemical degrading agent that may induce oxidation, reduction, or other chemical changes. For example, a chemical degrading agent may be a reducing agent, such as dithiothreitol (DTT). Additional examples of reducing agents may include β-mercaptoethanol, (2S)-2-amino-1,4-dimercaptobutane (dithiobutylamine or DTBA), tris(2-carboxyethyl) phosphine (TCEP), or combinations thereof. A reducing agent may degrade the disulfide bonds formed between gel precursors forming the bead, and thus, degrade the bead. In other cases, a change in pH of a solution, such as an increase in pH, may trigger degradation of a bead. In other cases, exposure to an aqueous solution, such as water, may trigger hydrolytic degradation, and thus degradation of the bead. In some cases, any combination of stimuli may trigger degradation of a bead. For example, a change in pH may enable a chemical agent (e.g., DTT) to become an effective reducing agent.

Beads may also be induced to release their contents upon the application of a thermal stimulus. A change in temperature can cause a variety of changes to a bead. For example, heat can cause a solid bead to liquefy. A change in heat may cause melting of a bead such that a portion of the bead degrades. In other cases, heat may increase the internal pressure of the bead components such that the bead ruptures or explodes. Heat may also act upon heat-sensitive polymers used as materials to construct beads.

Any suitable agent may degrade beads. In some embodiments, changes in temperature or pH may be used to degrade thermo-sensitive or pH-sensitive bonds within beads. In some embodiments, chemical degrading agents may be used to degrade chemical bonds within beads by oxidation, reduction, or other chemical changes. For example, a chemical degrading agent may be a reducing agent, such as DTT, wherein DTT may degrade the disulfide bonds formed between a crosslinker and gel precursors, thus degrading the bead. In some embodiments, a reducing agent may be added to degrade the bead, which may or may not cause the bead to release its contents. Examples of reducing agents may include dithiothreitol (DTT), β-mercaptoethanol, (2S)-2-amino-1,4-dimercaptobutane (dithiobutylamine or DTBA), tris(2-carboxyethyl) phosphine (TCEP), or combinations thereof. The reducing agent may be present at a concentration of about 0.1 mM, 0.5 mM, 1 mM, 5 mM, 10 mM. The reducing agent may be present at a concentration of at least about 0.1 mM, 0.5 mM, 1 mM, 5 mM, 10 mM, or greater than 10 mM. The reducing agent may be present at concentration of at most about 10 mM, 5 mM, 1 mM, 0.5 mM, 0.1 mM, or less.

Any suitable number of molecular tag molecules (e.g., primer, barcoded oligonucleotide) can be associated with a bead such that, upon release from the bead, the molecular tag molecules (e.g., primer, e.g., barcoded oligonucleotide) are present in the partition at a pre-defined concentration. Such pre-defined concentration may be selected to facilitate certain reactions for generating a sequencing library, e.g., amplification, within the partition. In some cases, the pre-defined concentration of the primer can be limited by the process of producing oligonucleotide bearing beads.

Although FIG. 5 and FIG. 7 have been described in terms of providing substantially singly occupied partitions, above, in certain cases, it may be desirable to provide multiply occupied partitions, e.g., containing two, three, four or more cells or nuclei and/or supports (e.g., beads) comprising barcoded nucleic acid molecules (e.g., oligonucleotides) within a single partition. Accordingly, as noted above, the flow characteristics of the biological particle and/or bead containing fluids and partitioning fluids may be controlled to provide for such multiply occupied partitions. In particular, the flow parameters may be controlled to provide a given occupancy rate at greater than about 50% of the partitions, greater than about 75%, and in some cases greater than about 80%, 90%, 95%, or higher.

In some cases, additional supports (e.g., beads) can be used to deliver additional reagents to a partition. In such cases, it may be advantageous to introduce different beads into a common channel or droplet generation junction, from different bead sources (e.g., containing different associated reagents) through different channel inlets into such common channel or droplet generation junction (e.g., junction 510). In such cases, the flow and frequency of the different beads into the channel or junction may be controlled to provide for a certain ratio of beads from each source, while ensuring a given pairing or combination of such beads into a partition with a given number of biological particles (e.g., one biological particle and one bead per partition).

The partitions described herein may comprise small volumes, for example, less than about 10 microliters (μL), 5 μL, 1 μL, 900 picoliters (pL), 800 pL, 700 pL, 600 pL, 500 pL, 400 pL, 300 pL, 200 pL, 100 pL, 50 pL, 20 pL, 10 pL, 1 pL, 500 nanoliters (nL), 100 nL, 50 nL, or less.

For example, in the case of droplet based partitions, the droplets may have overall volumes that are less than about 1000 pL, 900 pL, 800 pL, 700 pL, 600 pL, 500 pL, 400 pL, 300 pL, 200 pL, 100 pL, 50 pL, 20 pL, 10 pL, 1 pL, or less. Where co-partitioned with supports (e.g., beads), it will be appreciated that the sample fluid volume, e.g., including co-partitioned biological particles and/or beads, within the partitions may be less than about 90% of the above described volumes, less than about 80%, less than about 70%, less than about 60%, less than about 50%, less than about 40%, less than about 30%, less than about 20%, or less than about 10% of the above described volumes.

As is described elsewhere herein, partitioning species may generate a population or plurality of partitions. In such cases, any suitable number of partitions can be generated or otherwise provided. For example, at least about 1,000 partitions, at least about 5,000 partitions, at least about 10,000 partitions, at least about 50,000 partitions, at least about 100,000 partitions, at least about 500,000 partitions, at least about 1,000,000 partitions, at least about 5,000,000 partitions at least about 10,000,000 partitions, at least about 50,000,000 partitions, at least about 100,000,000 partitions, at least about 500,000,000 partitions, at least about 1,000,000,000 partitions, or more partitions can be generated or otherwise provided. Moreover, the plurality of partitions may comprise both unoccupied partitions (e.g., empty partitions) and occupied partitions.

Reagents

In accordance with certain aspects, biological particles may be partitioned along with lysis reagents to release the contents of the biological particles within the partition. In such cases, the lysis agents can be contacted with the biological particle suspension concurrently with, or immediately prior to, the introduction of the biological particles into the partitioning junction/droplet generation zone (e.g., junction 510 in FIG. 5), such as through an additional channel or channels upstream of the channel junction. In accordance with other aspects, additionally or alternatively, biological particles may be partitioned along with other reagents, as will be described further below.

Beneficially, when lysis reagents and biological particles are co-partitioned, the lysis reagents can facilitate the release of the contents of the biological particles within the partition. The contents released in a partition may remain discrete from the contents of other partitions.

Examples of lysis agents include bioactive reagents, such as lysis enzymes that are used for lysis of different cell types, e.g., gram positive or negative bacteria, plants, yeast, mammalian, etc., such as lysozymes, achromopeptidase, lysostaphin, labiase, kitalase, lyticase, and a variety of other lysis enzymes available from, e.g., Sigma-Aldrich, Inc. (St Louis, MO), as well as other commercially available lysis enzymes. Other lysis agents may additionally or alternatively be co-partitioned with the biological particles to cause the release of the biological particle's contents into the partitions. For example, in some cases, surfactant-based lysis solutions may be used to lyse cells, although these may be less desirable for emulsion-based systems where the surfactants can interfere with stable emulsions. In some cases, lysis solutions may include non-ionic surfactants such as, for example, TritonX-100 and Tween 20. In some cases, lysis solutions may include ionic surfactants such as, for example, sarcosyl and sodium dodecyl sulfate (SDS). Electroporation, thermal, acoustic or mechanical cellular disruption may also be used in certain cases, e.g., non-emulsion based partitioning such as encapsulation of biological particles that may be in addition to or in place of droplet partitioning, where any pore size of the encapsulate is sufficiently small to retain nucleic acid fragments of a given size, following cellular disruption.

Alternatively or in addition to the lysis agents co-partitioned with the biological particles described above, other reagents can also be co-partitioned with the biological particles, including, for example, DNase and RNase inactivating agents or inhibitors, such as proteinase K, chelating agents, such as EDTA, and other reagents employed in removing or otherwise reducing negative activity or impact of different cell lysate components on subsequent processing of nucleic acids. In addition, in the case of encapsulated biological particles (e.g., a cell or a nucleus in a polymer matrix), the biological particles may be exposed to an appropriate stimulus to release the biological particles or their contents from a co-partitioned support (e.g., bead). For example, in some cases, a chemical stimulus may be co-partitioned along with an encapsulated biological particle to allow for the degradation of the support (e.g., bead) and release of the cell, nucleus or its contents into the larger partition. In some cases, this stimulus may be the same as the stimulus described elsewhere herein for release of nucleic acid molecules (e.g., oligonucleotides) from their respective support (e.g., bead). In alternative examples, this may be a different and non-overlapping stimulus, to allow an encapsulated biological particle to be released into a partition at a different time from the release of nucleic acid molecules into the same partition. For a description of methods, compositions, and systems for encapsulating cells (also referred to as a "cell bead"), see, e.g., U.S. Pat. No. 10,428,326 and U.S. Pat. Pub. 20190100632, which are each incorporated by reference in their entirety.

Additional reagents may also be co-partitioned with the biological particles, such as endonucleases to fragment a biological particle's DNA, DNA polymerase enzymes and dNTPs used to amplify the biological particle's nucleic acid fragments and to attach the barcode molecular tags to the amplified fragments. Other enzymes may be co-partitioned, including without limitation, polymerase, transposase, ligase, proteinase K, DNase, etc. Additional reagents may also include reverse transcriptase enzymes, including enzymes with terminal transferase activity, primers and oligonucleotides, and switch oligonucleotides (also referred to herein as "switch oligos" or "template switching oligonucleotides") which can be used for template switching. In some cases, template switching can be used to increase the length of a cDNA. In some cases, template switching can be used to append a predefined nucleic acid sequence to the cDNA. In an example of template switching, cDNA can be generated from reverse transcription of a template, e.g., cellular mRNA, where a reverse transcriptase with terminal transferase activity can add additional nucleotides, e.g., polyC, to the cDNA in a template independent manner. Switch oligos can include sequences complementary to the additional nucleotides, e.g., polyG. The additional nucleotides (e.g., polyC) on the cDNA can hybridize to the additional nucleotides (e.g., polyG) on the switch oligo, whereby the switch oligo can be used by the reverse transcriptase as template to further extend the cDNA. Template switching oligonucleotides may comprise a hybridization region and a template region. The hybridization region can comprise any sequence capable of hybridizing to the target. In some cases, as previously described, the hybridization region comprises a series of G bases to complement the overhanging C bases at the 3' end of a cDNA molecule. The series of G bases may comprise 1 G base, 2 G bases, 3 G bases, 4 G bases, 5 G bases or more than 5 G bases. The template sequence can comprise any sequence to be incorporated into the cDNA.

In some cases, the template region comprises at least 1 (e.g., at least 2, 3, 4, 5 or more) tag sequences and/or functional sequences. Switch oligos may comprise deoxyribonucleic acids; ribonucleic acids; modified nucleic acids including 2-Aminopurine, 2,6-Diaminopurine (2-Amino-dA), inverted dT, 5-Methyl dC, 2'-deoxyInosine, Super T (5-hydroxybutynl-2'-deoxyuridine), Super G (8-aza-7-deaz-aguanosine), locked nucleic acids (LNAs), unlocked nucleic acids (UNAs, e.g., UNA-A, UNA-U, UNA-C, UNA-G), Iso-dG, Iso-dC, 2' Fluoro bases (e.g., Fluoro C, Fluoro U, Fluoro A, and Fluoro G), or any combination.

In some cases, the length of a switch oligo may be at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249 or 250 nucleotides or longer.

In some cases, the length of a switch oligo may be at most about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249 or 250 nucleotides.

Once the contents of the cells or nuclei are released into their respective partitions, the macromolecular components (e.g., macromolecular constituents of biological particles, such as RNA, DNA, or proteins) contained therein may be further processed within the partitions. In accordance with the methods and systems described herein, the macromolecular component contents of individual biological particles can be provided with unique identifiers such that, upon characterization of those macromolecular components they may be attributed as having been derived from the same biological particle or particles. The ability to attribute characteristics to individual biological particles or groups of biological particles is provided by the assignment of unique identifiers specifically to an individual biological particle or groups of biological particles. Unique identifiers, e.g., in the form of nucleic acid barcodes can be assigned or associated with individual biological particles or populations of biological particles, in order to tag or label the biological particle's macromolecular components (and as a result, its characteristics) with the unique identifiers. These unique identifiers can then be used to attribute the biological particle's components and characteristics to an individual biological particle or group of biological particles.

In some aspects, this is performed by co-partitioning the individual biological particle or groups of biological particles with the unique identifiers, such as described above. In some aspects, the unique identifiers are provided in the form of nucleic acid molecules (e.g., oligonucleotides) that comprise nucleic acid barcode sequences that may be attached to or otherwise associated with the nucleic acid contents of individual biological particle, or to other components of the biological particle, and particularly to fragments of those nucleic acids. The nucleic acid molecules are partitioned such that as between nucleic acid molecules in a given partition, the nucleic acid barcode sequences contained therein are the same, but as between different partitions, the nucleic acid molecule can, and do have differing barcode sequences, or at least represent a large number of different barcode sequences across all of the partitions in a given analysis. In some aspects, only one nucleic acid barcode sequence can be associated with a given partition, although in some cases, two or more different barcode sequences may be present.

The nucleic acid barcode sequences can include from about 6 to about 20 or more nucleotides within the sequence of the nucleic acid molecules (e.g., oligonucleotides). The nucleic acid barcode sequences can include from about 6 to about 20, 30, 40, 50, 60, 70, 80, 90, 100 or more nucleotides. In some cases, the length of a barcode sequence may be about 6, 7, 8, 9, 10, 11, 12, 13, 14, 15, 16, 17, 18, 19, 20 nucleotides or longer. In some cases, the length of a barcode sequence may be at least about 6, 7, 8, 9, 10, 11, 12, 13, 14, 15, 16, 17, 18, 19, 20 nucleotides or longer. In some cases, the length of a barcode sequence may be at most about 6, 7, 8, 9, 10, 11, 12, 13, 14, 15, 16, 17, 18, 19, 20 nucleotides or shorter. These nucleotides may be completely contiguous, i.e., in a single stretch of adjacent nucleotides, or they may be separated into two or more separate subsequences that are separated by 1 or more nucleotides. In some cases, separated barcode subsequences can be from about 4 to about 16 nucleotides in length. In some cases, the barcode subsequence may be about 4, 5, 6, 7, 8, 9, 10, 11, 12, 13, 14, 15, 16 nucleotides or longer. In some cases, the barcode subsequence may be at least about 4, 5, 6, 7, 8, 9, 10, 11, 12, 13, 14, 15, 16 nucleotides or longer. In some cases, the barcode subsequence may be at most about 4, 5, 6, 7, 8, 9, 10, 11, 12, 13, 14, 15, 16 nucleotides or shorter.

The co-partitioned nucleic acid molecules can also comprise other functional sequences useful in the processing of the nucleic acids from the co-partitioned biological particles. These sequences include, e.g., targeted or random/universal amplification primer sequences for amplifying nucleic acids (e.g., mRNA, the genomic DNA) from the individual biological particles within the partitions while attaching the associated barcode sequences, sequencing primers or primer recognition sites, hybridization or probing sequences, e.g., for identification of presence of the sequences or for pulling down barcoded nucleic acids, or any of a number of other potential functional sequences. Other mechanisms of co-partitioning oligonucleotides may also be employed, including, e.g., coalescence of two or more droplets, where one droplet contains oligonucleotides, or microdispensing of oligonucleotides (e.g., attached to a bead) into partitions, e.g., droplets within microfluidic systems.

In an example, supports, such as beads, are provided that each include large numbers of the above described barcoded nucleic acid molecules (e.g., barcoded oligonucleotides) releasably attached to the beads, where all of the nucleic acid molecules attached to a particular bead will include the same nucleic acid barcode sequence, but where a large number of diverse barcode sequences are represented across the population of beads used. In some embodiments, hydrogel beads, e.g., comprising polyacrylamide polymer matrices, are used as a solid support and delivery vehicle for the nucleic acid molecules into the partitions, as they are capable of carrying large numbers of nucleic acid molecules, and may be configured to release those nucleic acid molecules upon exposure to a particular stimulus, as described elsewhere herein. In some cases, the population of beads provides a diverse barcode sequence library that includes at least about 1,000 different barcode sequences, at least about 5,000 different barcode sequences, at least about 10,000 different barcode sequences, at least about 50,000 different barcode sequences, at least about 100,000 different barcode sequences, at least about 1,000,000 different barcode sequences, at least about 5,000,000 different barcode sequences, or at least about 10,000,000 different barcode sequences, or more. Additionally, each bead can be provided with large numbers of nucleic acid (e.g., oligonucleotide) molecules attached. In particular, the number of molecules of nucleic acid molecules including the barcode sequence on an individual bead can be at least about 1,000 nucleic acid molecules, at least about 5,000 nucleic acid molecules, at least about 10,000 nucleic acid molecules, at least about 50,000 nucleic acid molecules, at least about 100,000 nucleic acid molecules, at least about 500,000 nucleic acids, at least about 1,000,000 nucleic acid molecules, at least about 5,000,000 nucleic acid molecules, at least about 10,000,000 nucleic acid molecules, at least about 50,000,000 nucleic acid molecules, at least about 100,000,000 nucleic acid molecules, at least about 250,000,000 nucleic acid molecules and in some cases at least about 1 billion nucleic acid molecules, or more. Nucleic acid molecules of a given bead can include identical (or common) barcode sequences, different barcode sequences, or a combination of both. Nucleic acid molecules of a given bead can include multiple sets of nucleic acid molecules. Nucleic acid molecules of a given set can include identical barcode sequences. The identical barcode sequences can be different from barcode sequences of nucleic acid molecules of another set.

Moreover, when the population of beads is partitioned, the resulting population of partitions can also include a diverse barcode library that includes at least about 1,000 different barcode sequences, at least about 5,000 different barcode sequences, at least about 10,000 different barcode sequences, at least at least about 50,000 different barcode sequences, at least about 100,000 different barcode sequences, at least about 1,000,000 different barcode sequences, at least about 5,000,000 different barcode sequences, or at least about 10,000,000 different barcode sequences. Additionally, each partition of the population can include at least about 1,000 nucleic acid molecules, at least about 5,000 nucleic acid molecules, at least about 10,000 nucleic acid molecules, at least about 50,000 nucleic acid molecules, at least about 100,000 nucleic acid molecules, at least about 500,000 nucleic acids, at least about 1,000,000 nucleic acid molecules, at least about 5,000,000 nucleic acid molecules, at least about 10,000,000 nucleic acid molecules, at least about 50,000,000 nucleic acid molecules, at least about 100,000,000 nucleic acid molecules, at least about 250,000,000 nucleic acid molecules and in some cases at least about 1 billion nucleic acid molecules.

In some cases, it may be desirable to incorporate multiple different barcodes within a given partition, either attached to single or multiple beads within the partition. For example, in some cases, a mixed, but known set of barcode sequences may provide greater assurance of identification in the subsequent processing, e.g., by providing a stronger address or attribution of the barcodes to a given partition, as a duplicate or independent confirmation of the output from a given partition.

The nucleic acid molecules (e.g., oligonucleotides) are releasable from the beads upon the application of a particular stimulus to the beads. In some cases, the stimulus may be a photo-stimulus, e.g., through cleavage of a photo-labile linkage that releases the nucleic acid molecules. In other cases, a thermal stimulus may be used, where elevation of the temperature of the beads environment will result in cleavage of a linkage or other release of the nucleic acid molecules from the beads. In still other cases, a chemical stimulus can be used that cleaves a linkage of the nucleic acid molecules to the beads, or otherwise results in release of the nucleic acid molecules from the beads. In one case, such compositions include the polyacrylamide matrices described above for encapsulation of biological particles and may be degraded for release of the attached nucleic acid molecules through exposure to a reducing agent, such as DTT.

In some aspects, provided are systems and methods for controlled partitioning. Droplet size may be controlled by adjusting certain geometric features in channel architecture (e.g., microfluidics channel architecture). For example, an expansion angle, width, and/or length of a channel may be adjusted to control droplet size. For example, regarding FIG. 8, a discrete droplet generated may include a bead (e.g., as in occupied droplets 816). Alternatively, a discrete droplet generated may include more than one bead. Alternatively, a discrete droplet generated may not include any beads (e.g., as in unoccupied droplet 818). In some instances, a discrete droplet generated may contain one or more biological particles, as described elsewhere herein. In some instances, a discrete droplet generated may comprise one or more reagents, as described elsewhere herein.

In some instances, the aqueous fluid 808 can have a substantially uniform concentration or frequency of beads 812. The beads 812 can be introduced into the channel segment 802 from a separate channel (not shown in FIG. 8). The frequency of beads 812 in the channel segment 802 may be controlled by controlling the frequency in which the beads 812 are introduced into the channel segment 802 and/or the relative flow rates of the fluids in the channel segment 802 and the separate channel. In some instances, the beads can be introduced into the channel segment 802 from a plurality of different channels, and the frequency controlled accordingly.

In some instances, the aqueous fluid 808 in the channel segment 802 can comprise biological particles (e.g., described with reference to FIGS. 5 and 8). In some instances, the aqueous fluid 808 can have a substantially uniform concentration or frequency of biological particles. As with the beads, the biological particles can be introduced into the channel segment 802 from a separate channel. The frequency or concentration of the biological particles in the aqueous fluid 808 in the channel segment 802 may be controlled by controlling the frequency in which the biological particles are introduced into the channel segment 802 and/or the relative flow rates of the fluids in the channel segment 802 and the separate channel. In some instances, the biological particles can be introduced into the channel segment 802 from a plurality of different channels, and the frequency controlled accordingly. In some instances, a first separate channel can introduce beads and a second separate channel can introduce biological particles into the channel segment 802. The first separate channel introducing the beads may be upstream or downstream of the second separate channel introducing the biological particles.

The second fluid 810 can comprise an oil, such as a fluorinated oil, that includes a fluorosurfactant for stabilizing the resulting droplets, for example, inhibiting subsequent coalescence of the resulting droplets.

In some instances, the second fluid 810 may not be subjected to and/or directed to any flow in or out of the reservoir 804. For example, the second fluid 810 may be substantially stationary in the reservoir 804. In some instances, the second fluid 810 may be subjected to flow within the reservoir 804, but not in or out of the reservoir 804, such as via application of pressure to the reservoir 804 and/or as affected by the incoming flow of the aqueous fluid 808 at the junction 805. Alternatively, the second fluid 810 may be subjected and/or directed to flow in or out of the reservoir 804. For example, the reservoir 804 can be a channel directing the second fluid 810 from upstream to downstream, transporting the generated droplets.

The channel structure 800 at or near the junction 806 may have certain geometric features that at least partly determine the sizes of the droplets formed by the channel structure 800. The channel segment 802 can have a height, h0 and width, w, at or near the junction 806. By way of example, the channel segment 802 can comprise a rectangular cross-section that leads to a reservoir 804 having a wider cross-section (such as in width or diameter). Alternatively, the cross-section of the channel segment 802 can be other shapes, such as a circular shape, trapezoidal shape, polygonal shape, or any other shapes. The top and bottom walls of the reservoir 804 at or near the junction 806 can be inclined at an expansion angle, $\alpha$. The expansion angle, $\alpha$, allows the tongue (portion of the aqueous fluid 808 leaving channel segment 802 at junction 806 and entering the reservoir 804 before droplet formation) to increase in depth and facilitate decrease in curvature of the intermediately formed droplet. Droplet size may decrease with increasing expansion angle. The resulting droplet radius, Rd, may be predicted by the following equation for the aforementioned geometric parameters of h0, w, and $\alpha$:

$$R_d \approx 0.44\left(1 + 2.2\sqrt{\tan\alpha}\,\frac{w}{h_0}\right)\frac{h_0}{\sqrt{\tan\alpha}}$$

By way of example, for a channel structure with w=21 μm, h=21 μm, and $\alpha$=3°, the predicted droplet size is 121 μm. In another example, for a channel structure with w=25 μm, h=25 μm, and $\alpha$=5°, the predicted droplet size is 123 μm. In another example, for a channel structure with w=28 μm, h=28 μm, and $\alpha$=7°, the predicted droplet size is 124 μm.

In some instances, the expansion angle, $\alpha$, may be between a range of from about 0.5° to about 4°, from about 0.1° to about 10°, or from about 0° to about 90°. For example, the expansion angle can be at least about 0.01°, 0.1°, 0.2°, 0.3°, 0.4°, 0.5°, 0.6°, 0.7°, 0.8°, 0.9°, 1°, 2°, 3°, 4°, 5°, 6°, 7°, 8°, 9°, 10°, 15°, 20°, 25°, 30°, 35°, 40°, 45°, 50°, 55°, 60°, 65°, 70°, 75°, 80°, 85°, or higher. In some instances, the expansion angle can be at most about 89°, 88°, 87°, 86°, 85°, 84°, 83°, 82°, 81°, 80°, 75°, 70°, 65°, 60°, 55°, 50°, 45°, 40°, 35°, 30°, 25°, 20°, 15°, 10°, 9° 8°, 7°, 6°, 5° 4°, 3°, 2°, 10, 0.1°, 0.01°, or less. In some instances, the width, w, can be between a range of from about 100 micrometers (μm) to about 500 μm. In some instances, the width, w, can be between a range of from about 10 μm to about 200 μm. Alternatively, the width can be less than about 10 μm. Alternatively, the width can be greater than about 500 μm. In some instances, the flow rate of the aqueous fluid 808 entering the junction 806 can be between about 0.04 microliters (μL)/minute (min) and about 40 μL/min. In some instances, the flow rate of the aqueous fluid 808 entering the junction 806 can be between about 0.01 microliters (μL)/minute (min) and about 100 μL/min. Alternatively, the flow rate of the aqueous fluid 808 entering the junction 806 can be less than about 0.01 μL/min. Alternatively, the flow rate of the aqueous fluid 808 entering the junction 806 can be greater than about 40 μL/min, such as 45 μL/min, 50 μL/min, 55 μL/min, 60 μL/min, 65 μL/min, 70 μL/min, 75 μL/min, 80 μL/min, 85 μL/min, 90 μL/min, 95 μL/min, 100 μL/min, 110 μL/min, 120 μL/min, 130 μL/min, 140 μL/min, 150 μL/min, or greater. At lower flow rates, such as flow rates of about less than or equal to 10 microliters/minute, the droplet radius may not be dependent on the flow rate of the aqueous fluid 808 entering the junction 806.

In some instances, at least about 50% of the droplets generated can have uniform size. In some instances, at least about 55%, 60%, 65%, 70%, 75%, 80%, 85%, 90%, 95%, 96%, 97%, 98%, 99%, or greater of the droplets generated can have uniform size. Alternatively, less than about 50% of the droplets generated can have uniform size.

The throughput of droplet generation can be increased by increasing the points of generation, such as increasing the number of junctions (e.g., junction 806) between aqueous fluid 808 channel segments (e.g., channel segment 802) and the reservoir 804. Alternatively, or in addition, the throughput of droplet generation can be increased by increasing the flow rate of the aqueous fluid 808 in the channel segment 802.

The channel networks, e.g., as described above or elsewhere herein, can be fluidly coupled to appropriate fluidic components. For example, the inlet channel segments are fluidly coupled to appropriate sources of the materials they are to deliver to a channel junction. These sources may include any of a variety of different fluidic components, from simple reservoirs defined in or connected to a body structure of a microfluidic device, to fluid conduits that deliver fluids from off-device sources, manifolds, fluid flow units (e.g., actuators, pumps, compressors) or the like. Likewise, the outlet channel segment (e.g., channel segment 802, reservoir 804, etc.) may be fluidly coupled to a receiving vessel or conduit for the partitioned cells or nuclei for subsequent processing. Again, this may be a reservoir defined in the body of a microfluidic device, or it may be a fluidic conduit for delivering the partitioned cells or nuclei to a subsequent process operation, instrument, or component.

The methods and systems described herein may be used to greatly increase the efficiency of single cell or nucleus applications and/or other applications receiving droplet-based input. For example, following the sorting of occupied cells and/or appropriately-sized cells, subsequent operations that can be performed can include generation of amplification products, purification (e.g., via solid phase reversible immobilization (SPRI)), further processing (e.g., shearing, ligation of functional sequences, and subsequent amplification (e.g., via PCR)). These operations may occur in bulk (e.g., outside the partition). In the case where a partition is a droplet in an emulsion, the emulsion can be broken, and the contents of the droplet pooled for additional operations. Additional reagents that may be co-partitioned along with the barcode bearing bead may include oligonucleotides to block ribosomal RNA (rRNA) and nucleases to digest genomic DNA from cells or nuclei. Alternatively, rRNA removal agents may be applied during additional processing operations. The configuration of the constructs generated by such a method can help minimize (or avoid) sequencing of the poly-T sequence during sequencing and/or sequence the 5' end of a polynucleotide sequence. The amplification products, for example, first amplification products and/or second amplification products, may be subject to sequencing for sequence analysis. In some cases, amplification may be performed using the Partial Hairpin Amplification for Sequencing (PHASE) method.

A variety of applications require the evaluation of the presence and quantification of different biological particle or organism types within a population of biological particles, including, for example, microbiome analysis and characterization, environmental testing, food safety testing, epidemiological analysis, e.g., in tracing contamination or the like.

Enzymes, Polymerases and Reverse Transcriptases

In some examples, various assays are performed on cells, nuclei, cell beads, and/or biomolecules from such cells, nuclei, or cell beads. Exemplary assays may include single-cell transcription profiling, single-cell sequence analysis, and the like. These and other assays may be carried out using available systems for partitioning (e.g., encapsulating) biological samples, gel beads, barcodes, and/or other compounds/materials in droplets, such as The Chromium System (10× Genomics, Pleasanton, CA, USA) or wells.

Example reagents used in these assays may include a variety of enzymes, including polymerases, such as DNA or RNA polymerases, for example. The enzymes used in these assays may be isolated enzymes and/or purified enzymes.

Example assay reagents may include reverse transcriptases (RTs). RT refers to an enzyme that can synthesize single-stranded DNA using an RNA template (e.g., first-strand synthesis). Generally, RT enzymes may also synthesize single-stranded DNA using a DNA template (e.g., second-strand synthesis).

In some examples, RT may have terminal transferase activity. RT enzymes may have template switching activity, which generally relies on ability of an RT having terminal transferase activity to add non-templated deoxynucleotides to the 3' end of a DNA strand synthesized in first-strand synthesis. In presence of a template-switching oligonucleotide that can hybridize to the non-templated sequence added to the 3' end of the first stand, a template-switching reverse transcriptase may "switch" from using the RNA template that serves as the template for first-strand synthesis, to using the template-switching oligonucleotide as template, to extend the length of the first-strand synthesis product.

In some embodiments, template switching can be used to increase the length of cDNA generated in an assay. In some embodiments, template switching can be used to append a predefined nucleic acid sequence to the cDNA. In an example of template switching, cDNA can be generated from reverse transcription of a template, e.g., cellular mRNA, where a reverse transcriptase with terminal transferase activity can add additional nucleotides, e.g., polyC, to the cDNA in a template independent manner.

In some examples, RT may have RNase H activity.

Reverse transcriptases may come from a variety of different systems. In some examples, reverse transcriptases may be from, may be derived from, or may be variants of Avian myeloblastosis virus (AMV) RT or Moloney Murine leukemia virus (MMLV) RT.

Additional assay reagents that may be used with RT enzymes may include RNA or DNA templates, primers for first-stand or second-strand DNA synthesis, and template switching oligonucleotides. Reverse transcriptase enzymes generally require including deoxyribonucleotides (dNTPs). Reverse transcriptase enzymes may require magnesium ions (Mg2+) and/or manganese ions (Mn2+) for activity.

Additional example assay reagents that may be used to perform assays using cells, nuclei, cell beads and/or biomolecules derived therefrom, include any assay reagents that can be used to perform one or more chemical or biochemical operations encapsulated in a droplet. Accordingly, assay reagents useful in the assay method include any reagents useful in performing a reaction such as nucleic acid modification (e.g., ligation, digestion, methylation, random mutagenesis, bisulfite conversion, uracil hydrolysis, nucleic acid repair, capping, or decapping), nucleic acid amplification (e.g., isothermal amplification or PCR), nucleic acid insertion or cleavage (e.g., via CRISPR/Cas9-mediated or transposon-mediated insertion or cleavage), and/or reverse transcription. Additionally, useful assay reagents can include those that allow the preparation of a target sequence or sequencing reads that are specific to the macromolecular constituents of interest at a higher rate than to non-target sequence specific reads.

Compositions

Also provided herein is a composition (e.g., processed sample) comprising a cell or cell nucleus and an extracellular nucleic acid molecule fragment. In some examples, the nucleic acid molecule fragment may be smaller than about: 50 base pairs (bp), 40 bp, 30 bp, 20 bp, 10 bp, 5 bp, 3 bp, 2 bp, or smaller in size. The composition may be free or substantially free of an extracellular nucleic acid molecule larger than about: 60 base pairs (bp), 70 bp, 80 bp, 90 bp, 100 bp, 200 bp, 300 bp, 400 bp, 500 bp, 600 bp, 700 bp, 800 bp, 900 bp, 1 kbp, or larger in size. In some cases, the composition (e.g., processed sample) may be free or substantially free of an extracellular nucleic acid molecule with a size of at least about: 0.01 inch, 0.05 inch, 0.1 inch, 0.2 inch, 0.3 inch, 0.4 inch, 0.5 inch, 0.6 inch, 0.7 inch, 0.8 inch, 0.9 inch, 1 inch, 1.1 inch, 1.2 inch, 1.3 inch, 1.4 inch, 1.5 inch, 1.6 inch, 1.7 inch, 1.8 inch, 1.9 inch, 2 inch, 2.1 inch, 2.2 inch, 2.3 inch, 2.4 inch, 2.5 inch, or more. In some instances, the composition (e.g., processed sample) may be substantially free of an extracellular nucleic acid molecule with a size of at least about: 1 nanometer(s) (nm), 2 nm, 3 nm, 4 nm, 5 nm, 6 nm, 7 nm, 8 nm, 9 nm, 10 nm, 20 nm, 30 nm, 40 nm, 50 nm, 60 nm, 70 nm, 80 nm, 90 nm, 100 nm, 200 nm, 300 nm, 400 nm, 500 nm, 600 nm, 700 nm, 800 nm, 900 nm, 1 micrometer(s) ($\mu$m), 2 $\mu$m, 3 $\mu$m, 4 $\mu$m, 5 $\mu$m, 6 $\mu$m, 7 $\mu$m, 8 $\mu$m, 9 $\mu$m, 10 $\mu$m, 20 $\mu$m, 30 $\mu$m, 40 $\mu$m, 50 $\mu$m, 60 $\mu$m, 70 $\mu$m, 80 $\mu$m, 90 $\mu$m, 100 $\mu$m, 200 $\mu$m, 300 $\mu$m, 400 $\mu$m, 500 $\mu$m, 600 $\mu$m, 700 $\mu$m, 800 $\mu$m, 900 $\mu$m, 1 millimeter(s) mm, 2 mm, 3 mm, 4 mm, 5 mm, 6 mm, 7 mm, 8 mm, 9 mm, 10 mm, 20 mm, 30 mm, 40 mm, 50 mm, 60 mm, 70 mm, 80 mm, 90 mm, 100 mm, 200 mm, 300 nm, 400 mm, 500 mm, 600 mm, 700 mm, 800 mm, 900 mm, 1 centimeter(s) (cm), 2 cm, 3 cm, 4 cm, 5 cm, 6 cm, 7 cm, 8 cm, 9 cm, 10 cm, or larger.

In some instances, a composition (e.g., processed sample) herein may be a composition comprising an extracellular molecule, such as an extracellular nucleic acid molecule (e.g., DNA and/or RNA), a nucleic acid molecule fragment, and/or both. The composition (e.g., processed sample) may comprise a support with and enzyme attached thereto (e.g., support 108 shown in FIG. 1). In some examples, the support comprising the enzyme may be further separated from the processed sample and/or compositions. Examples of compositions (e.g., sample 1610, 1620, 1710, and 1720) are provided in FIGS. 16 and 17.

In some instances, a composition (e.g., a processed sample) herein may be substantially free of the supports. For example, the method may further comprise separating the support from the processed sample. Separation may comprise any method or technique. In an example, the support may comprise magnetic properties. The support may be a magnetic support. For example, the support may be a magnetic bead, such as a solid magnetic microsphere with any size, such as the diameters provided elsewhere herein. In another example, the support may be a gel bead. The gel bead may be a magnetic gel bead. For example, the gel bead may comprise magnetic properties. The bead may comprise magnetic particles, such as magnetic nanoparticles therein.

Figure 16:
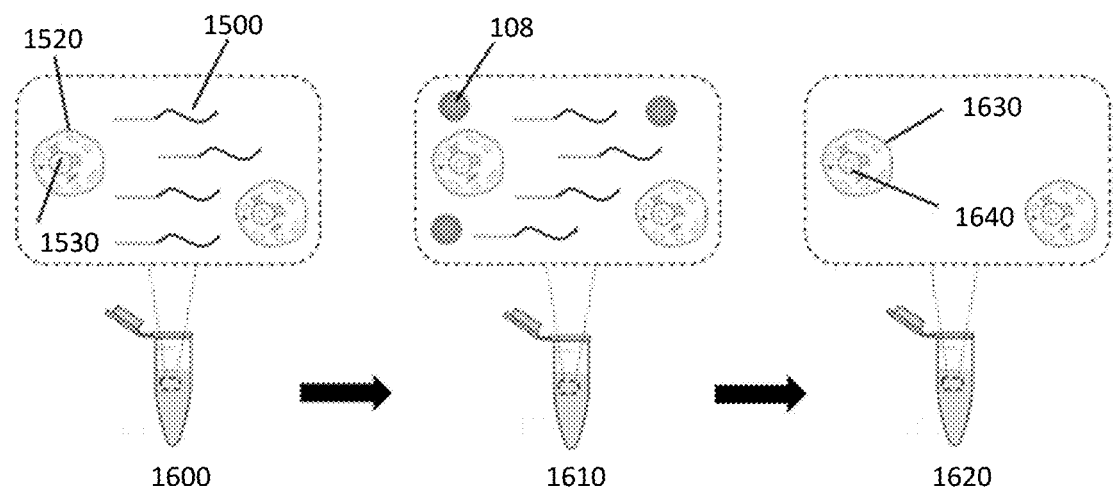
FIG. 16 shows an example workflow for processing a sample according to the methods of the present disclosure.
Figure 17:
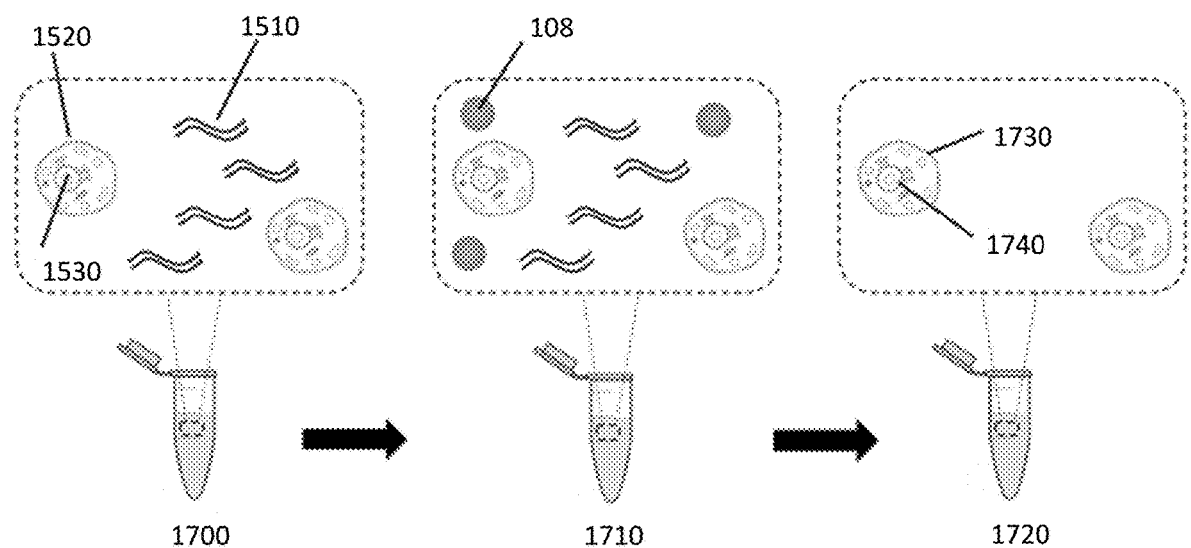
FIG. 17 shows an example workflow for processing a sample according to the methods of the present disclosure.

A magnetic or electromagnetic force may be applied to the sample to separate the support from the sample. The supports comprising the enzymes may be separated and removed from the sample (e.g., sample 1610 and 1710). An example of a sample or composition (e.g., sample 1620 and 1720) that may be substantially free of supports is illustrated in FIGS. 16 and 17.

In some instances, a composition (e.g., processed sample) herein may be provided in a partition or a plurality of partitions. The partition may be a droplet or a microwell. The composition may further comprise (i) a first phase and (ii) a second phase immiscible with the first phase. The first phase may comprise the composition (e.g., a processed sample such as sample 1620 or 1720 shown in FIG. 16 and FIG. 17). The first phase may be an aqueous phase and/or the second phase may be an oil phase. The composition may be a suspension. For example, the method may comprise partitioning the processed sample in a partition. In some examples, the partition may be a microwell. The partition may be a droplet. The droplet may be generated using a microfluidic device (e.g., the microfluidic devices shown in FIGS. 5-10 or other devices). Alternatively, a suspension comprising a plurality of aqueous droplets in an immiscible oil may be generated without using a microfluidic device. In some examples, the droplet may be generated at least in part by (i) providing a mixture comprising (1) a first phase comprising the processed sample and (2) a second phase immiscible with the first phase, and (ii) subjecting the mixture to agitation. The first phase may be an aqueous phase and/or the second phase may be an oil phase. In some examples, the agitation may comprise vortexing, for example by placing a container comprising the sample or composition on a device, platform or system such as a vortexer and generating turbulence and/or agitation in the sample, thereby generating an emulsion or a droplets (e.g., aqueous droplets in an immiscible oil).

In some examples, disclosed here are compositions of a catalyst attached to a support. In some examples, the composition may be a nuclease associated with a bead. In some examples, the composition may be one or more DNases attached to a bead.

In some examples, disclosed here are compositions of a biological particle and a catalyst attached to or associated with a support. In some examples, the composition may be aggregated or clumped cells and one or more DNases attached to a bead.

In some examples, disclosed here are compositions of processed biological particles encapsulated in a discrete droplet. In some examples, the composition may be a single cell obtained by a method disclosed here, that is encapsulated in a discrete droplet.

Kits

Also provided herein are kits.

In some examples, the kit may comprise a support which comprises an enzyme (e.g., attached thereto), and the enzyme may be configured to degrade an extracellular molecule such as an extracellular nucleic acid in the sample. The support and the enzyme may be according to the supports and enzymes provided elsewhere herein. The kit may further comprise instructions (e.g., printed instructions) for bringing the sample comprising a cell or a cell nucleus in contact with the support, to degrade an extracellular nucleic acid in the sample to yield a processed sample, and/or for separating and/or removing the support and enzyme from the biological particle and/or processed biological particle, for example according to the methods provided elsewhere herein. The kit may further comprise additional reagents, consumables, biological particles, enzymes, buffers, tools, equipment, devices, such as microfluidic devices and/or other chemicals, instructions (e.g., printed instructions), and/or systems for performing the methods provided herein, thereby yielding a composition (e.g., a processed sample) provided herein. The kit may contain a device or component configured to remove the support and catalyst (e.g., enzyme) from the system.

In some instances, enzymes provided in a kit herein may be immobilized on a surface of the support or may be configured to be attached to surface of the support. The attachment may be according to an attachment described elsewhere herein. In an example, the kit may comprise the enzymes and the supports and instructions (e.g., printed instructions) for immobilizing the enzyme on the surface of the support. The enzyme may be immobilized on a surface of the support by an affinity-tag, entrapment, linkage, cross-linkage, covalent bond, or any combination thereof. Alternatively, the kit may comprise the support with the enzyme attached thereto. The enzyme may comprise a surface moiety or linker configured to bind the enzyme.

In some instances, a kit herein may comprise a support that may be configured to be impenetrable to the cell and the cell nucleus, such as the supports provided elsewhere herein. The support may be configured to be inert to cellular metabolism and/or intracellular activities. For example, in case the support is brought into contact with a sample comprising a cell and/or cell nucleus, the viability of the cells of the sample may be maintained. The kit may comprise a support that is configured to maintain the viability of the cell and does not cause any harm to a cell or a cell nucleus in the sample, such as the supports provided elsewhere herein. The support provided in the kit may be configured to maintain the integrity or structure of the membrane of the cell. The support may be separable from the cell and the cell nucleus. The support may be insoluble in the sample. The size of the support may be according to the size of the support provided elsewhere herein. The digestion method may be according to the methods provided elsewhere herein.

In some instances, a kit herein may comprise a magnetic support which may be configured to be separated from the sample using a magnetic or electromagnetic force. The kit may comprise a support such as a bead, resin, tube wall, pipette tip, column surface, micropillar, a particle, a nanoparticle, a protein, a peptide, a molecule, a large molecule, a planar surface, or any combination thereof. The kit may comprise a support such as a bead. The bead may be a solid bead or a gel bead. The bead may be a magnetic bead. The bead may be a gel bead comprising magnetic particles. The bead may be a solid magnetic microsphere. In some examples, the support may not be magnetic. The support may be configured to be separated from the sample according to the methods provided elsewhere herein.

In some instances, a kit herein may comprise an enzyme. The kit may comprise a support comprising an enzyme. The enzyme may comprise a hydrolase, a nuclease, a deoxyribonuclease, an exonuclease, a restriction enzyme, a protease, or any combination thereof. In some examples, the enzyme may comprise at least one of deoxyribonuclease and exonuclease. The enzyme may be coupled to the support during or subsequent to degradation of the extracellular molecule, such as the extracellular nucleic acid molecule. Alternatively, the enzyme may get detached from the support during or subsequent to the digestion. The enzyme and the support may be according to the enzymes and supports provided elsewhere herein.

In some instances, a kit herein may be used to digest an extracellular molecule in a sample. The extracellular molecule may be according to an extracellular molecule provided elsewhere herein. For example, the extracellular molecule may be an extracellular nucleic acid molecule, such as ribonucleic acid (RNA) or deoxyribonucleic acid (DNA). Examples of the extracellular nucleic acid molecules may comprise messenger RNA (mRNA), chromosome, and genomic DNA (gDNA), or other examples provided elsewhere herein.

In some instances, a kit herein may further comprise one or more microfluidic devices. The microfluidic device(s) may be used to separate the support from the sample. The microfluidic device(s) may be used to compartmentalize the sample into a plurality of partitions such as droplets or wells (e.g., devices shown in FIGS. 5-10). The microfluidic devices may perform a combination of the techniques listed elsewhere herein.

Well-Based Analysis

As described herein, one or more processes can be performed in a partition, which can be a well. The well can be a well of a plurality of wells of a substrate, such as a microwell of a microwell array or plate, or the well can be a microwell or microchamber of a device (e.g., microfluidic device) comprising a substrate. The well can be a well of a well array or plate, or the well can be a well or chamber of a device (e.g., fluidic device). Accordingly, the wells or microwells can assume an "open" configuration, in which the wells or microwells are exposed to the environment (e.g., contain an open surface) and are accessible on one planar face of the substrate, or the wells or microwells can assume a "closed" or "sealed" configuration, in which the microwells are not accessible on a planar face of the substrate. In some instances, the wells or microwells can be configured to toggle between "open" and "closed" configurations. For instance, an "open" microwell or set of microwells can be "closed" or "sealed" using a membrane (e.g., semi-permeable membrane), an oil (e.g., fluorinated oil to cover an aqueous solution), or a lid, as described elsewhere herein. The wells or microwells can be initially provided in a "closed" or "sealed" configuration, wherein they are not accessible on a planar surface of the substrate without an external force. For instance, the "closed" or "sealed" configuration can include a substrate such as a sealing film or foil that is puncturable or pierceable by pipette tip(s). Suitable materials for the substrate include, without limitation, polyester, polypropylene, polyethylene, vinyl, and aluminum foil.

In some embodiments, the well can have a volume of less than 1 milliliter (mL). For example, the well can be configured to hold a volume of at most 1000 microliters (μL), at most 100 μL, at most 10 μL, at most 1 μL, at most 100 nanoliters (nL), at most 10 nL, at most 1 nL, at most 100 picoliters (pL), at most 10 (pL), or less. The well can be configured to hold a volume of about 1000 μL, about 100 μL, about 10 μL, about 1 μL, about 100 nL, about 10 nL, about 1 nL, about 100 μL, about 10 μL, etc. The well can be configured to hold a volume of at least 10 pL, at least 100 pL, at least 1 nL, at least 10 nL, at least 100 nL, at least 1 μL, at least 10 μL, at least 100 μL, at least 1000 μL, or more. The well can be configured to hold a volume in a range of volumes listed herein, for example, from about 5 nL to about 20 nL, from about 1 nL to about 100 nL, from about 500 μL to about 100 μL, etc. The well can be of a plurality of wells that have varying volumes and can be configured to hold a volume appropriate to accommodate any of the partition volumes described herein.

In some instances, a microwell array or plate includes a single variety of microwells. In some instances, a microwell array or plate includes a variety of microwells. For instance, the microwell array or plate can include one or more types of microwells within a single microwell array or plate. The types of microwells can have different dimensions (e.g., length, width, diameter, depth, cross-sectional area, etc.), shapes (e.g., circular, triangular, square, rectangular, pentagonal, hexagonal, heptagonal, octagonal, nonagonal, decagonal, etc.), aspect ratios, or other physical characteristics. The microwell array or plate can include any number of different types of microwells. For example, the microwell array or plate can include 1, 2, 3, 4, 5, 6, 7, 8, 9, 10, 20, 30, 40, 50, 60, 70, 80, 90, 100, 200, 300, 400, 500, 600, 700, 800, 900, 1000 or more different types of microwells. A well can have any dimension (e.g., length, width, diameter, depth, cross-sectional area, volume, etc.), shape (e.g., circular, triangular, square, rectangular, pentagonal, hexagonal, heptagonal, octagonal, nonagonal, decagonal, other polygonal, etc.), aspect ratios, or other physical characteristics described herein with respect to any well.

In certain instances, the microwell array or plate includes different types of microwells that are located adjacent to one another within the array or plate. For example, a microwell with one set of dimensions can be located adjacent to and in contact with another microwell with a different set of dimensions. Similarly, microwells of different geometries can be placed adjacent to or in contact with one another. The adjacent microwells can be configured to hold different articles; for example, one microwell can be used to contain a biological particle, such as a cell, a nucleus, or other sample (e.g., cellular components, nucleic acid molecules, etc.) while the adjacent microwell can be used to contain a support (e.g., a bead such as a gel bead), droplet, or other reagent. In some cases, the adjacent microwells can be configured to merge the contents held within, e.g., upon application of a stimulus, or spontaneously, upon contact of the articles in each microwell.

As is described elsewhere herein, a plurality of partitions can be used in the systems, compositions, and methods described herein. For example, any suitable number of partitions (e.g., wells or droplets) can be generated or otherwise provided. For example, in the case when wells are used, at least about 1,000 wells, at least about 5,000 wells, at least about 10,000 wells, at least about 50,000 wells, at least about 100,000 wells, at least about 500,000 wells, at least about 1,000,000 wells, at least about 5,000,000 wells at least about 10,000,000 wells, at least about 50,000,000 wells, at least about 100,000,000 wells, at least about 500,000,000 wells, at least about 1,000,000,000 wells, or more wells can be generated or otherwise provided. Moreover, the plurality of wells can include both unoccupied wells (e.g., empty wells) and occupied wells.

A well can include any of the reagents described herein, or combinations thereof. These reagents can include, for example, barcode molecules, enzymes, adapters, and combinations thereof. The reagents can be physically separated from a biological particle (for example, a cell, a nucleus, or cellular components, e.g., proteins, nucleic acid molecules, etc.) that is placed in the well. This physical separation can be accomplished by containing the reagents within, or coupling to, a support (e.g., a bead such as a gel bead) that is placed within a well. The physical separation can also be accomplished by dispensing the reagents in the well and overlaying the reagents with a layer that is, for example, dissolvable, meltable, or permeable prior to introducing the polynucleotide sample into the well. This layer can be, for example, an oil, wax, membrane (e.g., semi-permeable membrane), or the like. The well can be sealed at any point, for example, after addition of the support or bead, after addition of the reagents, or after addition of either of these components. The sealing of the well can be useful for a variety of purposes, including preventing escape of beads or loaded reagents from the well, permitting select delivery of certain reagents (e.g., via the use of a semi-permeable membrane), for storage of the well prior to or following further processing, etc.

Once sealed, the well may be subjected to conditions for further processing of a cell (or cells) in the well. For instance, reagents in the well may allow further processing of the cell, e.g., cell lysis, as further described herein. Alternatively, the well (or wells such as those of a well-based array) comprising the cell (or cells) may be subjected to freeze-thaw cycling to process the cell (or cells), e.g., cell lysis. The well containing the cell may be subjected to freezing temperatures (e.g., 0° C., below 0° C., −5° C., −10° C., −15° C., −20° C., −25° C., −30° C., −35° C., −40° C., −45° C., −50° C., −55° C., −60° C., −65° C., −70° C., −80° C., or −85° C.). Freezing may be performed in a suitable manner, e.g., sub-zero freezer or a dry ice/ethanol bath. Following an initial freezing, the well (or wells) comprising the cell (or cells) may be subjected to freeze-thaw cycles to lyse the cell (or cells). In one embodiment, the initially frozen well (or wells) are thawed to a temperature above freezing (e.g., 4° C. or above, 8° C. or above, 12° C. or above, 16° C. or above, 20° C. or above, room temperature, or 25° C. or above). In another embodiment, the freezing is performed for less than 10 minutes (e.g., 5 minutes or 7 minutes) followed by thawing at room temperature for less than 10 minutes (e.g., 5 minutes or 7 minutes). This freeze-thaw cycle may be repeated a number of times, e.g., 2, 3, 4 or more times, to obtain lysis of the cell (or cells) in the well (or wells). In one embodiment, the freezing, thawing and/or freeze/thaw cycling is performed in the absence of a lysis buffer.

A well can include free reagents and/or reagents encapsulated in, or otherwise coupled to or associated with, supports (e.g., beads), or droplets. In some embodiments, any of the reagents described in this disclosure can be encapsulated in, or otherwise coupled to, a support (e.g., a bead) or a droplet, with any chemicals, particles, and elements suitable for sample processing reactions involving biomolecules, such as, but not limited to, nucleic acid molecules and proteins. For example, a bead or droplet used in a sample preparation reaction for DNA sequencing can include one or more of the following reagents: enzymes, restriction enzymes (e.g., multiple cutters), ligase, polymerase, fluorophores, oligonucleotide barcodes, adapters, buffers, nucleotides (e.g., dNTPs, ddNTPs) and the like.

Additional examples of reagents include, but are not limited to: buffers, acidic solution, basic solution, temperature-sensitive enzymes, pH-sensitive enzymes, light-sensitive enzymes, metals, metal ions, magnesium chloride, sodium chloride, manganese, aqueous buffer, mild buffer, ionic buffer, inhibitor, enzyme, protein, polynucleotide, antibodies, saccharides, lipid, oil, salt, ion, detergents, ionic detergents, non-ionic detergents, oligonucleotides, nucleotides, deoxyribonucleotide triphosphates (dNTPs), dideoxyribonucleotide triphosphates (ddNTPs), DNA, RNA, peptide polynucleotides, complementary DNA (cDNA), double stranded DNA (dsDNA), single stranded DNA (ssDNA), plasmid DNA, cosmid DNA, chromosomal DNA, genomic DNA, viral DNA, bacterial DNA, mtDNA (mitochondrial DNA), mRNA, rRNA, tRNA, nRNA, siRNA, snRNA, snoRNA, scaRNA, microRNA, dsRNA, ribozyme, riboswitch and viral RNA, polymerase, ligase, restriction enzymes, proteases, nucleases, protease inhibitors, nuclease inhibitors, chelating agents, reducing agents, oxidizing agents, fluorophores, probes, chromophores, dyes, organics, emulsifiers, surfactants, stabilizers, polymers, water, small molecules, pharmaceuticals, radioactive molecules, preservatives, antibiotics, aptamers, and pharmaceutical drug compounds. As described herein, one or more reagents in the well can be used to perform one or more reactions, including but not limited to: biological particle (e.g., a cell or a nucleus) processing such as lysis, fixation, permeabilization, nucleic acid reactions, e.g., nucleic acid extension reactions, amplification, reverse transcription, reactions, etc.

The wells disclosed herein can be provided as a part of a kit. For example, a kit can include instructions for use, a microwell array or device, and reagents (e.g., beads). The kit can include any useful reagents for performing the processes described herein, e.g., nucleic acid reactions, barcoding of nucleic acid molecules, sample processing (e.g., for biological particle lysis, fixation, and/or permeabilization).

In some cases, a well includes a support (e.g., a bead) or droplet that includes a set of reagents that has a similar attribute, for example, a set of enzymes, a set of minerals, a set of oligonucleotides, a mixture of different barcode molecules, or a mixture of identical barcode molecules. In other cases, a support (e.g., a bead) or droplet includes a heterogeneous mixture of reagents. In some cases, the heterogeneous mixture of reagents can include all components necessary to perform a reaction. In some cases, such mixture can include all components necessary to perform a reaction, except for 1, 2, 3, 4, 5, or more components necessary to perform a reaction. In some cases, such additional components are contained within, or otherwise coupled to, a different support (e.g., a bead) or droplet, or within a solution within a partition (e.g., microwell) of the system.

Figure 19:
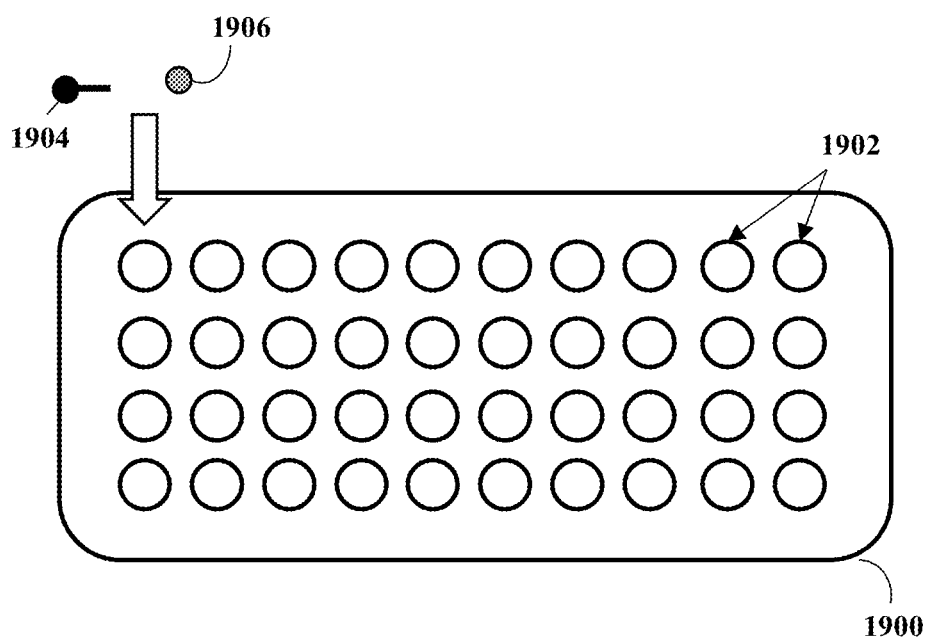
FIG. 19 shows an exemplary microwell array schematic.

FIG. 19 schematically illustrates an example of a microwell array. The array can be contained within a substrate 1900. The substrate 1900 comprises a plurality of wells 1902. The wells 1902 may be of any size or shape, and the spacing between the wells, the number of wells per substrate, as well as the density of the wells on the substrate 1900 can be modified, depending on the application. In one such example application, a sample molecule 1906, which may comprise a cell or nucleus or cellular components (e.g., nucleic acid molecules) is co-partitioned with a bead 1904, which may comprise a nucleic acid barcode molecule coupled thereto. The wells 1902 may be loaded using gravity or other loading technique (e.g., centrifugation, liquid handler, acoustic loading, optoelectronic, etc.). In some instances, at least one of the wells 1902 contains a single sample molecule 1906 (e.g., cell or nucleus) and a single bead 1904.

Reagents may be loaded into a well either sequentially or concurrently. In some cases, reagents are introduced to the device either before or after a particular operation. In some cases, reagents (which may be provided, in certain instances, in droplets or beads) are introduced sequentially such that different reactions or operations occur at different steps. The reagents (or droplets or beads) may also be loaded at operations interspersed with a reaction or operation step. For example, droplets or beads comprising reagents for fragmenting polynucleotides (e.g., restriction enzymes) and/or other enzymes (e.g., transposases, ligases, polymerases, etc.) may be loaded into the well or plurality of wells, followed by loading of droplets or beads comprising reagents for attaching nucleic acid barcode molecules to a sample nucleic acid molecule. Reagents may be provided concurrently or sequentially with a sample, such as a cell or nucleus or cellular components (e.g., organelles, proteins, nucleic acid molecules, carbohydrates, lipids, etc.). Accordingly, use of wells may be useful in performing multi-step operations or reactions.

As described elsewhere herein, the nucleic acid barcode molecules and other reagents may be contained within a bead or droplet. These beads or droplets may be loaded into a partition (e.g., a microwell) before, after, or concurrently with the loading of a cell or nucleus, such that each cell or nucleus is contacted with a different bead or droplet. This technique may be used to attach a unique nucleic acid barcode molecule to nucleic acid molecules obtained from each cell or nucleus. Alternatively, or in addition to, the sample nucleic acid molecules may be attached to a support. For instance, the partition (e.g., microwell) may comprise a bead which has coupled thereto a plurality of nucleic acid barcode molecules. The sample nucleic acid molecules, or derivatives thereof, may couple or attach to the nucleic acid barcode molecules on the support. The resulting barcoded nucleic acid molecules may then be removed from the partition, and in some instances, pooled and sequenced. In such cases, the nucleic acid barcode sequences may be used to trace the origin of the sample nucleic acid molecule. For example, polynucleotides with identical barcodes may be determined to originate from the same cell/nucleus or partition, while polynucleotides with different barcodes may be determined to originate from different cells/nuclei or partitions.

The samples or reagents may be loaded in the wells or microwells using a variety of approaches. The samples (e.g., a cell, a nucleus or cellular component) or reagents (as described herein) may be loaded into the well or microwell using an external force, e.g., gravitational force, electrical force, magnetic force, or using mechanisms to drive the sample or reagents into the well, e.g., via pressure-driven flow, centrifugation, optoelectronics, acoustic loading, electrokinetic pumping, vacuum, capillary flow, etc. In certain cases, a fluid handling system may be used to load the samples or reagents into the well. The loading of the samples or reagents may follow a Poissonian distribution or a non-Poissonian distribution, e.g., super Poisson or sub-Poisson. The geometry, spacing between wells, density, and size of the microwells may be modified to accommodate a useful sample or reagent distribution; for instance, the size and spacing of the microwells may be adjusted such that the sample or reagents may be distributed in a super-Poissonian fashion.

In one particular non-limiting example, the microwell array or plate comprises pairs of microwells, in which each pair of microwells is configured to hold a droplet (e.g., comprising a single cell or nucleus) and a single bead (such as those described herein, which may, in some instances, also be provided or encapsulated in a droplet). The droplet and the bead (or droplet containing the bead) may be loaded simultaneously or sequentially, and the droplet and the bead may be merged, e.g., upon contact of the droplet and the bead, or upon application of a stimulus (e.g., external force, agitation, heat, light, magnetic or electric force, etc.). In some cases, the loading of the droplet and the bead is super-Poissonian. In other examples of pairs of microwells, the wells are configured to hold two droplets comprising different reagents and/or samples, which are merged upon contact or upon application of a stimulus. In such instances, the droplet of one microwell of the pair can comprise reagents that may react with an agent in the droplet of the other microwell of the pair. For instance, one droplet can comprise reagents that are configured to release the nucleic acid barcode molecules of a bead contained in another droplet, located in the adjacent microwell. Upon merging of the droplets, the nucleic acid barcode molecules may be released from the bead into the partition (e.g., the microwell or microwell pair that are in contact), and further processing may be performed (e.g., barcoding, nucleic acid reactions, etc.). In cases where cells or nuclei are loaded in the microwells, one of the droplets may comprise reagents for further processing, e.g., lysis reagents for lysing the cell or nucleus, upon droplet merging.

A droplet may be partitioned into a well. The droplets may be selected or subjected to pre-processing prior to loading into a well. For instance, the droplets may comprise cells or nuclei and only certain droplets, such as those containing a single cell or nucleus (or at least one cell/nucleus), may be selected for use in loading of the wells. Such a pre-selection process may be useful in efficient loading of single cells or nuclei, such as to obtain a non-Poissonian distribution, or to pre-filter cells or nuclei for a selected characteristic prior to further partitioning in the wells. Additionally, the technique may be useful in obtaining or preventing cell/nucleus doublet or multiplet formation prior to or during loading of the microwell.

In some instances, the wells can comprise nucleic acid barcode molecules attached thereto. The nucleic acid barcode molecules may be attached to a surface of the well (e.g., a wall of the well). The nucleic acid barcode molecule (e.g., a partition barcode sequence) of one well may differ from the nucleic acid barcode molecule of another well, which can permit identification of the contents contained with a single partition or well. In some cases, the nucleic acid barcode molecule can comprise a spatial barcode sequence that can identify a spatial coordinate of a well, such as within the well array or well plate. In some cases, the nucleic acid barcode molecule can comprise a unique molecular identifier for individual molecule identification. In some instances, the nucleic acid barcode molecules may be configured to attach to or capture a nucleic acid molecule within a sample or cell or nucleus distributed in the well. For example, the nucleic acid barcode molecules may comprise a capture sequence that may be used to capture or hybridize to a nucleic acid molecule (e.g., RNA, DNA) within the sample. In some instances, the nucleic acid barcode molecules may be releasable from the microwell. For instance, the nucleic acid barcode molecules may comprise a chemical cross-linker which may be cleaved upon application of a stimulus (e.g., photo-, magnetic, chemical, biological, stimulus). The released nucleic acid barcode molecules, which may be hybridized or configured to hybridize to a sample nucleic acid molecule, may be collected and pooled for further processing, which can include nucleic acid processing (e.g., amplification, extension, reverse transcription, etc.) and/or characterization (e.g., sequencing). In such cases, the unique partition barcode sequences may be used to identify the cell/nucleus or partition from which a nucleic acid molecule originated.

Characterization of samples within a well may be performed. Such characterization can include, in non-limiting examples, imaging of the sample (e.g., cell/nucleus or cellular components) or derivatives thereof. Characterization techniques such as microscopy or imaging may be useful in measuring sample profiles in fixed spatial locations. For instance, when cells or nuclei are partitioned, optionally with beads, imaging of each microwell and the contents contained therein may provide useful information on cell/nucleus doublet formation (e.g., frequency, spatial locations, etc.), cell-bead pair efficiency, cell viability, cell size, cell morphology, expression level of a biomarker (e.g., a surface marker, a fluorescently labeled molecule therein, etc.), cell/nucleus or bead loading rate, number of cell-bead pairs, cell-cell interactions (when two or more cells/nuclei are co-partitioned). Alternatively, or in addition to, imaging may be used to characterize a quantity of amplification products in the well.

In operation, a well may be loaded with a sample and reagents, simultaneously or sequentially. When cells or nuclei are loaded, the well may be subjected to washing, e.g., to remove excess cells from the well, microwell array, or plate. Similarly, washing may be performed to remove excess beads or other reagents from the well, microwell array, or plate. In addition, the cells or nuclei may be lysed in the individual partitions to release the intracellular components or cellular analytes. Alternatively, the cells or nuclei may be fixed or permeabilized in the individual partitions. The intracellular components or cellular analytes may couple to a support, e.g., on a surface of the microwell, on a solid support (e.g., bead), or they may be collected for further downstream processing. For instance, after cell lysis, the intracellular components or cellular analytes may be transferred to individual droplets or other partitions for barcoding. Alternatively, or in addition to, the intracellular components or cellular analytes (e.g., nucleic acid molecules) may couple to a bead comprising a nucleic acid barcode molecule; subsequently, the bead may be collected and further processed, e.g., subjected to nucleic acid reaction such as reverse transcription, amplification, or extension, and the nucleic acid molecules thereon may be further characterized, e.g., via sequencing. Alternatively, or in addition to, the intracellular components or cellular analytes may be barcoded in the well (e.g., using a bead comprising nucleic acid barcode molecules that are releasable or on a surface of the microwell comprising nucleic acid barcode molecules). The barcoded nucleic acid molecules or analytes may be further processed in the well, or the barcoded nucleic acid molecules or analytes may be collected from the individual partitions and subjected to further processing outside the partition. Further processing can include nucleic acid processing (e.g., performing an amplification, extension) or characterization (e.g., fluorescence monitoring of amplified molecules, sequencing). At any convenient or useful step, the well (or microwell array or plate) may be sealed (e.g., using an oil, membrane, wax, etc.), which enables storage of the assay or selective introduction of additional reagents.

Figure 20:
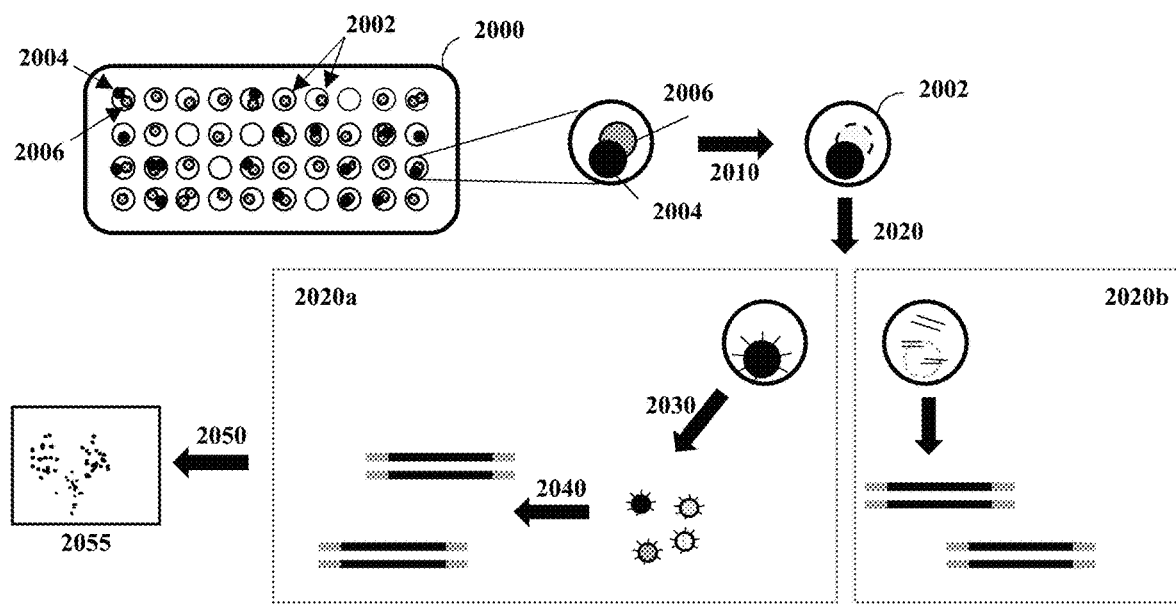
FIG. 20 shows an exemplary microwell array workflow for processing nucleic acid.

FIG. 20 schematically shows an example workflow for processing nucleic acid molecules within a sample. A substrate 2000 comprising a plurality of microwells 2002 may be provided. A sample 2006 which may comprise a cell or nucleus, cellular components or analytes (e.g., proteins and/or nucleic acid molecules) can be co-partitioned, in a plurality of microwells 2002, with a plurality of beads 2004 comprising nucleic acid barcode molecules. During process 2010, the sample 2006 may be processed within the partition. For instance, the cell or nucleus may be subjected to conditions sufficient to lyse the cells or nuclei and release the analytes contained therein. In process 2020, the bead 2004 may be further processed. By way of example, processes 2020*a* and 2020*b* schematically illustrate different workflows, depending on the properties of the bead 2004.

In 2020*a*, the bead comprises nucleic acid barcode molecules that are attached thereto, and sample nucleic acid molecules (e.g., RNA, DNA) may attach, e.g., via hybridization of ligation, to the nucleic acid barcode molecules. Such attachment may occur on the bead. In process 2030, the beads 2004 from multiple wells 2002 may be collected and pooled. Further processing may be performed in process 2040. For example, one or more nucleic acid reactions may be performed, such as reverse transcription, nucleic acid extension, amplification, ligation, transposition, etc. In some instances, adapter sequences are ligated to the nucleic acid molecules, or derivatives thereof, as described elsewhere herein. For instance, sequencing primer sequences may be appended to each end of the nucleic acid molecule. In process 2050, further characterization, such as sequencing may be performed to generate sequencing reads. The sequencing reads may yield information on individual cells or populations of cells or nuclei, which may be represented visually or graphically, e.g., in a plot 2055.

In 2020*b*, the bead comprises nucleic acid barcode molecules that are releasably attached thereto, as described below. The bead may degrade or otherwise release the nucleic acid barcode molecules into the well 2002; the nucleic acid barcode molecules may then be used to barcode nucleic acid molecules within the well 2002. Further processing may be performed either inside the partition or outside the partition. For example, one or more nucleic acid reactions may be performed, such as reverse transcription, nucleic acid extension, amplification, ligation, transposition, etc. In some instances, adapter sequences are ligated to the nucleic acid molecules, or derivatives thereof, as described elsewhere herein. For instance, sequencing primer sequences may be appended to each end of the nucleic acid molecule. In process 2050, further characterization, such as sequencing may be performed to generate sequencing reads. The sequencing reads may yield information on individual cells or populations of cells or nuclei, which may be represented visually or graphically, e.g., in a plot 2055.

Computer Systems

Figure 14:
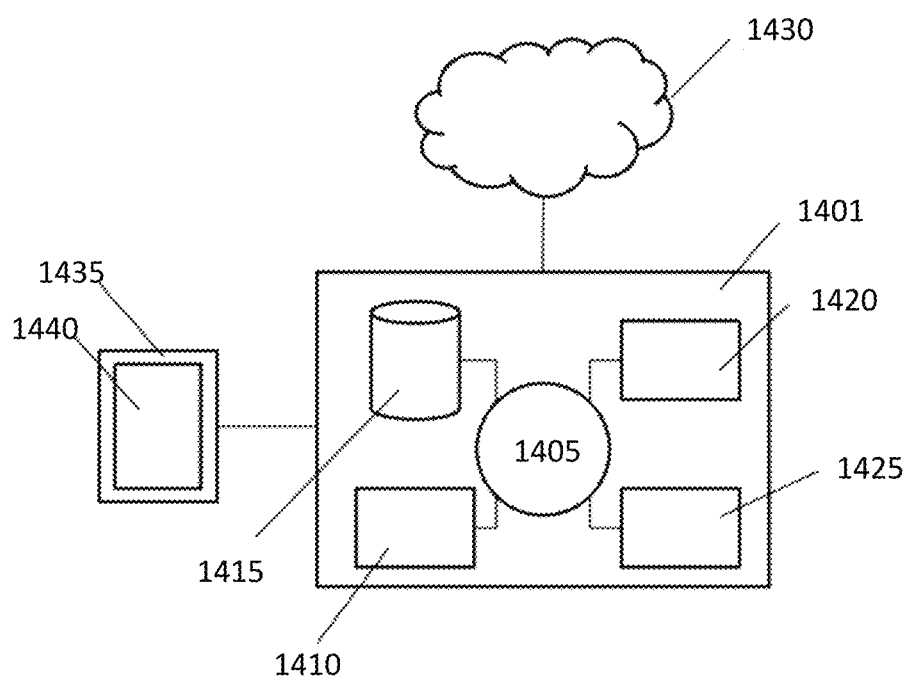
FIG. 14 shows a computer system that is programmed or otherwise configured to implement methods provided herein.

The present disclosure provides computer systems that are programmed to implement methods of the disclosure. FIG. 14 shows a computer system 1401 that is programmed or otherwise configured to perform the methods of the present disclosure, for example, control a microfluidics system to generate, sort, and/or manipulate droplets. For example, the computer system may control the pressure at the junctions of a microfluidic device, the flow of a fluid in a channel of the microfluidic device, the size of droplets, and more. The computer system may provide instructions to sort occupied droplets from unoccupied droplets, polymerize droplets, perform sequencing applications, and perform data analysis, such as measuring and storing sequencing data from the sample and/or cells or nuclei thereof. The computer system 1401 can regulate various aspects of the present disclosure, such as, for example, regulating fluid flow rate in one or more channels in a microfluidic structure, regulating polymerization application units, control the concentrations of reagents, cells, and supports, and/or chemicals in the sample or suspension. The computer system 1401 can be an electronic device of a user or a computer system that is remotely located with respect to the electronic device. The electronic device can be a mobile electronic device.

The computer system 1401 includes a central processing unit (CPU, also "processor" and "computer processor" herein) 1405, which can be a single core or multi core processor, or a plurality of processors for parallel processing. The computer system 1401 also includes memory or memory location 1410 (e.g., random-access memory, read-only memory, flash memory), electronic storage unit 1415 (e.g., hard disk), communication interface 1420 (e.g., network adapter) for communicating with one or more other systems, and peripheral devices 1425, such as cache, other memory, data storage and/or electronic display adapters. The memory 1410, storage unit 1415, interface 1420 and peripheral devices 1425 are in communication with the CPU 1405 through a communication bus (solid lines), such as a motherboard. The storage unit 1415 can be a data storage unit (or data repository) for storing data. The computer system 1401 can be operatively coupled to a computer network ("network") 1430 with the aid of the communication interface 1420. The network 1430 can be the Internet, an internet and/or extranet, or an intranet and/or extranet that is in communication with the Internet. The network 1430 in some cases is a telecommunication and/or data network. The network 1430 can include one or more computer servers, which can enable distributed computing, such as cloud computing. The network 1430, in some cases with the aid of the computer system 1401, can implement a peer-to-peer network, which may enable devices coupled to the computer system 1401 to behave as a client or a server.

The CPU 1405 can execute a sequence of machine-readable instructions, which can be embodied in a program or software. The instructions may be stored in a memory location, such as the memory 1410. The instructions can be directed to the CPU 1405, which can subsequently program or otherwise configure the CPU 1405 to implement methods of the present disclosure. Examples of operations performed by the CPU 1405 can include fetch, decode, execute, and writeback.

The CPU 1405 can be part of a circuit, such as an integrated circuit. One or more other components of the system 1401 can be included in the circuit. In some cases, the circuit is an application specific integrated circuit (ASIC).

The storage unit 1415 can store files, such as drivers, libraries and saved programs. The storage unit 1415 can store user data, e.g., user preferences and user programs. The computer system 1401 in some cases can include one or more additional data storage units that are external to the computer system 1401, such as located on a remote server that is in communication with the computer system 1401 through an intranet or the Internet.

The computer system 1401 can communicate with one or more remote computer systems through the network 1430. For instance, the computer system 1401 can communicate with a remote computer system of a user (e.g., operator). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 1401 via the network 1430.

Methods as described herein can be implemented by way of machine (e.g., computer processor) executable code stored on an electronic storage location of the computer system 1401, such as, for example, on the memory 1410 or electronic storage unit 1415. The machine executable or machine-readable code can be provided in the form of software. During use, the code can be executed by the processor 1405. In some cases, the code can be retrieved from the storage unit 1415 and stored on the memory 1410 for ready access by the processor 1405. In some situations, the electronic storage unit 1415 can be precluded, and machine-executable instructions are stored on memory 1410.

The code can be pre-compiled and configured for use with a machine having a processor adapted to execute the code or can be compiled during runtime. The code can be supplied in a programming language that can be selected to enable the code to execute in a pre-compiled or as-compiled fashion.

Aspects of the systems and methods provided herein, such as the computer system 1401, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 1401 can include or be in communication with an electronic display 1435 that comprises a user interface (UI) 1440 for providing, for example, the results of analyzing a sample provided herein in terms of a parameter. The sample may comprise a cell or cell nuclei.

Data analysis may comprise, for example, sequencing or other screening methods such as a single cell screening. Examples of UIs include, without limitation, a graphical user interface (GUI) and web-based user interface.

Methods and systems of the present disclosure can be implemented by way of one or more algorithms. An algorithm can be implemented by way of software upon execution by the central processing unit 1405. The algorithm can, for example, store and analyze sequence reads from nucleic acid molecules in the cells or cell nuclei of the sample. The algorithm may be further configured to identify data from noise and/or artifacts. For example, a sample may comprise cells and/or cell nucleus and the goal may be to analyze the cells or cell nuclei in terms of a parameter or characteristic, such as a marker. The method may comprise analyzing nucleic acid molecules in the cells/or cell nuclei of the sample. The sample may further comprise extracellular molecules, such as impurities, such as nucleic acid molecules, proteins, peptides, or other molecules that may interfere with the signals or data generated from the cell and/or cell nuclei. The algorithm may be configured to distinguish the data generated from the cells and/or cell nuclei of the sample from those generated from the extracellular molecules (e.g., extracellular nucleic acid molecules, ambient or background molecules or impurities). The algorithm may be configured to cluster the data in two or more subpopulations and use characteristic information such as parameters or markers to define each subpopulation.

Devices, systems, compositions and methods of the present disclosure may be used for various applications, such as, for example, processing a single analyte (e.g., RNA, DNA, or protein) or multiple analytes (e.g., DNA and RNA, DNA and protein, RNA and protein, or RNA, DNA and protein) from a single cell. For example, a biological particle (e.g., a cell or cell bead) is partitioned in a partition (e.g., droplet), and multiple analytes from the biological particle are processed for subsequent processing. The multiple analytes may be from the single cell. This may enable, for example, simultaneous proteomic, transcriptomic and genomic analysis of the cell.

EMBODIMENTS

Embodiments of the invention, which are not meant to be limiting, are described in the numbered paragraphs below.

1. A method for processing a sample that comprises a cell or cell nucleus, said method comprising bringing said sample in contact with a support to yield a processed sample, wherein said support comprises an enzyme attached thereto, and wherein said enzyme is configured to degrade an extracellular nucleic acid in said sample.

2. The method of paragraph 1, wherein said enzyme is immobilized on a surface of said support.

3. The method of paragraph 1, wherein said enzyme is immobilized on a surface of said support by an affinity-tag, entrapment, linkage, cross-linkage, covalent bond, or any combination thereof.

4. The method of paragraph 1, wherein said support comprises a surface moiety or linker configured to bind said enzyme.

5. The method of paragraph 1, wherein said support is configured to be impenetrable to said cell and said cell nucleus.

6. The method of paragraph 1, wherein said support is configured to be inert to cellular metabolism and intracellular activities.

7. The method of paragraph 1, wherein said support is configured to maintain the viability of said cell.

8. The method of paragraph 1, wherein said support is separable from said cell and said cell nucleus.

9. The method of paragraph 1, wherein said support is insoluble in said sample.

10. The method of paragraph 1, wherein said support is a sphere with a diameter of at least about 1 micrometer ($\mu$m) in size.

11. The method of paragraph 10, wherein said diameter is between about 1 micrometer ($\mu$m) to 20 micrometers ($\mu$m).

12. The method of paragraph 10, wherein said diameter is from about 5 micrometers ($\mu$m) to 10 micrometers ($\mu$m).

13. The method of paragraph 1, wherein said support is magnetic.

14. The method of paragraph 13, further comprising separating said support from said sample using a magnetic or electromagnetic force.

15. The method of paragraph 1, wherein said support is a bead, polymeric matrix, tube wall, pipette tip, column surface, micropillar, an array, a well, or any combination thereof.

16. The method of paragraph 1, wherein said support is a bead.

17. The method of paragraph 16, wherein said bead is a solid bead or a gel bead.

18. The method of paragraph 16, wherein said bead is a magnetic bead.

19. The method of paragraph 16, wherein said bead is a gel bead comprising magnetic particles.

20. The method of paragraph 16, wherein said bead is a solid magnetic microsphere.

21. The method of paragraph 1, wherein said enzyme comprises exonuclease I (ExoI).

22. The method of paragraph 1, wherein said enzyme is a hydrolase, a nuclease, a ribonuclease, an exonuclease, a restriction enzyme, a protease, or any combination thereof.

23. The method of paragraph 1, wherein said enzyme comprises at least one of ribonuclease and exonuclease.

24. The method of paragraph 1, wherein said extracellular nucleic acid comprises ribonucleic acid (RNA) or deoxyribonucleic acid (DNA).

25. The method of paragraph 1, wherein said extracellular nucleic acid comprises at least one of messenger RNA (mRNA), chromosome, and genomic DNA (gDNA).

26. The method of paragraph 1, wherein said enzyme is coupled to said support during or subsequent to degradation of said extracellular nucleic acid.

27. The method of paragraph 1, further comprising separating said support from said processed sample.

28. The method of any one of paragraphs 1 or 27, further comprising partitioning said processed sample in a partition.

29. The method of paragraph 28, wherein said partition is a microwell.

30. The method of paragraph 28, wherein said partition is a droplet.

31. The method of paragraph 30, wherein said droplet is generated using a microfluidic device.

32. The method of paragraph 30, wherein said droplet is generated at least in part by (i) providing a mixture comprising (1) a first phase comprising said processed sample and (2) a second phase immiscible with said first phase, and (ii) subjecting said mixture to agitation.

33. The method of paragraph 32, wherein said first phase is an aqueous phase or said second phase is an oil phase.

34. The method of paragraph 32, wherein said agitation comprises vortexing.

35. The method of paragraph 1, wherein said sample is a suspension.

36. A kit, comprising: (i) a support, wherein said support comprises an enzyme attached thereto, wherein said enzyme is configured to degrade an extracellular nucleic acid, and (ii) printed instructions for bringing a sample comprising a cell or a cell nucleus in contact with said support, to degrade an extracellular nucleic acid in said sample to yield a processed sample.

37. The kit of paragraph 36, wherein said enzyme is immobilized on a surface of said support.

38. The kit of paragraph 36, wherein said enzyme is immobilized on a surface of said support by an affinity-tag, entrapment, linkage, cross-linkage, covalent bond, or any combination thereof.

39. The kit of paragraph 36, wherein said support comprises a surface moiety or linker configured to bind said enzyme.

40. The kit of paragraph 36, wherein said support is configured to be impenetrable to said cell and said cell nucleus.

41. The kit of paragraph 36, wherein said support is configured to be inert to cellular metabolism and intracellular activities.

42. The kit of paragraph 36, wherein said support is configured to maintain the viability of said cell.

43. The kit of paragraph 36, wherein said support is configured to maintain the structure of a membrane of said cell.

44. The kit of paragraph 36, wherein said support is separable from said cell and said cell nucleus.

45. The kit of paragraph 36, wherein said support is insoluble in said sample.

46. The kit of paragraph 36, wherein said support is a sphere with a diameter of at least about 1 micrometer (μm) in size.

47. The kit of paragraph 46, wherein said diameter is between about 1 micrometer (μm) to 20 micrometers (μm).

48. The kit of paragraph 46, wherein said diameter is between about 5 micrometers (μm) to 10 micrometers (μm).

49. The kit of paragraph 36, wherein said support is a magnetic support configured to be separated from said sample using a magnetic or electromagnetic force.

50. The kit of paragraph 36, wherein said support comprises a bead, resin, tube wall, pipette tip, column surface, micropillar, or any combination thereof.

51. The kit of paragraph 36, wherein said support is a bead.

52. The kit of paragraph 51, wherein said bead is a solid bead or a gel bead.

53. The kit of paragraph 51, wherein said bead is a magnetic bead.

54. The kit of paragraph 51, wherein said bead is a gel bead comprising magnetic particles.

55. The kit of paragraph 51, wherein said bead is a solid magnetic microsphere.

56. The kit of paragraph 36, wherein said enzyme comprises a hydrolase, a nuclease, a ribonuclease, an exonuclease, a restriction enzyme, a protease, or any combination thereof.

57. The kit of paragraph 36, wherein said enzyme comprises at least one of ribonuclease and exonuclease.

58. The kit of paragraph 36, wherein said extracellular nucleic acid comprises ribonucleic acid (RNA) or deoxyribonucleic acid (DNA).

59. The kit of paragraph 36, wherein said extracellular nucleic acid comprises at least one of messenger RNA (mRNA), chromosome, and genomic DNA (gDNA).

60. The kit of paragraph 36, wherein said enzyme is coupled to said support during or subsequent to degradation of said extracellular nucleic acid.

61. A composition comprising a cell or cell nucleus and an extracellular nucleic acid molecule fragment, wherein said nucleic acid molecule fragment is smaller than 50 base pairs (bp) in size, and wherein said composition is substantially free of an extracellular nucleic acid molecule larger than about 60 base pairs (bp) in size.

62. The composition of paragraph 61, wherein said composition is provided in a partition.

63. The composition of paragraph 62, wherein said partition is a droplet or a microwell.

64. The composition of paragraph 61, further comprising (i) a first phase comprising said cell or cell nucleus and (ii) a second phase immiscible with said first phase.

65. The composition of paragraph 64, wherein said first phase is an aqueous phase or said second phase is an oil phase.

66. The composition of paragraph 61, wherein said composition is a suspension.

67. A composition comprising the processed sample of any one of paragraphs 1-35.

68. A method, comprising contacting a biological particle with a catalyst attached to a support to yield a processed biological particle.

69. The method of paragraph 68, wherein the biological particle comprises a single component.

70. The method of paragraphs 68 or 69, wherein the biological particle comprises multiple components.

71. The method of any one of paragraphs 68-70, wherein the biological particle comprises multiple components, including multiple cells and/or cell nuclei in an aggregate or clump.

72. The method of any one of paragraphs 68-71, wherein the biological particle comprises an aggregate or clump of suspension cells or anchorage-independent cells.

73. The method of any one of paragraphs 68-72, wherein the biological particle comprises an aggregate or clump of cells, including peripheral blood mononuclear cells (PBMCs) and/or nuclei from PBMCs.

74. The method of any one of paragraphs 68-73, wherein the biological particle comprises cellular debris and/or extracellular nucleic acids.

75. The method of any one of paragraphs 68-74, wherein the biological particle comprises extracellular deoxyribonucleic acid (DNA) and/or ribonucleic acid (RNA).

76. The method of any one of paragraphs 68-75, wherein the biological particle comprises extracellular deoxyribonucleic acid (DNA).

77. The method of any one of paragraphs 68-76, wherein the biological particle comprises a substance that promotes aggregation or clumping of components within the biological particle.

78. The method of any one of paragraphs 68-77, wherein the processed biological particle comprises single components.

79. The method of any one of paragraphs 68-78, wherein the processed biological particle comprises single components, including a single cell and/or cell nucleus.

80. The method of any one of paragraphs 68-79, wherein the processed biological particle comprises a single peripheral blood mononuclear cell (PBMC) and/or nucleus from a PBMC.

81. The method of any one of paragraphs 68-80, wherein the processed biological particle comprises no substance that promotes aggregation or clumping of single components in the biological particle, a reduced amount of a substance that promotes aggregation or clumping as compared to the biological particle from which the processed biological particle originated, or a degraded, inactivated or inhibited substance that promotes aggregation or clumping of multiple components.

82. The method of any one of paragraphs 68-81, wherein the processed biological particle comprises no extracellular nucleic acids, a reduced amount of extracellular nucleic acids as compared to the biological particle, or degraded extracellular nucleic acids.

83. The method of any one of paragraphs 68-82, wherein the processed biological particle comprises no extracellular DNA, a reduced amount of extracellular DNA as compared to the biological particle, or degraded DNA.

84. The method of any one of paragraphs 68-83, wherein the processed biological particle does not comprise the catalyst.

85. The method of any one of paragraphs 68-84, wherein the processed biological particle does not comprise the catalyst or the support.

86. The method of any one of paragraphs 68-85, wherein the catalyst includes a biological catalyst.

87. The method of any one of paragraphs 68-86, wherein the catalyst includes an enzyme.

88. The method of any one of paragraphs 68-87, wherein the catalyst includes a nuclease enzyme.

89. The method of any one of paragraphs 68-88, wherein the catalyst includes an endonuclease and/or an exonuclease.

90. The method of any one of paragraphs 68-89, wherein the catalyst includes a deoxyribonuclease (DNase) or ribonuclease (RNase).

91. The method of any one of paragraphs 68-90, wherein the catalyst includes a deoxyribonuclease (DNase).

92. The method of any one of paragraphs 68-91, wherein the catalyst processes the biological particle to a processed biological particle.

93. The method of any one of paragraphs 68-92, wherein the catalyst processes a biological particle having multiple components to one or more processed biological particles having single components.

94. The method of any one of paragraphs 68-93, wherein the catalyst processes the biological particle to degrade, inactivate or inhibit a substance that promotes aggregation or clumping of components within the biological particle.

95. The method of any one of paragraphs 68-94, wherein the catalyst processes the biological particle to degrade an extracellular nucleic acid in the biological particle.

96. The method of any one of paragraphs 68-95, wherein the catalyst processes the biological particle to degrade, inactivate or inhibit an extracellular DNA or RNA in the biological particle.

97. The method of any one of paragraphs 68-96, wherein the catalyst processes the biological particle to degrade, inactivate or inhibit an extracellular DNA in the biological particle.

98. The method of any one of paragraphs 68-97, wherein the catalyst degrades extracellular DNA in the biological particle.

99. The method of any one of paragraphs 68-98, wherein the catalyst is capable of processing a biological particle comprising viable cells without affecting or without significantly affecting viability of the cells.

100. The method of any one of paragraphs 68-99, wherein the catalyst is capable of being separated from the biological particle to yield the processed biological particle.

101. The method of any one of paragraphs 68-100, wherein the support includes a silica-based carrier, acrylic resin, synthetic polymer, active membrane and/or exchange resin.

102. The method of any one of paragraphs 68-101, wherein the support includes an organic or inorganic support.

103. The method of any one of paragraphs 68-102, wherein the support includes carboxymethyl-cellulose, starch, collagen, modified sepharose, an ion exchange resin, active charcoal, silica, clay, aluminum oxide, titanium, diatomaceous earth, hydroxyapatite, ceramic, celite, agarose, treated porous glass and/or a polymer.

104. The method of any one of paragraphs 68-103, wherein the support includes a nanoparticle, nanofiber, nanotube or nanocomposite.

105. The method of any one of paragraphs 68-104, wherein the support includes a bead, polymeric matrix, tube wall, pipette tip, column surface, micropillar, array, well, or combination thereof.

106. The method of any one of paragraphs 68-105, wherein the support includes a bead.

107. The method of any one of paragraphs 68-106, wherein the support includes a bead that is a solid bead or a gel bead.

108. The method of any one of paragraphs 68-107, wherein the support includes a bead that is magnetic.

109. The method of any one of paragraphs 68-108, wherein the support includes a gel bead comprising magnetic particles.

110. The method of any one of paragraphs 68-109, wherein the support includes a bead that is substantially spherical.

111. The method of any one of paragraphs 68-110, wherein the support includes a bead with a diameter of at least about 1 micrometer ($\mu$m) and/or between about 1-100, 1-20 or 5-10 $\mu$m in size.

112. The method of any one of paragraphs 68-111, wherein the support is configured to be impenetrable to the biological particle and/or to the processed biological particle.

113. The method of any one of paragraphs 68-112, wherein the support and the attached catalyst are configured such that the catalyst does not penetrate the biological particle and/or the processed biological particle.

114. The method of any one of paragraphs 68-113, wherein the support is configured to not bind the biological particle and/or the processed biological particle.

115. The method of any one of paragraphs 68-114, wherein the support is configured to be inert to metabolism and/or intracellular activities of cells.

116. The method of any one of paragraphs 68-115, wherein the support is configured to maintain viability, not decrease, or not substantially decrease cell viability.

117. The method of any one of paragraphs 68-116, wherein the support includes a surface moiety or linker configured to bind the catalyst.

118. The method of any one of paragraphs 68-117, wherein the support is capable of being separated from the biological particle to yield the processed biological particle.

119. The method of any one of paragraphs 68-118, wherein the catalyst is immobilized on the support.

120. The method of any one of paragraphs 68-119, wherein the catalyst is immobilized on a surface of the support.

121. The method of any one of paragraphs 68-120, wherein the catalyst is immobilized on a surface of the support by a physical and/or a chemical method.

122. The method of any one of paragraphs 68-121, wherein the catalyst is immobilized on a surface of the support by a physical method, including hydrogen bonds, hydrophobic interactions, van der Waals forces, affinity binding or ionic binding.

123. The method of any one of paragraphs 68-122, wherein the catalyst is immobilized on a surface of the support by a chemical method, including covalent bonds.

124. The method of any one of paragraphs 68-123, wherein the catalyst is immobilized on a surface of the support by a chemical method, including ether, thio-ether, amide and/or carbamate covalent bonds.

125. The method of any one of paragraphs 68-124, wherein the catalyst is immobilized on a surface of the support by an affinity-tag, entrapment, linkage, cross-linkage, covalent bond, or combination thereof.

126. The method of any one of paragraphs 68-125, wherein contacting comprises placing the catalyst and biological particle in proximity to one another such that the catalyst can process the biological particle.

127. The method of any one of paragraphs 68-126, wherein contacting comprises placing the catalyst in a location relative to the biological particle, and under conditions such that, the catalyst can yield a processed biological particle.

128. The method of any one of paragraphs 68-127, wherein contacting comprises physically touching the catalyst to the biological particle.

129. The method of any one of paragraphs 68-128, additionally comprising separating the support and attached catalyst from contact with the biological particle.

130. The method of any one of paragraphs 68-129, additionally comprising removing the support and attached catalyst from the processed biological particle.

131. The method of any one of paragraphs 68-130, additionally comprising separating and/or removing the support and/or the attached catalyst from the processed biological particle using an electromagnetic, electromotive, magnetic and/or mechanical force.

132. The method of any one of paragraphs 68-131, additionally comprising separating and/or removing the support and/or the attached catalyst from the processed biological particle using a centrifugal force.

133. The method of any one of paragraphs 68-132, additionally comprising separating and/or removing the support and/or the attached catalyst from the processed biological particle by filtering and/or affinity separation.

134. The method of any one of paragraphs 68-133, additionally comprising separating and/or removing the support and the attached catalyst from the processed biological particle based on differences in physical characteristics of the support as compared to the processed biological particle.

135. The method of any one of paragraphs 68-134, additionally comprising partitioning the processed biological particle into a discrete droplet.

136. The method of any one of paragraphs 68-135, additionally comprising generating a discrete droplet that encapsulates the processed biological particle.

137. The method of any one of paragraphs 68-136, additionally comprising generating a discrete droplet that encapsulates the processed biological particle using a microfluidic device.

138. The method of any one of paragraphs 68-137, additionally comprising generating a discrete droplet that encapsulates the processed biological particle at least in part by:
    i) providing a mixture comprising:
      a) a first phase comprising the processed biological sample; and
      b) a second phase immiscible with the first phase; and
    ii) subjecting the mixture to agitation.

139. The method of any one of paragraphs 68-138, additionally comprising generating a discrete droplet that encapsulates the processed biological particle, the biological particle also including at least one of:
    i) a unique molecular identifier, the identifier including a unique oligonucleotide or barcode sequence;
    ii) a bead; and
    iii) one or more assay reagents, including an enzyme.

140. The method of any one of paragraphs 68-139, wherein the biological particle comprises an aggregate or clump of cells, the processed biological particle comprises a single cell, and additionally comprising:
    partitioning the processed biological particle into a discrete droplet;
    creating a library of nucleotide sequences, from the processed biological particle, in the discrete droplet; and
    obtaining nucleotide sequence information from clones of the library.

141. A catalyst attached to a support, as described in any of the methods of paragraphs 68-140.

142. A composition, comprising a biological particle as described in any of the methods of paragraphs 68-140, and a catalyst attached to a support as described in any of the methods of paragraphs 1-73.

143. A composition, comprising a discrete droplet that encapsulates a processed biological particle, the processed biological particle prepared by the method of any one of paragraphs 68-140.

144. A method for reducing clumping of cells, comprising:
    contacting a biological sample that contains clumped or aggregated cells with beads conjugated to a nuclease;
    incubating the biological sample containing the cells and beads under conditions such that the nuclease is active on an extracellular nucleic acid in the biological sample; and
    removing the beads and nuclease from the biological sample that contains the cells and the beads, leaving cells that have reduced clumping as compared to clumped or aggregated cells prior to the contacting step.

145. The method of paragraph 144, wherein the biological sample comprises cryopreserved cells that have been thawed.

146. The method of one of paragraphs 144 or 145, wherein the biological sample comprises peripheral blood mononuclear cells (PBMCs).

147. The method of any one of paragraphs 144-146, wherein the biological sample comprises extracellular DNA.

148. The method of any one of paragraphs 144-147, wherein the nuclease includes a deoxyribonuclease (DNase).

149. The method of any one of paragraphs 144-148, wherein the beads are removed from the biological sample using an electromagnetic, electromotive, magnetic and/or mechanical force.

150. The method of any one of paragraphs 144-148, wherein the beads are removed from the biological sample using chromatographic, electrophoretic, immunological, hydrodynamic and/or ligand binding methods.

151. The method of any one of paragraphs 144-148, wherein the beads are removed from the biological sample using a sedimentation-based or filtering method.

152. The method of any one of paragraphs 144-151, additionally comprising generating a discrete droplet that encapsulates the processed biological particle using a microfluidic device.

153. The method of any one of paragraphs 144-152, additionally comprising generating a discrete droplet that encapsulates the processed biological particle, and also comprises one or more of a barcode, a bead that optionally is attached to the barcode, an enzyme, a primer and a template.

154. A method for reducing the number of cells in a cell aggregate contained in a sample, comprising treating the cell aggregate in the sample with a nuclease enzyme attached to a bead, and subsequently removing the bead and attached enzyme from the sample, leaving single cells or a cell aggregate containing a reduced number of cells compared to the cell aggregate prior to the treating.

155. A kit, comprising:
  a support comprising an attached catalyst, or a support and a catalyst, wherein the support is configured to attach to the catalyst; and
  printed instructions describing the method of any one of paragraphs 68-140.

156. A kit, comprising:
  a support comprising an attached catalyst, or a support and a catalyst, wherein the support is configured to attach to the catalyst;
  printed instructions describing the method of any one of paragraphs 68-140; and
  optionally, a device or component configured to remove the support and catalyst from a biological sample.

157. A kit, comprising:
  a nuclease enzyme attached to a bead;
  printed instructions describing or referencing the method of any one of paragraphs 68-140; and
  optionally, at least one substance that, when added to a sample comprising an aggregate or clump of cells and the nuclease enzyme attached to a bead, improves or is required for activity of the nuclease.

158. The kit of paragraph 157, wherein the nuclease enzyme includes a DNase.

159. The kit of paragraph 157 or 158, wherein the bead includes a gel, solid and/or magnetic bead.

160. The kit of any one of paragraphs 157-159, wherein the kit additionally includes a device or component configured to remove the support and catalyst from a biological sample, wherein the device or component includes a magnet, a column, a tube, an antibody or an enzyme.

EXAMPLES

Examples of a support comprising an enzyme attached thereto are provided in FIG. 1. FIG. 1 shows a support 108 that includes a catalyst 106, which may be an enzyme. The support 108 may include or be a bead. The catalyst 106 may be attached on the surface of the support 108.

As an example, enzyme may be a ribonuclease (RNase) and/or a deoxyribonuclease (DNase). The RNase and/or DNase may be configured to degrade an extracellular RNA and/or DNA in a sample. In some examples, the support 108 may be used to degrade an mRNA in or prior to a single-cell RNA sequencing experiment.

Ribonuclease (RNase) is a type of nuclease that may catalyze the degradation of RNA into smaller components. As an example, RNase may cleave the 3' end of unpaired C and U residues and may form a 3'-phosphorylated product via a 2',3'-cyclic monophosphate intermediate. Extracellular RNA molecules, such as mRNA molecules may be digested by the support 108. The intracellular RNA molecules such as RNA and other intracellular molecules may not be digested by the bead 108 due to the methods provided herein and therefore, may remain intact and/or untouched. Molecule fragments (e.g., extracellular nucleic acid fragments such as the fragments of the digested mRNA) may remain behind in the sample.

The method may further comprise separating the support 108 from the sample using the methods provided elsewhere herein. The remaining extracellular nucleic acid fragments may not interfere with the single cell sequencing data, and therefore it may not be necessary to separate the extracellular nucleic acid fragments from the sample. Optionally, the remaining extracellular nucleic acid fragments can be further separated from the sample; however, there is a chance that such further processing of the sample releases more extracellular molecules such as extracellular nucleic acid molecules (e.g., DNA, RNA, or other molecules) into the sample.

Referring to FIG. 1, enzyme 106 may be a nuclease, such as an exonuclease. The support 108 may be referred to as a bead-bound nuclease, such as a bead-bound exonuclease. Exonucleases may comprise any exonuclease. As an example, an exonuclease may be Exonuclease I (ExoI). ExoI may degrade single-stranded deoxynucleotide DNA in a 3'→5' direction. It may release deoxyribonucleoside 5'-monophosphates (e.g., in a stepwise manner) and leave the 5-terminal dinucleotides intact. Support 108 may digest extracellular (e.g., ambient or background) nucleic acid molecules such as DNA (e.g., genomic DNA (gDNA)). The support 108 may not digest intracellular gDNA and chromatin structure. Therefore, intracellular gDNA and chromatin structure and/or other intracellular nucleic acid molecules may remain intact and/or untouched.

Figure 15:
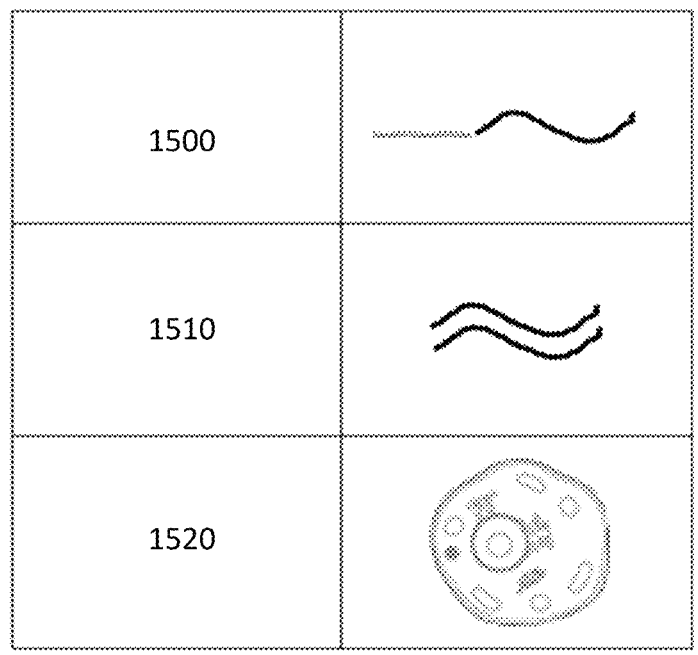
FIG. 15 schematically illustrates a ribonucleic acid (RNA), a deoxyribonucleic acid (DNA), and a cell.

FIG. 15 schematically shows an mRNA 1500, a gDNA 1510 and a cell 1520 as examples. The cell may comprise intracellular RNA and DNA, such as intracellular mRNA and gDNA. The methods of the present disclosure can be used to digest mRNA and gDNA that may be floating freely as extracellular, ambient, or background extracellular nucleic acid molecules in the sample, while maintaining the intracellular DNA and RNA such as mRNA and gDNA inside the cells or cell nuclei in the sample intact, unaffected, and/or untouched. For example, the support 108 (shown in FIG. 1), or any other support provided and/or described elsewhere herein that comprises an enzyme (e.g., attached thereto), such as a nuclease, ribonuclease, exonuclease, or other enzyme may digest or degrade an extracellular molecule such as an extracellular nucleic acid molecule such as mRNA 1500 or gDNA 1510, while intracellular mRNA and gDNA present in the cell 1520 or a cell nucleus in the sample remain intact. Nucleus may be the nucleus of the cell 1520, or a nucleus (not shown) in the sample that is not inside a cell.

An example workflow for performing the methods of the present disclosure and providing the compositions of the present disclosure is provided in FIG. 16. A sample (e.g., sample 1600) may comprise a cell 1520. The cell may comprise a nucleus 1530. Alternatively, or in addition, the sample may comprise a nucleus (not shown) that is outside a cell. For example, a sample 1600 may comprise a cell nucleus that is outside a cell, while the sample does not comprise a cell. The sample 1600 may further comprise an extracellular molecule. The extracellular molecule may be an extracellular nucleic acid molecule such as a DNA or RNA. The extracellular nucleic acid molecule may be an mRNA 1500. The sample may be brought into contact with a support (e.g., support 108) comprising one or more enzymes. The enzymes may be inside the support or may be attached to the support. For example, the enzymes may be attached to the surface of the support. The support 108 may be similar to the support shown in FIG. 1. Therefore, the sample 1610 may comprise cells 1520, cell nuclei (e.g., similar to cell nucleus 1530 or a cell nucleus (not shown) outside of a cell), and a plurality of supports (e.g., support 108) that have an enzyme attached thereto. The sample 1600 may further comprise a plurality of extracellular nucleic acid molecules such as mRNA 1500. The support 108 may digest the extracellular molecules (e.g., extracellular mRNA 1500) to yield a processed sample 1620. The extracellular nucleic acid molecules may be larger than about 60 base pair (bp), 70 bp, 80 bp, 90 bp, 100 bp, 200 bp, 300 bp, 400 bp, 500 bp, 600 bp, 700 bp, 800 bp, 900 bp, 1 kbp, or larger in size. The support may digest the extracellular nucleic acid molecules to smaller fragments (e.g., nucleic acid molecule fragments described elsewhere herein). Subsequent to the digestion, the support 108 may be separated from the sample 1610, yielding a processed sample 1620 that may be substantially free of supports (e.g., support 108) and substantially free from extracellular molecules (e.g., mRNA 1500). Alternatively, a portion of the supports (e.g., support 108) may remain in the sample 1620. For example, at most about 99%, 90%, 80%, 70%, 60%, 50%, 40%, 30%, 20%, 10%, 5%, 1% or less of the initial support concentration may remain in the processed sample 1620.

With continued reference to FIG. 16, the processed sample 1620 may comprise a cell (e.g., cell 1630). The processed sample 1620 may comprise a cell nucleus 1640 inside the cell 1630. Alternatively, or in addition, the processed sample may further comprise a cell nucleus (not shown) outside a cell. The cell 1630 may be substantially similar to the cell 1520. For example, the cell may not have been substantially changed during the workflow. The workflow presented in FIG. 16 may digest the extracellular nucleic acid molecules (e.g., extracellular mRNA 1500) while leaving the intracellular nucleus and/or other intracellular components, pathways, molecules, such as DNA and RNA, cell membrane, intracellular activities, and functions substantially intact and/or untouched. The sample 1620 may further comprise a plurality of nucleic acid molecule fragments. The nucleic acid molecule fragments may be smaller than about 60 base pairs (bp) in size. For example, the nucleic acid molecule fragments may be at most about 60 bp, 50 bp, 40 bp, 30 bp, 20 bp, 10 bp, 5 bp or smaller in size. The processed sample may be substantially free of extracellular nucleic acid molecules larger than at least about 60 bp, 70 bp, 80 bp, 100 bp, 200 bp, 300 bp, 400 bp, 500 bp, 600 bp, 700 bp, 800 bp, 900 bp, 1 kbp, or larger in size. Alternatively, a portion of the extracellular nucleic acid molecules may remain in the processed sample. For example, at most about 99%, 90%, 80%, 70%, 60%, 50%, 40%, 30%, 20%, 10%, 5%, 1% or less of the initial extracellular nucleic acid molecules present in the sample 1600 may remain in the processed sample 1620.

Another example workflow for performing the methods of the present disclosure and/or providing the compositions of the present disclosure is provided in FIG. 17. A sample 1700 may comprise a cell and/or a cell nucleus. The cell nucleus may be inside the cell, such as cell nucleus 1530, or may be outside the cell (not shown) in the sample. Alternatively, an example sample to be processed may comprise a cell nucleus outside a cell, and not comprise a cell. A sample may comprise both a cell and a cell nucleus. The sample 1700 may further comprise an extracellular molecule. The extracellular molecule may be an extracellular nucleic acid molecule. The extracellular nucleic acid molecule may be a deoxyribonucleic acid molecule (DNA), such as a genomic DNA (gDNA) 1510. In some cases, the extracellular nucleic acid molecule may be a DNA. In some examples, the extracellular nucleic acid molecule may be a chromosome. The size of the extracellular nucleic acid molecule may be listed elsewhere herein.

The workflow shown in FIG. 17 may be used to digest or degrade the extracellular molecule, for example the gDNA 1510 in the sample to yield a processed sample such as sample 1720.

The workflow shown in FIG. 17 may comprise bringing a support in contact with the sample. The sample 1710 comprises a support, such as support 108 which comprises an enzyme. The enzyme may be attached to the support, for example to the surface of the support. The support may be similar to the support 108 shown in FIG. 1. The support may be configured to digest and/or degrade the extracellular molecule (e.g., gDNA 1510) in the sample 1710 to yield a processed sample. The support 108 may be according to the supports provided elsewhere herein. The enzyme may be a nuclease, such as an exonuclease. An example of the enzyme attached to the support 108 may be ExoI. The support 108 may degrade the extracellular nucleic acid molecule. The support 108 may be subsequently separated from the sample 1710. For example, the support may be a magnetic support, such as a solid magnetic microsphere that may be configured to be separated from the sample using a magnetic or electromagnetic force. The support 108 may be separated from the sample 1710 upon application of a magnetic force, thereby yielding a processed sample that may be substantially free of the supports 108 and extracellular molecules such as extracellular DNA (e.g., gDNA 1510).

The processed sample 1720 may comprise a cell 1730. The cell 1730 comprises a nucleus 1740. Alternatively, or in addition, the processed sample 1720 may comprise a nucleus (not shown) that is outside a cell. The cell 1730 may be substantially similar to the cell 1520. The cell 1730 may have remained substantially unaltered as a result of the workflow. For example, the support 108 may not affect the cell. The cell may maintain viable. The intracellular DNA and RNA, nucleus, other organelles, other workflows, the cell membrane, cell functions, and cellular metabolism, may remain sufficiently intact and unaltered for additional processing. The processed sample 1720 may further comprise nucleic acid fragments. Nucleic acid molecule fragments may be smaller than about 60 bp, 50 bp, 40 bp, 30 bp, 20 bp, 10 bp, 5 bp or smaller in size. The nucleic acid molecule fragments may not interfere with further processing of the sample and data analysis, such as single cell DNA or RNA sequencing analysis.

In some examples, the processed sample (e.g., processed sample 1620 or 1720), may be partitioned or compartmentalized into a plurality of partitions. The partition may be a droplet or a microwell. The droplet may be according to the droplets provided elsewhere herein. For example, the droplet may be an aqueous droplet surrounded by an immiscible oil. The droplet may be made using a microfluidic device provided herein. Alternatively, or in addition, the processed sample may be in a container, such as shown in FIG. 16 or 17. A phase immiscible with the sample, such as an oil may be added to the sample in the container. The container (or another container or platform) may be subjected to agitation such as vortexing. Droplets may be generated in the sample and thereby compartmentalizing the processed sample in the partitions (e.g., droplets). The partitions may act as vessels. The processed sample may be further processed. For example, the processed sample may be subject to sequencing, such as single cell (e.g., DNA or RNA) sequencing. In some examples, sequencing or single cell sequencing may be according to the methods provided elsewhere herein.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

The invention claimed is:

1. A composition, comprising:
   (a) an exonuclease coupled to a support, wherein the exonuclease coupled to the support is capable of degrading an extracellular nucleic acid and is incapable of degrading intracellular genomic deoxyribonucleic acid (gDNA) and chromatin; and
   (b) a biological sample comprising cells or nuclei.

2. The composition of claim 1, wherein the exonuclease is covalently attached to the support.

3. The composition of claim 1, wherein the exonuclease is noncovalently coupled to a surface moiety on the support.

4. The composition of claim 1, wherein the support is a magnetic support.

5. The composition of claim 1, wherein the support comprises a bead.

6. The composition of claim 5, wherein the bead is a gel bead.

7. The composition of claim 1, wherein the support comprises a a dimension of from 5 micrometers (μm) to 10 micrometers (μm).

8. The composition of claim 1, wherein the support comprises a polymer.

9. The composition of claim 8, wherein the polymer is selected from the group consisting of: acrylics, nylons, silicones, spandex, viscose rayon, polycarboxylic acids, polyvinyl acetate, polyacrylamide, polyacrylate, polyethylene glycol, polyurethanes, polylactic acid, silica, polystyrene, polyacrylonitrile, polybutadiene, polycarbonate, polyethylene, polyethylene terephthalate, poly (chlorotrifluoroethylene), poly(ethylene oxide), poly (ethylene terephthalate), polyethylene, polyisobutylene, poly(methyl methacrylate) poly(oxymethylene), polyformaldehyde, polypropylene, polystyrene, poly(tetrafluoroethylene), poly(vinyl acetate), poly(vinyl alcohol), poly(vinyl chloride), poly(vinylidene dichloride), poly(vinylidene difluoride), and poly(vinyl fluoride).

10. The composition of claim 1, wherein the support is insoluble in the biological sample.

11. The composition of claim 1, wherein the support has a dimension of at least 1 micrometer (μm).

12. The composition of claim 1, further comprising: reagents that comprise (A) a first phase and (B) a second phase immiscible with the first phase.

13. The composition of claim 1, further comprising a plurality of nucleic acid barcode molecules.

14. The composition of claim 13, wherein nucleic acid barcode molecules of the plurality of nucleic acid barcode molecules are coupled to a bead.

15. A system comprising the composition of claim 1, further comprising a component configured to apply a force to the support coupled to the exonuclease and separate the support coupled to the exonuclease from the biological sample comprising cells or nuclei.

16. The system of claim 15, wherein the component comprises a magnet or a column.

17. The system of claim 15, wherein the component comprises an antibody.

18. The system of claim 15, wherein the component comprises a microfluidic device.

19. The system of claim 18, wherein the microfluidic device comprises a plurality of wells.

* * * * *